US008536360B2

(12) United States Patent
Kim et al.

(10) Patent No.: US 8,536,360 B2
(45) Date of Patent: Sep. 17, 2013

(54) COMPOSITIONS AND METHODS FOR STEREOSELECTIVE ALDEHYDE ALLYLATION AND CROTYLATION

(75) Inventors: Hyunwoo Kim, Daejeon (KR); James Lincoln Leighton, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 339 days.

(21) Appl. No.: 13/089,708

(22) Filed: Apr. 19, 2011

(65) Prior Publication Data

US 2012/0190875 A1     Jul. 26, 2012

Related U.S. Application Data

(60) Provisional application No. 61/434,578, filed on Jan. 20, 2011.

(51) Int. Cl.
*C07F 7/00*     (2006.01)
*C07C 27/00*     (2006.01)

(52) U.S. Cl.
USPC ........................ 556/407; 252/182.11; 568/878

(58) Field of Classification Search
USPC ..................... 568/878; 556/407; 252/182.11
See application file for complete search history.

(56) References Cited

U.S. PATENT DOCUMENTS

| | | |
|---|---|---|
| 7,534,905 B2 | 5/2009 | Leighton et al. |
| 2008/0167468 A1 | 7/2008 | Leighton et al. |

OTHER PUBLICATIONS

Berger et al., Enantioselective Allylation of Ketone-Derived Benzoylhydrazones: Practical Synthesis of Tertiary Carbinamines, J. Am. Chem. Soc., vol. 126, pp. 5686-5687 (2004).
Brown et al., ", Asymmetric carbon-carbon bond formation via .beta.-allyldiisopinocampheylborane. Simple synthesis of secondary homoallylic alcohols with excellent enantiomeric purities," J. Am. Chem. Soc., vol. 105, pp. 2092-2093 (1983).
Brown et al., "Enantiomeric Z- and E-crotyldiisopinocampheylboranes. Synthesis in high optical purity of all four possible stereoisomers of .beta.-methylhomoallyl alcohols," J. Am. Chem Soc., vol. 108, pp. 293-294 (1986).
Brown et al., Chiral synthesis via organoboranes. 7. Diastereoselective and enantioselective synthesis of erythro- and threo-.beta.-methylhomoallyl alcohols via enantiomeric (Z)- and (E)-crotylboranes J. Am. Chem Soc., vol. 108, pp. 5919-5923 (1986).
Burgos et al., "Asymmetric Allyl- and Crotylboration with the Robust, Versatile, and Recyclable 10-TMS-9-borabicyclo[3.3.2]decanes," J. Am. Chem. Soc., vol. 127, pp. 8044-8049 (2005).
Burns et al., "The Enantioselective Allylation and Crotylation of Sterically Hindered and Functionalized Aryl Ketones: Convenient Access to Unusual Tertiary Carbinol Structures," Angew. Chem. Int. Ed., vol. 45, pp. 3811-3813 (2006).
Chemler et al., "Recent Applications of the Allylation reactionto the synthesis of Natural products," Modern Carbonyl Chemistry, Chapter 11, pp. 403-490, (Otera, J. Ed.), Wiley-VCH, Weinheim (2000).
Corey et al., "A practical and efficient method for enantioselective allylation of aldehydes," J. Am. Chem. Soc., vol. 111, pp. 5495-5496 (1989).

(Continued)

*Primary Examiner* — Porfirio Nazario Gonzalez
(74) *Attorney, Agent, or Firm* — Wilmer Cutler Pickering Hale and Dorr LLP

(57) ABSTRACT

Compositions and methods for practical, stereoselective allylation and crotylation for aldehyde substrates are described. The compositions and methods comprise reagents for allylation and/or crotylation and acids. In some embodiments, the reagents and acids are pre-mixed.

56 Claims, 54 Drawing Sheets

(56) References Cited

OTHER PUBLICATIONS

Denmark et al., "Allylation of Carbonyls: Methodology and stereochemistry," Modern Carbonyl Chemistry, Chapter 10, pp. 299-401(Otera, J. Ed.), Wiley-VCH, Weinheim (2000).
Evans et al., "Double Stereodifferentiating Aldol Reactions. The Documentation of "Partially Matched" Aldol Bond Constructions in the Assemblage of Polypropionate Systems," J. Am. Chem Soc., vol. 117, pp. 9073-9074 (1995).
Faller et al., "Enantioselective syntheses of secondary homoallyl alcohols with optically active .eta.3-allylmolybdenum complexes," J. Am. Chem. Soc., vol. 111, pp. 1937-1939 (1989).
Garcia et al., "Asymmetric addition of (E)- and (Z)-crotyl-trans-2,5-dimethylborolanes to aldehydes," J. Org. Chem., vol. 52, pp. 4831-4832 (1987).
Hackman et al., "Highly Diastereo- and Enantioselective Reagents for Aldehyde Crotylation," Org. Lett., vol. 6, pp. 4375-4377 (2004).
Hafner et al., "Enantioselective syntheses with titanium carbohydrate complexes. Part 7. Enantioselective allyltitanation of aldehydes with cyclopentadienyldialkoxyallyltitanium complexes," J. Am. Chem. Soc., vol. 114, pp. 2321-2336 (1992).
Herold et al., "Enantioselective Synthesis of Homoallyl Alcohols via Chiral Allylboronic Esters," Angew. Chem. Int. Ed. Eng., vol. 17, pp. 768-769 (1978).
Ishiyama et al., "Acceleration effect of lewis acid in allylboration of aldehydes: Catalytic, regiospecific, diasterospecific, and enantioselective synthesis of homoallyl alcohols," J. Am. Chem. Soc., vol. 124, pp. 12414-12415 (2002).
Jadhav et al., "Chiral synthesis via organoboranes. 6. Asymmetric allylboration via chiral allyldialkylboranes. Synthesis of homoallylic alcohols with exceptionally high enantiomeric excess," J. Org. Chem, vol. 51, pp. 432-439 (1986).
Jain et al., "Chiral Brønsted Acid-Catalyzed Allylboration of Aldehydes," J. Am. Chem. Soc., vol. 132, pp. 11884-11886 (2010).
Jain et al., "Double-Stereodifferentiating Crotylation Reactions with Chiral (E)-Crotylsilanes. Evaluation of a New Approach for the Synthesis of Polypropionate-Derived Natural Products," J. Am. Chem. Soc., vol. 118, pp. 12475-12476 (1996).
Kennedy et al., "Dramatic Rate enhancement with preservation of stereospecificity in the first metal-catalyzed of allylboronates,", J. Am. Chem. Soc., vol. 124, pp. 11586-11587 (2002).
Kennedy et al., "Lewis acid catalyzed allylboration: Discovery, optimization, and application to the formation of stereogenic quaternary carbon centers," J. Org. Chem, vol. 69, pp. 4412-4428 (2004).
Kim et al.,"A more comprehensive and highly practical solution to Enantioselective aldehyde crotylation," J. Am. Chem Soc., vol. 133, 4 pages (2011).
Kim et al., "anti-Diastereo- and Enantioselective Carbonyl Crotylation from the Alcohol or Aldehyde Oxidation Level Employing a Cyclometallated Iridium Catalyst: α-Methyl Allyl Acetate as a Surrogate to Preformed Crotylmetal Reagents," J. Am. Chem. Soc., vol. 131, pp. 2514-2520 (2009).
Kubota et al., "A highly pratical and enantioselective reagent for the allylation of aldehydes," Angew. Chem Int. Ed., vol. 42, pp. 946-948 (2003).
Lachance et al, "Scandium-catalyzed allyboration of aldehydes as a practical method for highly diastereo and enantioselective construction of homoallylic alcohols," J. Am. Chem. Soc., vol. 125, pp. 10160-10161 (2003).
Liu et al., "Layer-by-layer Synthesis of Metal-containing conducting polymers: Caged metal centers for interlayer charge transport," J. Am. Chem Soc., vol. 132, pp. 11844-11846 (2010).
Racherla et al., "Chiral synthesis via organoboranes. 27. Remarkably rapid and exceptionally enantioselective (approaching 100% ee) allylboration of representative aldehydes at -100.degree. under new, salt-free conditions," J. Org. Chem, vol. 56, pp. 401-404 (1991).
Rauniyar et al., "Catalytic Enantioselective Allyl- and Crotylboration of Aldehydes Using Chiral Diol•SnCl₄ Complexes. Optimization, Substrate Scope and Mechanistic Investigations," J. Am. Chem. Soc., vol. 130, pp. 8481-8490 (2008).
Rauniyar et al., "Lewis Acids catalyze the addition of allylboronates to aldehydes by eletrophilic activation of the dioxaborolane in a closed transition structure," J.Am. Chem. Soc., vol. 126, pp. 4518-4519 (2004).
Rauniyar et al., Catalytic Enantioselective and Catalyst-Controlled Diastereofacial-Selective Additions of Allyl- and Crotylboronates to Aldehydes Using Chiral Brønsted Acids, Angew. Chem Int. Ed., vol. 45, pp. 2426-2428 (2006).
Reetz et al., "Highly enantioselective addition of a Chirally modified allylboron reagent to aldehydes," Chemistry Industry, Issue No. 1, pp. 663-664 (1988).
Roush et al., "Asymmetric synthesis using diisopropyl tartrate modified (E)- and (Z)-crotylboronates: preparation of the chiral crotylboronates and reactions with achiral aldehydes," J. Am. Chem. Soc. vol. 112, pp. 6339-6348 (1990).
Roush et al., "Diastereo- and enantioselective aldehyde addition reactions of 2-allyl-1,3,2-dioxaborolane-4,5-dicarboxylic esters, a useful class of tartrate ester modified allylboronates," J. Am. Chem. Soc., vol. 107, pp. 8186-8190 (1985).
Roush et al., "N,N'-Bis(2,2,2-trifluoroethyl)-N,N'-ethylenetartramide: An Improved Chiral Auxiliary for the Asymmetric Allylboration Reaction," J. Org. Chem, vol. 60, pp. 3806-3813 (1995).
Roush et al., "N,N'-dibenzyl-N,N'-ethylenetartramide: a rationally designed chiral auxiliary for the allylboration reaction," J. Am. Chem. Soc., vol. 110, pp. 3979-3982 (1988).
Roush,"AllylOrganometallics," Comprehensive Organic Synthesis, vol. 2, Additions to C-X $_\pi$-bonds, part 2, pp. 1-53 (1991).
Short et al., "Asymmetric allylboration with B-allyl-2-(trimethylsilyl)borolane," J. Am. Chem. Soc., vol. 111, pp. 1892-1894 (1989).
Spletstoser et al., "Tandem Silylformylation-Crotylsilylation/Tamao Oxidation of Internal Alkynes: A Remarkable Example of Generating Complexity from Simplicity," Org. lett. vol. 10, pp. 5593-5596 (2008).
Yu et al., "Bronsted Acid-Catalyzed Allylboration: Short and Stereodivergent Synthesis of All Four Eupomatilone Diastereomers with Crystallographic Assignments," J. Am. Chem. Soc., vol. 127, p. 12808-12809 (2005).
Denmark et al., "Catalytic enantioselective addition of substituted Allylic trichlorosilanes using a rationally-designed 2,2'-bispyrrolidine-bases bisphosphoramide," J. Am. Chem. Soc., vol. 123, pp. 9488-9489 (2001).

(R,R)-1 + Sc(OTf)$_3$ → (R,R)-cis EZ-Crotyl Mix
25:1 molar ratio
(50 g) →

COMPOSITIONS AND METHODS FOR STEREOSELECTIVE ALDEHYDE ALLYLATION AND CROTYLATION

This application claims the benefit of and priority to U.S. provisional patent application Ser. No. 61/434,578 filed Jan. 20, 2011, the entire disclosure of which is hereby incorporated by reference in its entirety for all purposes.

This invention was made with government support under NIGMS R01 GM58133 awarded by the National Institute of Health. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications, publications and other references cited herein are hereby incorporated by reference in their entirety. The disclosures of these publications in their entireties are hereby incorporated by reference into this application in order to more fully describe the state of the art as known to those skilled therein as of the date of the invention described herein.

BACKGROUND OF THE INVENTION

The importance of diastereo- and enantioselective aldehyde allylation and crotylation is demonstrated by the direct relevance to the products of these reactions to important classes of natural products and other compounds of biological relevance. While stereoselective aldehyde allylation and crotylation methods have been developed, many suffer from drawbacks related to practical liabilities such as low temperature metallation procedures, multiple steps in carrying out the reactions and complex work-up procedures. Additionally, the practicability of such methods has been limited, due to requirements of low temperature metallation and in situ generation of the reagent.

SUMMARY

There is a need for a practical method of diastereo- and enantioselective aldehyde allylation and crotylation that is applicable to a range of aldehyde electrophiles. There is also a need for a general, practical methodology that provides a comprehensive solution for stereoselective allylation and/or crotylation of aldehydes containing differing stereochemical configurations. This invention addresses these needs.

In one aspect, the methods described herein relate to a method for stereoselective allylation of aldehydes. In another aspect, the methods described herein relate to a method for stereoselective crotylation of aldehydes. In another aspect, the invention relates to a pre-mixed crotylsilane-Lewis acid system for use in stereoselective aldehyde crotylation. In another aspect, the invention relates to a pre-mixed allylsilane-Lewis acid system for use in stereoselective aldehyde allylation.

In one embodiment, the invention relates to a method for allylation comprising treatment of an aldehyde with a compound of formula A, and a Lewis acid;

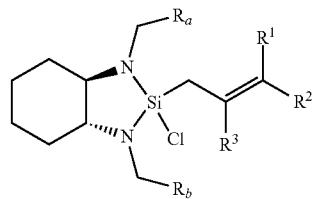

A wherein $R^1$ and $R^2$ are independently hydrogen or halogen, and $R^3$ is selected from the group consisting of hydrogen, halogen, and alkyl; and wherein $R_a$ and $R_b$ are independently selected from the group consisting of hydrogen, alkyl, aryl and heteroaryl.

In one embodiment, the compound of formula A is (R,R)-13. In another embodiment, the compound of formula A is (S,S)-13.

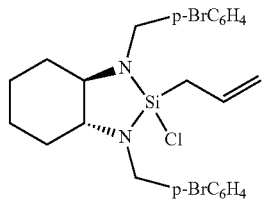

(R,R)-13

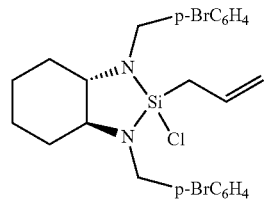

(S,S)-13

In one embodiment, the invention relates to a method for crotylation comprising treatment of an aldehyde with a compound of formula A, and a Lewis acid;

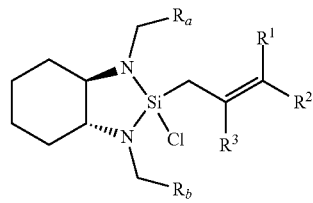

A wherein $R^1$, $R^2$, and $R^3$ are independently selected from the group consisting of hydrogen, halogen, and alkyl; and wherein at least one of $R^1$ and $R^2$ is alkyl; and wherein $R_a$ and $R_b$ are independently selected from the group consisting of hydrogen, alkyl, aryl and heteroaryl.

In one embodiment, the compound of formula A is (R,R)-1. In another embodiment, the compound of formula A is (S,S)-1.

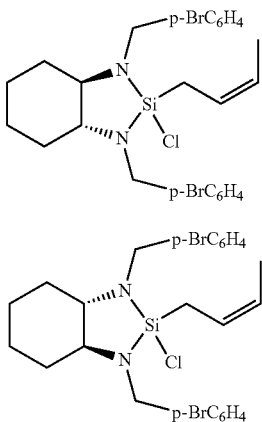
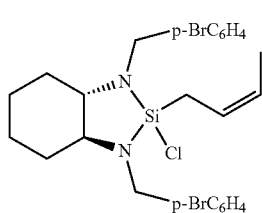

In one embodiment, the compound of formula A is (R,R)-2. In another embodiment, the compound of formula A is (S,S)-2.

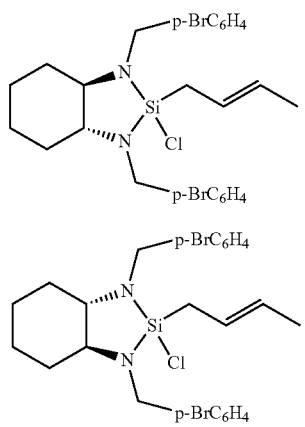
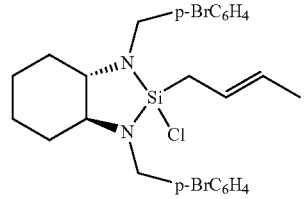

In another aspect, the invention relates to a pre-mixed silane-Lewis acid system or composition for use in stereoselective aldehyde allylation or crotylation, wherein the silane is a silane of formula A.

In one embodiment, the pre-mixed silane-Lewis acid system comprises an allylsilane. In another embodiment, the pre-mixed silane-Lewis acid system comprises a crotylsilane.

In one embodiment, the invention comprises a compound of formula A and a Lewis acid.

In one embodiment, the compound of formula A is (R,R)-1. In another embodiment, the compound of formula A is (S,S)-1.

In one embodiment, the compound of formula A is (R,R)-2. In another embodiment, the compound of formula A is (S,S)-2.

In one embodiment, the compound of formula A is (R,R)-13. In another embodiment, the compound of formula A is (S,S)-13.

In one embodiment, the Lewis acid is selected from the group consisting of aluminum chloride, yttrium triflate, and scandium triflate. In yet another embodiment, the Lewis acid is scandium triflate.

The following examples illustrate the present invention, and are set forth to aid in the understanding of the invention, and should not be construed to limit in any way the scope of the invention as defined in the claims which follow thereafter.

DETAILED DESCRIPTION OF THE INVENTION

Figure 1:
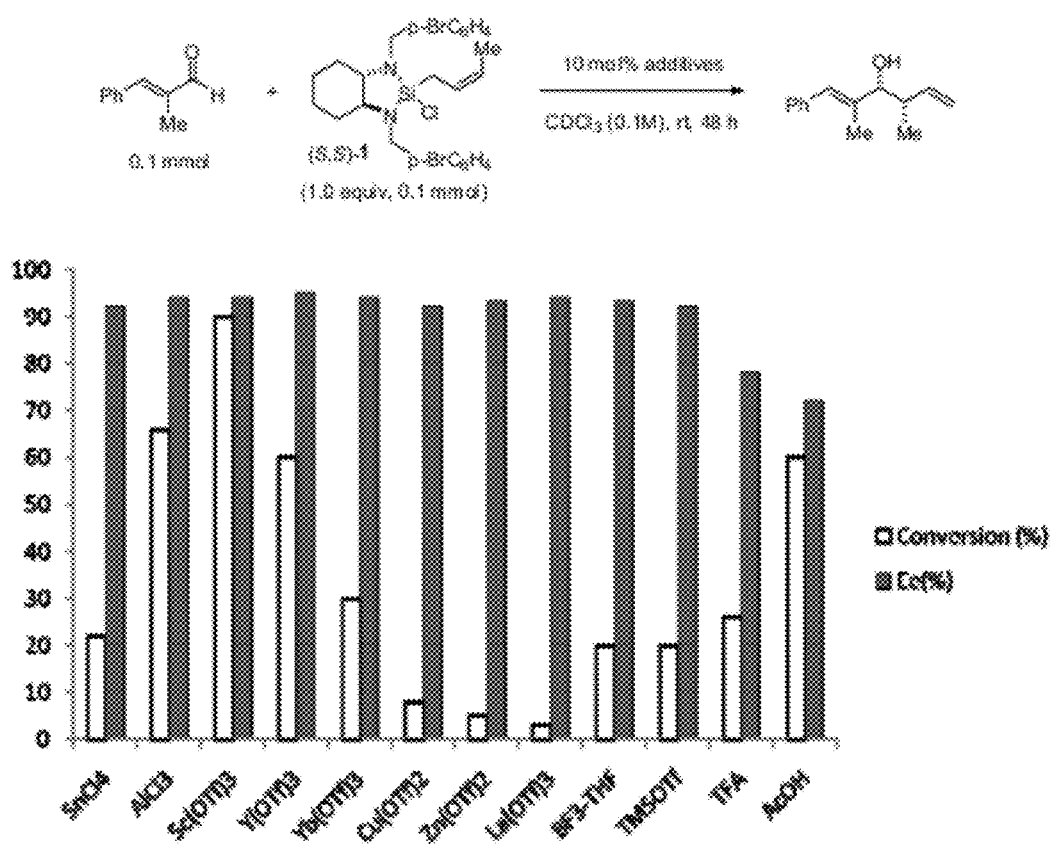
FIG. 1. Effects of Lewis or Bronstead acids on the silane-mediated aldehyde crotylation using (S,S)-1.

In one embodiment, the invention relates to a method for allylation comprising treatment of an aldehyde with a compound of formula A, and a Lewis acid;

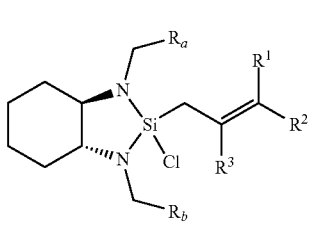

A wherein W and R$^2$ are independently hydrogen or halogen; and R$^3$ is selected from the group consisting of hydrogen, halogen, and alkyl; and wherein R$_a$ and R$_b$ are independently selected from the group consisting of hydrogen, alkyl, aryl and heteroaryl.

In one embodiment, R$^1$ and R$^2$ are hydrogen. In another embodiment, R$^1$, R$^2$, and R$^3$ are hydrogen.

In one embodiment, the invention relates to a method for crotylation comprising treatment of an aldehyde with a compound of formula A, and a Lewis acid

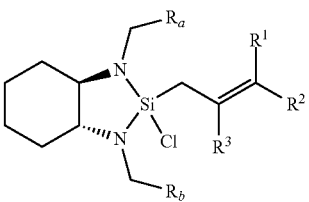

A wherein R$^1$, R$^2$, and R$^3$ are independently selected from the group consisting of hydrogen, halogen, and alkyl; and wherein at least one of R$^1$ and R$^2$ is alkyl; and wherein R$_a$ and R$_b$ are independently selected from the group consisting of hydrogen, alkyl, aryl and heteroaryl.

In one embodiment, R$^1$ is alkyl. In another embodiment R$^1$ is C$_1$-C$_4$ alkyl. In yet another embodiment, R$^1$ is methyl.

In one embodiment, R$^1$ is alkyl, and R$^2$ and R$^3$ are hydrogen. In another embodiment, R$^1$ is methyl, and R$^2$ and R$^3$ are hydrogen.

In one embodiment, R$^2$ is alkyl. In another embodiment R$^2$ is C$_1$-C$_4$ alkyl. In yet another embodiment, R$^2$ is methyl.

In one embodiment, R$^2$ is alkyl, and R$^1$ and R$^3$ are hydrogen. In another embodiment, R$^2$ is methyl, and R$^1$ and R$^3$ are hydrogen.

In one embodiment, R$^1$ and R$^2$ are alkyl. In another embodiment, R$^1$ and R$^2$ are alkyl, and R$^3$ is hydrogen.

In one embodiment, R$^3$ is alkyl. In another embodiment, R$^3$ is methyl.

In one embodiment, R$_a$ and R$_b$ are both hydrogen.
In one embodiment, R$_a$ and R$_b$ are both alkyl.
In one embodiment, R$_a$ and R$_b$ are both aryl.
In one embodiment, R$_a$ and R$_b$ are both halo-substituted aryl.
In one embodiment, R$_a$ and R$_b$ are both para-bromophenyl.

The term "alkyl", as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, where the one or more substituents are independently C$_1$-C$_{10}$ alkyl, C$_1$-C$_{10}$ alkoxy, C$_{6-10}$ aryl, C$_{3-9}$ heteroaryl, C$_{6-10}$ aryloxy, C$_1$-C$_{10}$ dialkylamino, or silyloxy in which the silicon has three substituents, where each substituent is independently hydrogen, C$_{1-10}$ alkyl, C$_{6-10}$ aryl or C$_{3-9}$ heteroaryl, or halogen. The alkyl group may contain one or more carbon-carbon double bonds, one or more carbon-carbon triple bonds, or a combination thereof. Examples of "alkyl" groups include methyl, ethyl, propyl, isopropyl, butyl, iso-butyl, sec-butyl, tert-butyl, pentyl, hexyl, heptyl, cyclopropyl, cyclobutyl, cyclopentyl, cyclohexyl, cycloheptyl, norbornyl, methoxymethyl, phenylmethyl, 4-bromophenylmethyl, 4-methoxyphenylmethyl, phenoxymethyl, dimethylaminomethyl, chloromethyl, 2-phenylethyl, (E)- and (Z)-2-phenylethenyl (Ph-CH=CH—), benzyloxymethyl, and the like, The term "halogen", as used herein, means chlorine (Cl), fluorine (F), iodine (I) or bromine (Br).

The term "alkoxy", as used herein, means "alkyl-O—", wherein "alkyl" is defined as above and O represents oxygen. Examples of "alkoxy" groups include methoxy, ethoxy, n-butoxy, tert-butoxy, and alkoxy groups in which the alkyl group is halogenated, such as alkoxy groups in which the alkyl group is fluorinated, including, for example, trifluoroethoxy and 1-trifluoromethyl-2-trifluoroethoxy.

The term "aryl", as used herein, unless otherwise indicated, includes an organic radical obtained from an aromatic hydrocarbon by removal of one hydrogen from a carbon of the aromatic hydrocarbon, wherein the radical is optionally substituted at between one and three carbons with a substituent at each carbon, where the substituent at each carbon is independently $C_1$-$C_{10}$ alkyl, $C_1$-$C_{10}$ alkoxy, $C_{6-10}$ aryl, $C_{6-10}$ aryloxy, $C_1$-$C_{10}$ dialkylamino, or halogen. Examples of "aryl" groups include phenyl, 1-naphthyl, 2-naphthyl, o-, m-, and p-methylphenyl, o-, m-, and p-methoxyphenyl, o-, m-, and p-diphenyl, o-, m-, and p-phenoxyphenyl, and o-, m-, and p-bromophenyl.

The term "heteroaryl", as used herein, unless otherwise indicated, includes an organic radical obtained from a heteroaromatic hydrocarbon having a heteroaromatic ring and one or two heteroatoms in the heteroaromatic ring by removal of one hydrogen from a carbon of the heteroaromatic hydrocarbon, wherein one or two heteroatoms are selected from the group consisting of O, N and S the radical is optionally substituted at between one and three carbons, at the one or two heteroatoms, or at a combination thereof with a substituent at each carbon, heteroatom or combination thereof, where the substituent is independently $C_1$-$C_{10}$ alkyl, $C_1$-$C_{10}$ alkoxy, $C_6$-$C_{10}$ aryl, $C_6$-$C_{10}$ aryloxy, $C_1$-$C_{10}$ dialkylamino, $C_1$-$C_{10}$ alkoxycarbonyl, or halogen. Examples of "heteroaryl" groups include 2-furyl, 3-furyl, 2-thiophenyl, 3-indolyl, 3-(N-t-butoxycarbonyl)-indolyl, 2-pyridyl, 3-pyridyl, 4-pyridyl, thienyl, thiazolyl, oxazolyl, 2-pyrrolyl and 2-(N-t-butoxycarbonyl)-pyrrolyl.

In one embodiment, the compound of formula A is the (R,R)-enantiomer. In another embodiment, the compound of formula A is the (S,S)-enantiomer.

In one embodiment, the compound of formula A is (R,R)-1. In another embodiment, the compound of formula A is (S,S)-1.

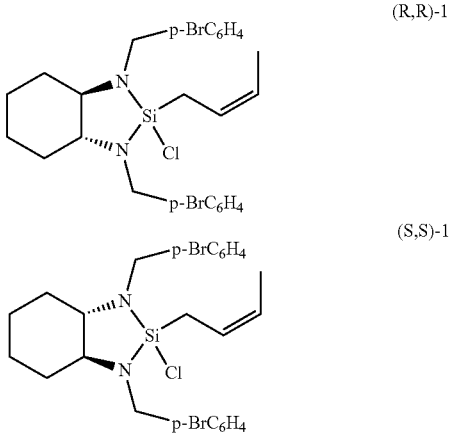

In one embodiment, the compound of formula A is (R,R)-2. In another embodiment, the compound of formula A is (S,S)-2.

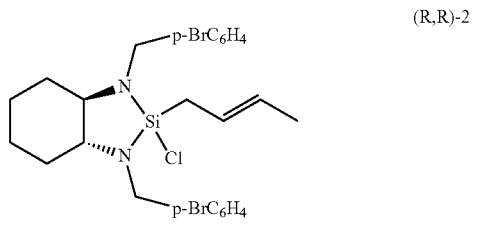

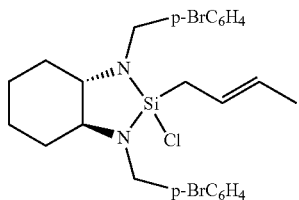

In one embodiment, the compound of formula A is (R,R)-13. In another embodiment, the compound of formula A is (S,S)-13.

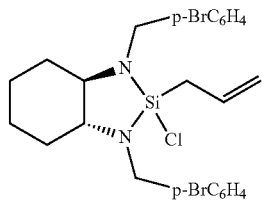

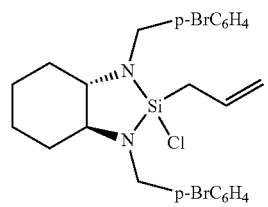

In one embodiment, the method provides for stereoselective allylation of an aldehyde. In another embodiment, the method provides for stereoselective crotylation of an aldehyde.

In one embodiment, the method provides for enantioselective allylation of an aldehyde. In another embodiment, the method provides for enantioselective crotylation of an aldehyde.

In one embodiment, the method provides for enantioenriched allylation of an aldehyde. In another embodiment, the method provides for enantioenriched crotylation of an aldehyde.

In one embodiment, the crotylated product is generated with >80% enantiomeric excess. In one embodiment, the crotylated product is generated with >90% enantiomeric excess. In another embodiment, the crotylated product is generated with >95% enantiomeric excess.

In one embodiment, the allylated product is generated with >80% enantiomeric excess. In one embodiment, the allylated product is generated with >90% enantiomeric excess. In another embodiment, the allylated product is generated with >95% enantiomeric excess.

In one embodiment, the method provides for diastereoselective crotylation of the aldehyde. In another embodiment, the method provides for diastereoenriched crotylation of the aldehyde. In one embodiment, the crotylation proceeds to generate the crotylated product with >10:1 diastereoselectivity. In still another embodiment, the crotylation proceeds to generate the crotylated product with >20:1 diastereoselectivity. In still another embodiment, the crotylation proceeds to generate the crotylated product with >30:1 diastereoselectivity. In still another embodiment, the crotylation proceeds to generate the crotylated product with >40:1 diastereoselectivity. In still another embodiment, the crotylation proceeds to generate the crotylated product with >45:1 diastereoselectivity.

In one embodiment, the method provides for diastereoselective allylation of the aldehyde. In another embodiment, the method provides for diastereoenriched allylation of the aldehyde. In one embodiment, the allylation proceeds to generate the allylated product with >10:1 diastereoselectivity. In still another embodiment, the allylation proceeds to generate the allylated product with >20:1 diastereoselectivity. In still another embodiment, the allylation proceeds to generate the allylated product with >30:1 diastereoselectivity. In still another embodiment, the allylation proceeds to generate the allylated product with >40:1 diastereoselectivity. In still another embodiment, the allylation proceeds to generate the allylated product with >45:1 diastereoselectivity.

In one embodiment, the stereoselective allylation or crotylation provides productive reactions with aldehyde substrates. In one embodiment, the allylation or crotylation reaction proceeds to give >70% yield of the allylation or crotylation product. In one embodiment, the allylation or crotylation reaction proceeds to give >80% yield of the allylation or crotylation product. In one embodiment, the allylation or crotylation reaction proceeds to give >85% yield of the allylation or crotylation product. In one embodiment, the allylation or crotylation reaction proceeds to give >90% yield of the allylation or crotylation product. In another embodiment, the allylation or crotylation reaction proceeds to give >95% yield of the allylation or crotylation product.

In one embodiment, the invention provides productive reactions with aldehyde substrates that are otherwise unreactive toward allylation or crotylation using compounds of formula A. In another embodiment, the invention enables the allylation or crotylation of aldehydes that are unreactive in the absence of scandium triflate. In still another embodiment, the aldehyde does not react with the compound of formula A in the absence of scandium triflate.

In one embodiment, the aldehyde is achiral. In another embodiment, the aldehyde substrates contain at least one stereogenic center. In another embodiment, the aldehyde substrates are deactivated.

In one embodiment, the allylation or crotylation reaction occurs at ambient temperature. In another embodiment, the allylation or crotylation reaction occurs at 0° C.

In another embodiment, the Lewis acid is selected from the group consisting of aluminum chloride, yttrium triflate, and scandium triflate. In yet another embodiment, the Lewis acid is scandium triflate.

In one embodiment, the Lewis acid is $Sc(OTf)_3$.

In one embodiment, the reaction proceeds with a catalytic amount of Lewis acid. In one embodiment, the amount of Lewis acid is <10 mol %. In one embodiment, the amount of Lewis acid is about 5 mol %. In still another embodiment, the amount of Lewis acid is about 2 mol %.

In another aspect, the invention relates to a pre-mixed silane-Lewis acid system or composition for use in stereoselective aldehyde allylation or crotylation, wherein the silane is a silane of formula A.

In one embodiment, the pre-mixed silane-Lewis acid system comprises an allylsilane. In another embodiment, the pre-mixed silane-Lewis acid system comprises a crotylsilane.

In one embodiment, the invention comprises a compound of formula A and a Lewis acid.

In one embodiment, the compound of formula A is (R,R)-1. In another embodiment, the compound of formula A is (S,S)-1.

In one embodiment, the compound of formula A is (R,R)-2. In another embodiment, the compound of formula A is (S,S)-2.

In one embodiment, the compound of formula A is (R,R)-13. In another embodiment, the compound of formula A is (S,S)-13.

In one embodiment, the compound of formula A is (S,S)-1 and the Lewis acid is $Sc(OTf)_3$. In another embodiment, the compound of formula A is (R,R)-1 and the Lewis acid is $Sc(OTf)_3$. In yet another embodiment, the compound of formula A is (S,S)-2 and the Lewis acid is $Sc(OTf)_3$. In still another embodiment, the compound of formula A is (R,R)-2 and the Lewis acid is $Sc(OTf)_3$.

In one embodiment, the compound of formula A is (S,S)-13 and the Lewis acid is $Sc(OTf)_3$. In another embodiment, the compound of formula A is (R,R)-13 and the Lewis acid is $Sc(OTf)_3$.

In one embodiment, the Lewis acid is present in about 10 mol % relative to the amount of aldehyde. In another embodiment, the Lewis acid is present in about 5 mol % relative to the amount of aldehyde. In still another embodiment, the Lewis acid is present in about 4 mol % relative to the amount of aldehyde. In yet another embodiment, the Lewis acid is present in about 2 mol % relative to the amount of aldehyde.

In one embodiment, the compound of formula A and the Lewis acid are pre-mixed prior to reaction with the aldehyde. In another embodiment, the compound of formula A and the Lewis acid are present in about a 50:1 molar ratio (compound of formula A: Lewis acid). In another embodiment, the molar ratio is about 30:1. In yet another embodiment, the molar ratio is about 25:1. In still another embodiment, the molar ration is about 20:1. In still another embodiment, the molar ratio is about 15:1. In still another embodiment, the molar ratio is about 10:1.

In one embodiment, the composition is pre-mixed and stored at ambient temperature prior to reaction with the aldehyde.

In another embodiment, the pre-mixed composition is stored under low humidity conditions. In one embodiment, the low humidity conditions comprise storage under an inert gas. In another embodiment, the low humidity conditions comprise storage in a dessicator or glove box.

In yet another embodiment, the pre-mixed silane-Lewis acid system provides for a practical method of stereoselective allylation or crotylation. In still another embodiment, the pre-mixed silane-Lewis acid system can be stored at ambient temperature prior to use. In still another embodiment, the pre-mixed silane-Lewis acid system can be stored at 0° C. prior to use. In still another embodiment, the pre-mixed silane-Lewis acid system can be used at ambient temperature. In still another embodiment, the pre-mixed silane-Lewis acid system can be used at 0° C. In yet another embodiment, the silane and Lewis acid of the pre-mixed silane-Lewis acid system each exist as crystalline solids.

In one embodiment, the invention provides for stereoselective allylation or crotylation of a broad scope of aldehydes containing various functional groups and/or stereogenic centers.

Due to the direct relevance of the products to important classes of natural products, the development of diastereo- and enantioselective aldehyde allylation and crotylation reactions has been the subject of an enormous amount of effort over the last three decades. The first "practical" solution to diastereo- and enantioselective aldehyde crotylation reactions was advanced by Brown et al in 1986 ((a) Brown, H. C.; Bhat, K. S. *J. Am. Chem. Soc.* 1986, 108, 293. (b) Brown, H. C.; Bhat, K. S. *J. Am. Chem. Soc.* 1986, 108, 5919; each of which are hereby incorporated by reference in their entirety), and this chiral crotylborane methodology remains the most widely employed to the present day. However, the Brown method suffers from significant practical liabilities. For example, the preparation of the requisite cis- or trans-crotylborane reagent entails the carefully (low and variable) temperature-controlled metallation of either cis- or trans-2-butene with n-BuLi and KOt-Bu, addition of the resulting crotylpotassium species to either (+)- or (−)-(ipc)$_2$BOMe, and then addition of BF$_3$.OEt$_2$ and the aldehyde. In addition, the work-up procedure entails the oxidative cleavage of the borane from the product alcohol, which has the side effect of generating two equivalents of isopinocampheol that can, and often does, render product isolation significantly more difficult.

Because of these shortcomings, efforts to supplant the Brown method as the method of choice have continued for well over a decade to the present day, with only limited success. See, for example, (a) Roush, W. R.; Ando, K; Powers, D. B.; Palkowitz, A. D.; Halternan, R. L. *J. Am. Chem. Soc.* 1990, 112, 6339; (b) Garcia, J.; Kim, B. M.; Masamune, S. *J. Org. Chem.* 1987, 52, 4831; (c) Hafner, A.; Duthlaer, R. O.; Marti, R.; Rihs, G.; Rothe-Streit, P.; Schwarzenbach, F. *J. Am. Chem. Soc.* 1992, 114, 2321; (d) Jain, N. F.; Takenaka, N.; Panek, J. S. *J. Am. Chem. Soc.* 1996, 118, 12475; (e) Denmark, S. E.; Fu, J. *J. Am. Chem. Soc.* 2001, 123, 948; (f) Lachance, H.; Lu, X.; Gravel, M.; Hall, D. G. *J. Am. Chem. Soc.* 2003, 125, 10160; (g) Burgos, C. H.; Canales, E.; Matos, K.; Soderquist, J. A. *J. Am. Chem. Soc.* 2005, 127, 8044; and (h) Kim, I. S.; Han, S. B.; Krische, M. J. *J. Am. Chem. Soc.* 2009, 131, 2514. Each of these references are also hereby incorporated by reference into this application in their entireties.

Asymmetric allylation reactions have been described, for example, in Roush, W. R. in *Comprehensive Organic Synthesis* (Trost, B. M.; Fleming, I., Eds.), Pergamon. Press: New York, 1991, Vol. 2, pp. 1-53. See also, (a) Denmark, S. E. and Almstead, N. G. in *Modern Carbonyl Chemistry* (Otera, J., Ed.), Wiley-VCH, Weinheim, 2000, ch. 10; (b) Roush, W. R. in *Modern Carbonyl Chemistry* (Otera, J., Ed.), Wiley-VCH, Weinheim, 2000, ch. 11; (c) Herold, T.; Hoffmann, R. W. *Angew. Chem.* 1978, 90, 822; *Angew. Chem. Int. Ed. Eng.* 1978, 17, 768; (d) Brown, H. C.; Jadhav, P. K. *J. Am. Chem. Soc.* 1983, 105, 2092; (e) Jadhav, P. K.; Bhat, K. S.; Perumal, P. T.; Brown, H. C. *J. Org. Chem.* 1986, 51, 432; (f) Racherla, U.S.; Brown, H. C. *J. Org. Chem.* 1991, 56, 401; (g) Roush, W. R.; Walts, A. E.; Hoong, L. K. *J. Am. Chem. Soc.* 1985, 107, 8186; (h) Roush, W. R.; Banfi, W. L. *J. Am. Chem. Soc.* 1988, 110, 3979; (i) Reetz, M. T.; Zierke, T. Chem. Ind. 1988, 663; (j) Short, R. P.; Masamune, S. *J. Am. Chem. Soc.* 1989, 111, 1892; (k) Corey, E. J.; Yu, C.-M.; Kim, S. S. *J. Am. Chem. Soc.* 1989, 111, 5495; (l) Faller, J. W.; Linebarrier, D. L. *J. Am. Chem. Soc.* 1989, 111, 1937; and (m) Hafner, A.; Duthaler, R. O.; Marti, R.; Rihs, G.; Rothe-P. Streit; Schwarzenbach, F. *J. Am. Chem. Soc.* 1992, 114, 2321. Each of these references are also hereby incorporated by reference into this application in their entireties.

Silane reagents have been described, for example in U.S. Pat. No. 7,534,905; U.S. patent application Ser. No. 11/810,920; Hackman, B. M., Lombardi, P. J., Leighton, J. L. *Org. Leu.* 2004, 6, 4375; and Kubota, K., Leighton, J. L. *Angew. Chem. Int. Ed.* 2003, 42, 946, each of which are hereby incorporated by reference in their entirety.

Crotylsilanes 1 and 2 are crystalline solids that may be prepared in bulk and stored, and that react with aldehydes at 0° C. over the course of ~20 h to consistently provide enantioselectivities (93-99% ee) among the highest ever recorded for aldehyde crotylation reactions (Scheme 1; see also, Hackman, B. M.; Lombardi, P. J.; Leighton, J. L. *Org. Lett.* 2004, 6, 4375; hereby incorporated by reference in its entirety).

Despite these advantages, the reagents suffer from one significant drawback: the substrate scope is limited, with aromatic, unsaturated, and sterically hindered aliphatic aldehydes all giving moderate to low yields, or even, in some cases, no product at all. For example, reagents 1 and 2 completely fail to react productively or at all with 3, α-methylcinnamaldehyde, and 4.

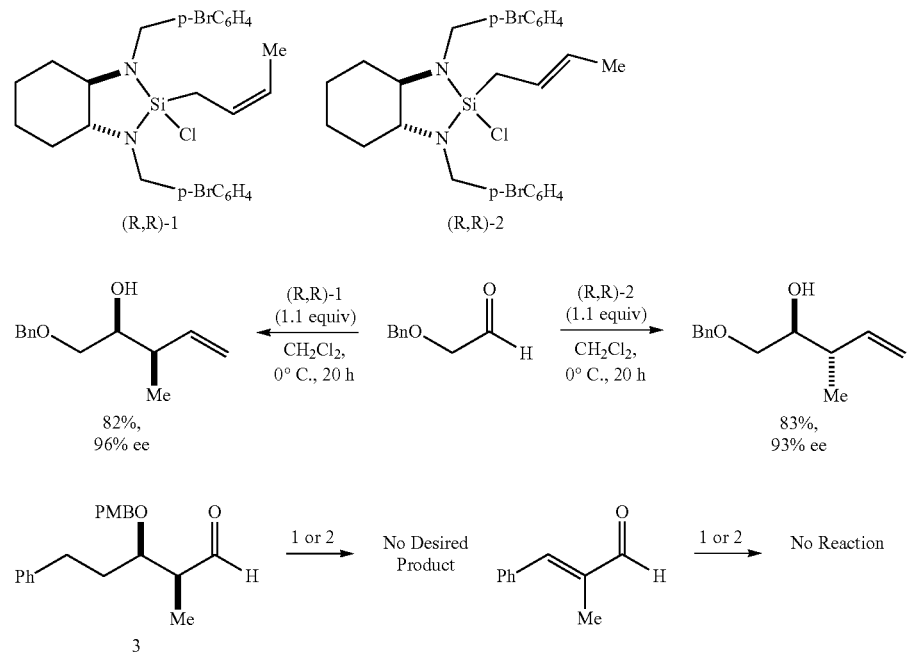

Scheme 1

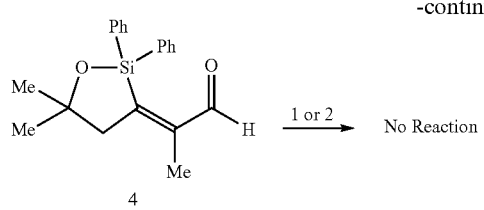

4

Because the successful crotylation of aldehydes such as 4 is relevant to several synthetic projects this methodology was revisited in an attempt to solve the reactivity problem. Two relevant pieces of information were considered: 1) protonation of some aminochlorosilane Lewis acids (by way of reaction with protic nucleophiles, which displace the chloride and generate an equivalent of HCl) leads to an increase in their reactivity ((a) Berger, R.; Duff, K.; Leighton, J. L. *J. Am. Chem. Soc.* 2004, 126, 5686; (b) Burns, N. Z.; Hackman, B. M.; Ng, P. Y.; Powelson, I. A.; Leighton, J. L. *Angew. Chem. Int. Ed.* 2006, 45, 3811); and 2) Lewis acids may be used to catalyze the reactions of allylboronates with aldehydes by binding or protonating one of the boronate oxygen atoms (Sc(OTf)$_3$ is particularly effective; see (a) Kennedy, J. W. J.; Hall, D. G. *J. Am. Chem. Soc.* 2002, 124, 11586; and (b) Ishiyama, T.; Ahiko, T.; Miyaura, N. *J. Am. Chem. Soc.* 2002, 124, 12414) and Brønsted acids ((a) Yu, S. H.; Ferguson, M. J.; McDonald, R.; Hall, D. G. *J. Am. Chem. Soc.* 2005, 127, 12808; (b) Rauniyar, V.; Hall, D. G. *Angew. Chem. Int. Ed.* 2006, 45, 2426; (c) Rauniyar, V.; Zhai, H.; Hall, D. G. *J. Am. Chem. Soc.* 2008, 130, 8481; and (d) Jain, P.; Antilla, J. C. *J. Am. Chem. Soc.* 2010, 132, 11884). Each of these references are also hereby incorporated by reference into this application in their entireties.

Figure 2A:
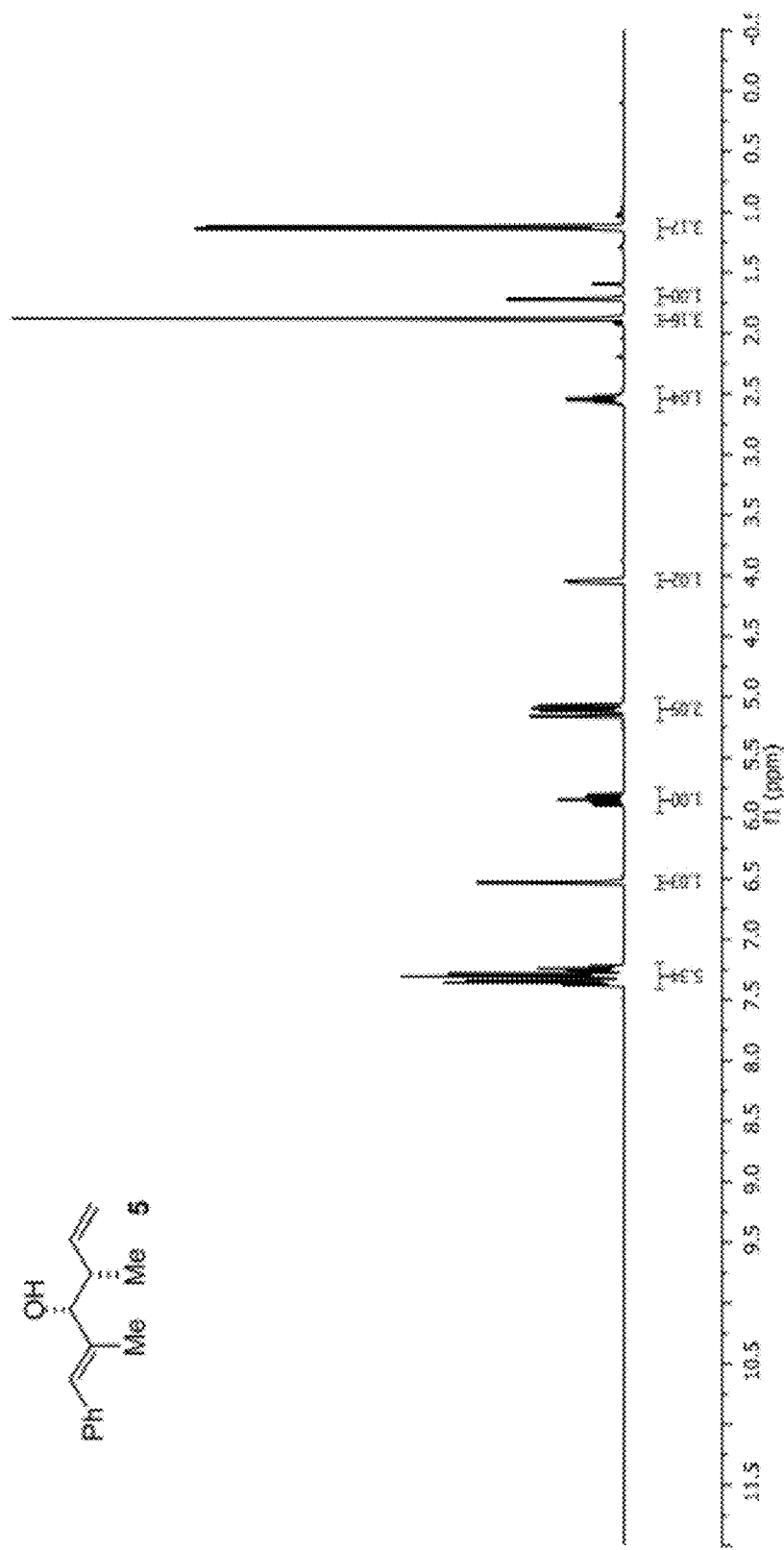
FIG. 2. The (A) $^1$H NMR spectrum and (B) $^{13}$C NMR spectrum of (3R,4S)-5 in CDCl$_3$.
Figure 2B:
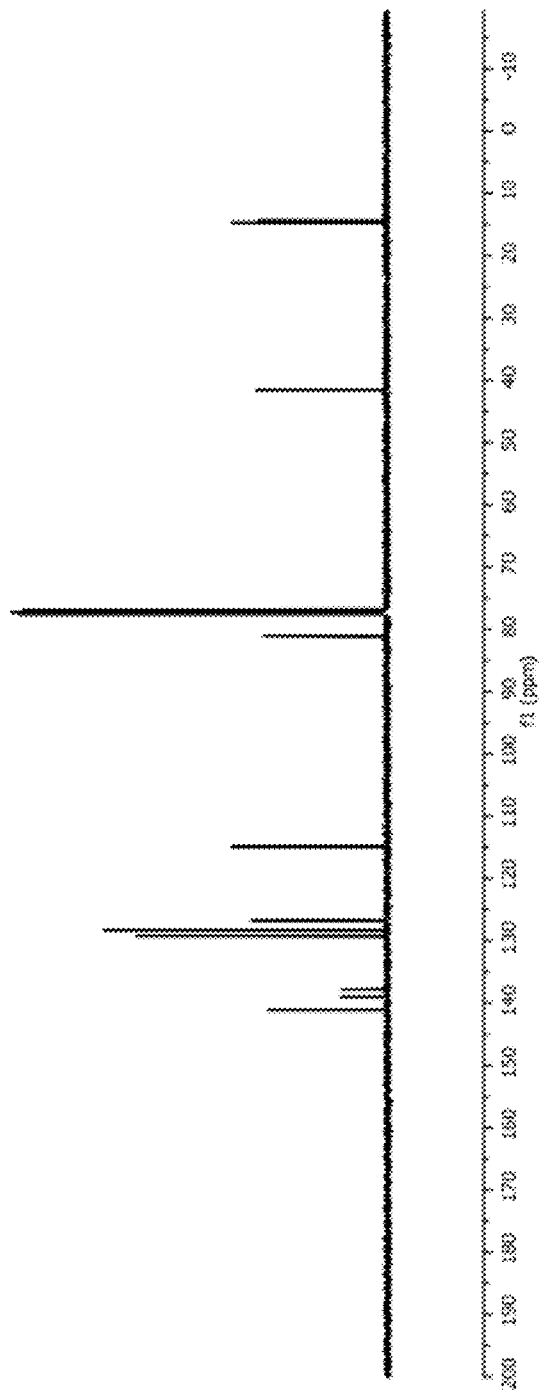
Figure 3A:
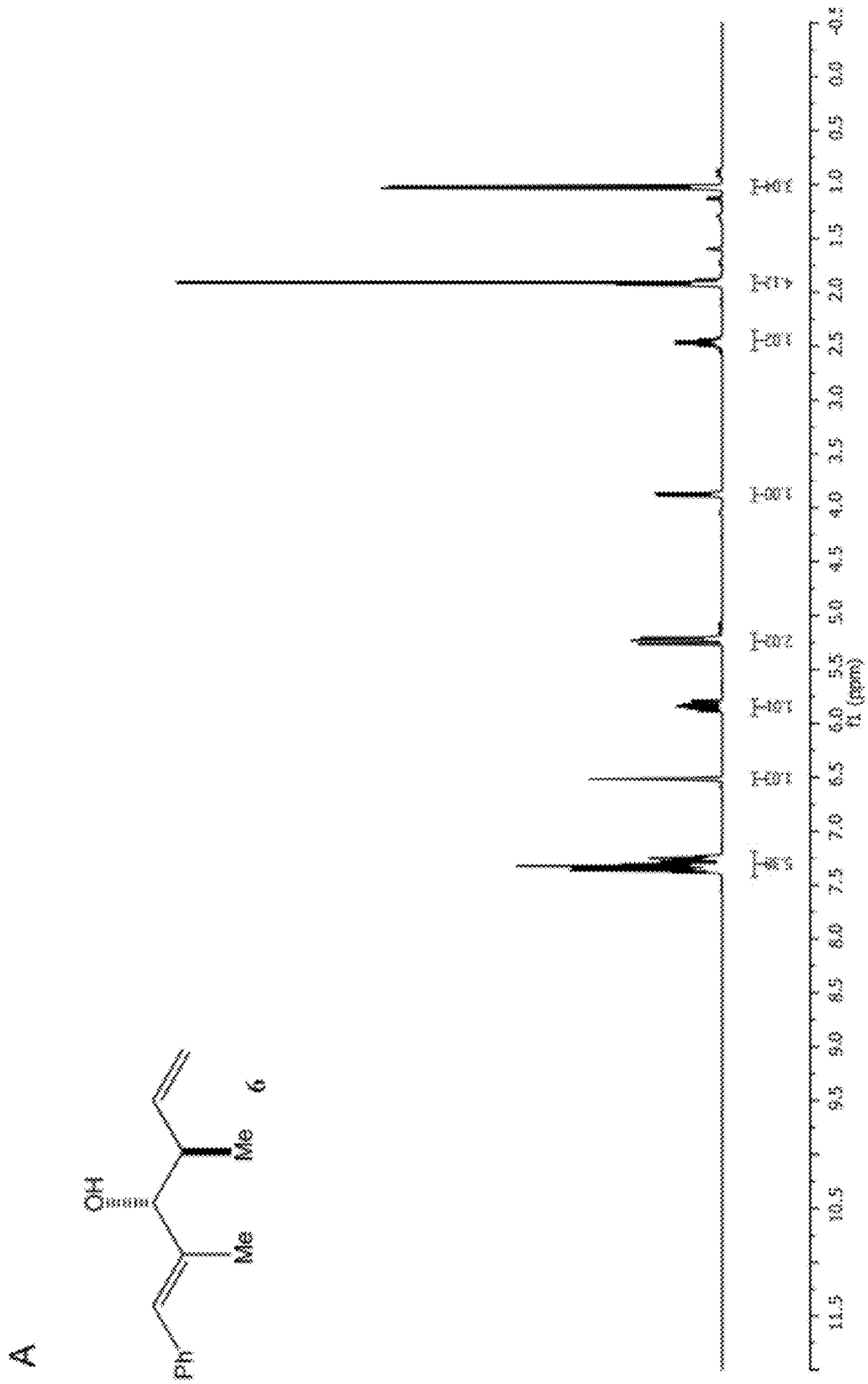
FIG. 3. The (A) $^1$H NMR spectrum and (B) $^{13}$C NMR spectrum of (3R,4R)-6 in CDCl$_3$.
Figure 3B:
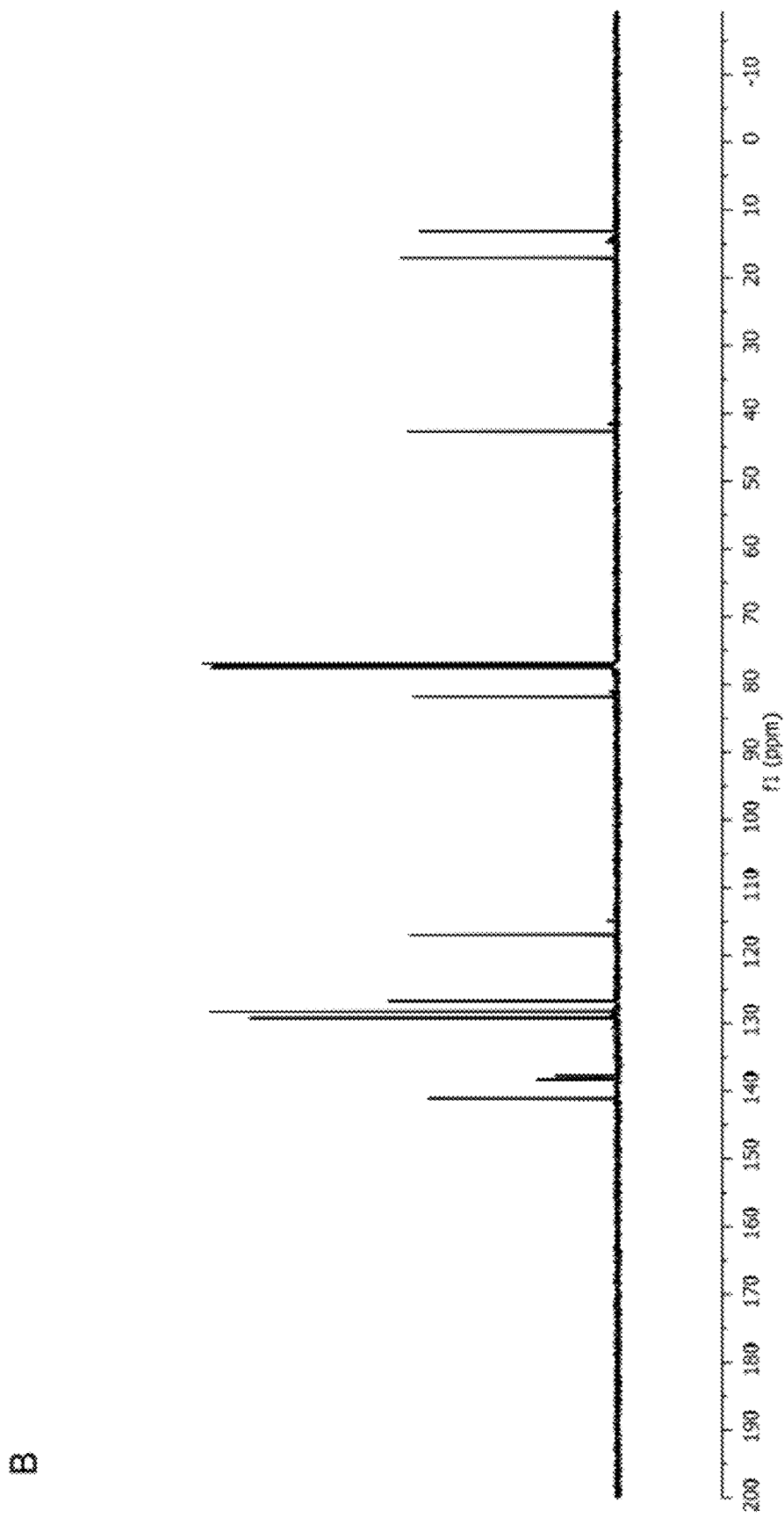
Figure 4A:
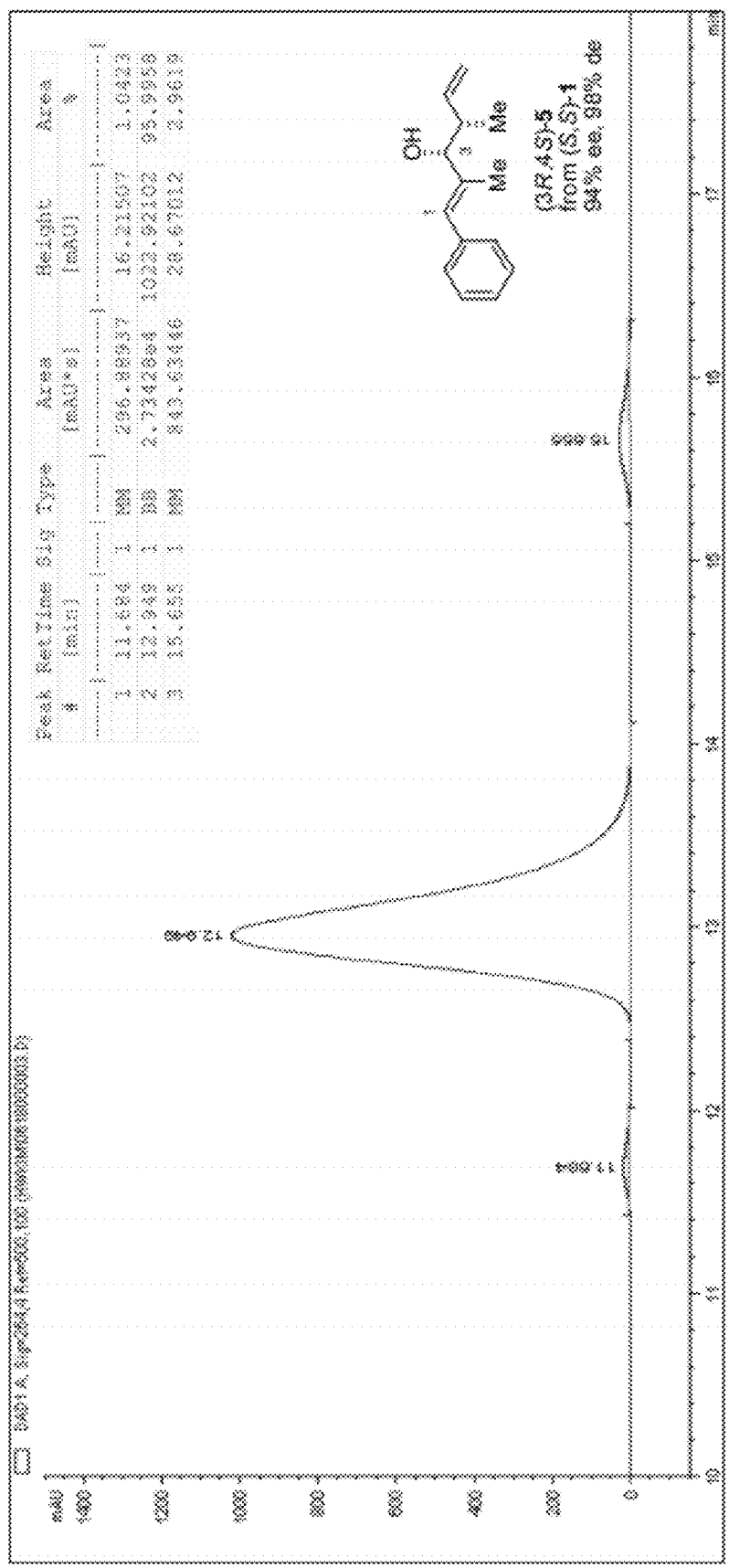
FIG. 4. The HPLC traces of (A) (3R,4S)-5 prepared from (S,S)-1 and (B) (3R,4R)-6 prepared from (S,S)-2 from a Chiracel OD column, 3% i-PrOH in hexanes, 1 mL/min.
Figure 4B:
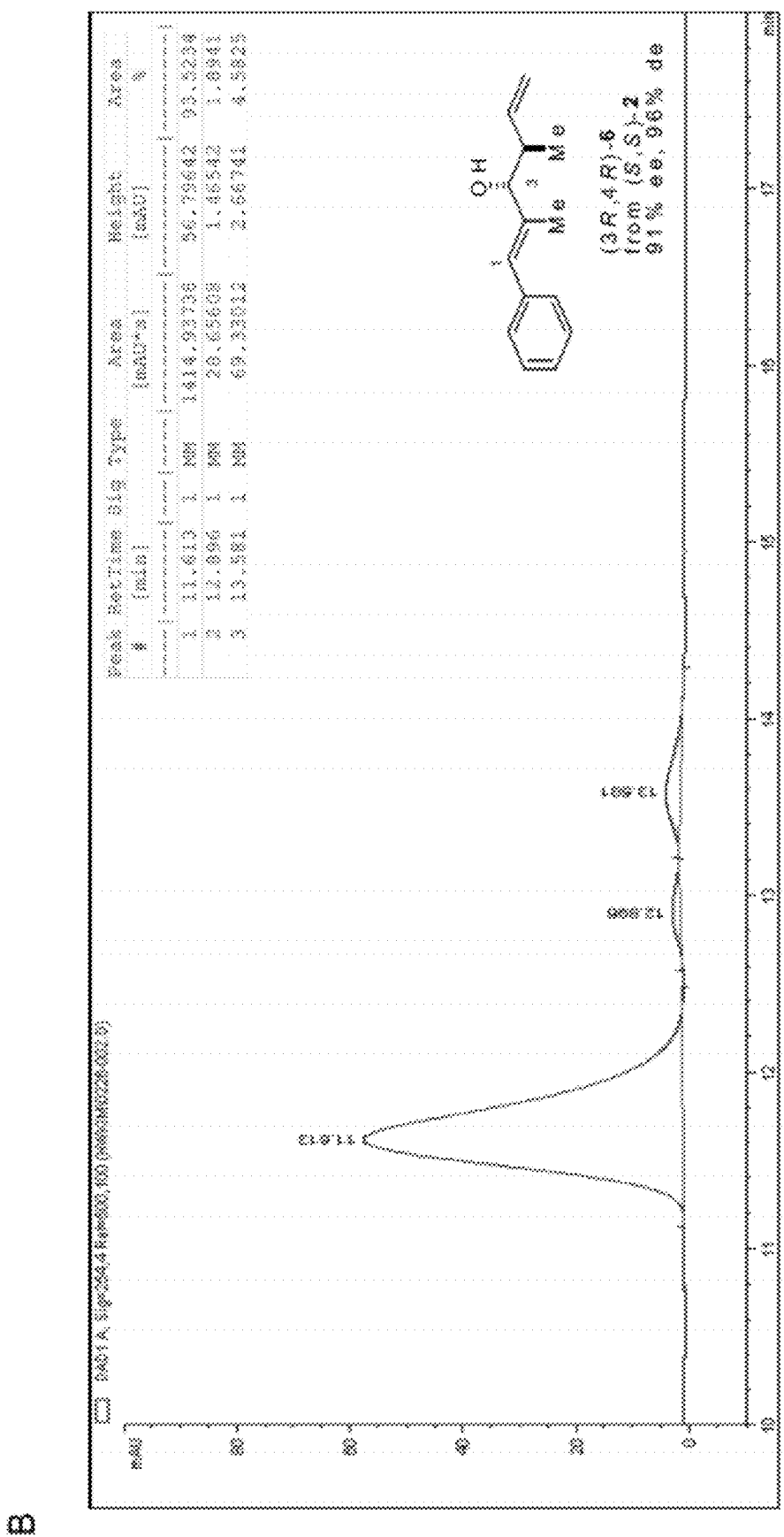
Figure 5A:
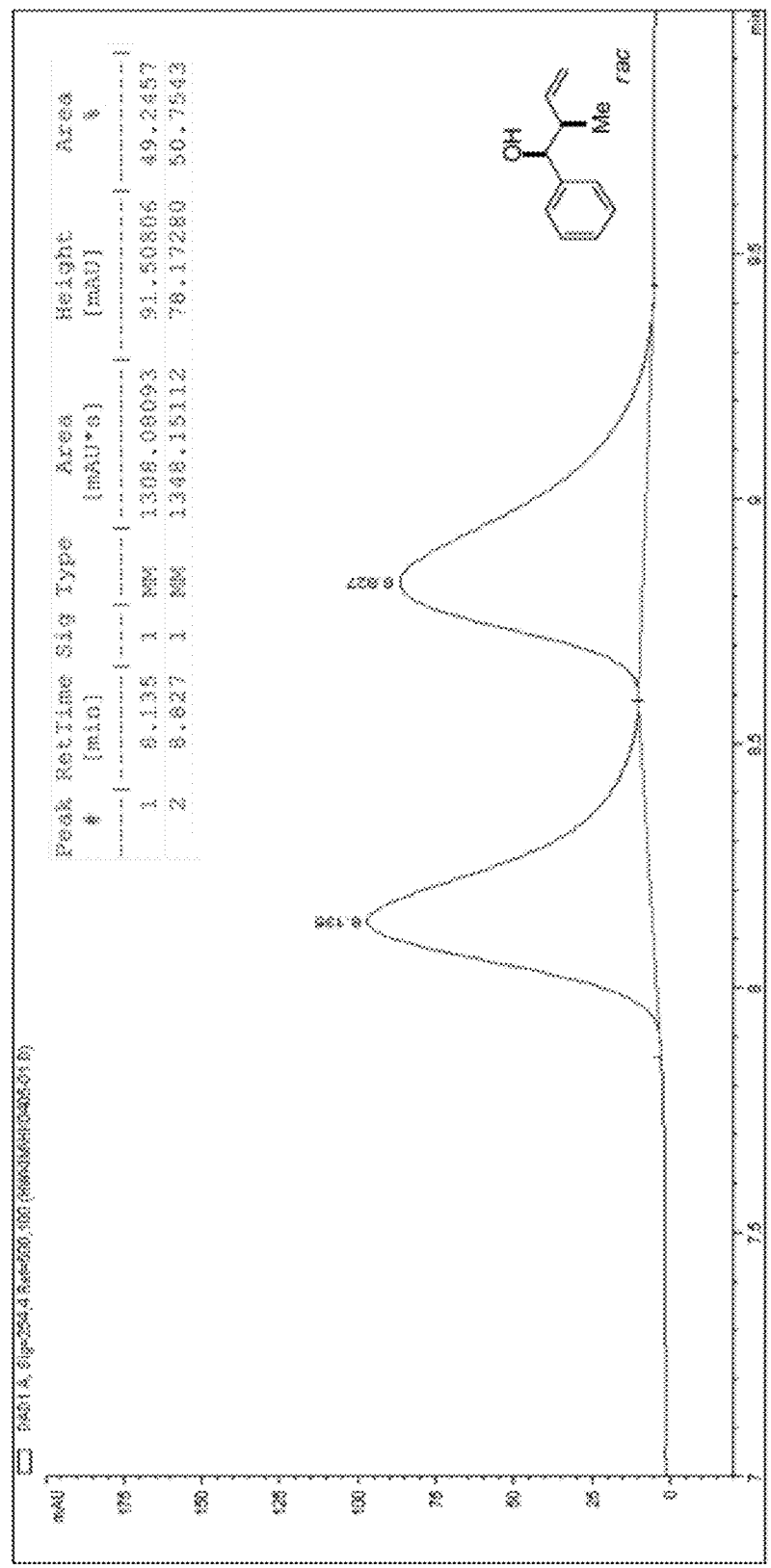
FIG. 5. The HPLC traces of (A) racemic crotylation of benzaldehyde using cis-crotylboronic acid pinacol ester and (B) crotylation of benzaldehyde using (S,S)-1 and Sc(OTf)$_3$ from a Chiracel OD column, 5% i-PrOH in hexanes, 1 mL/min.
Figure 5B:
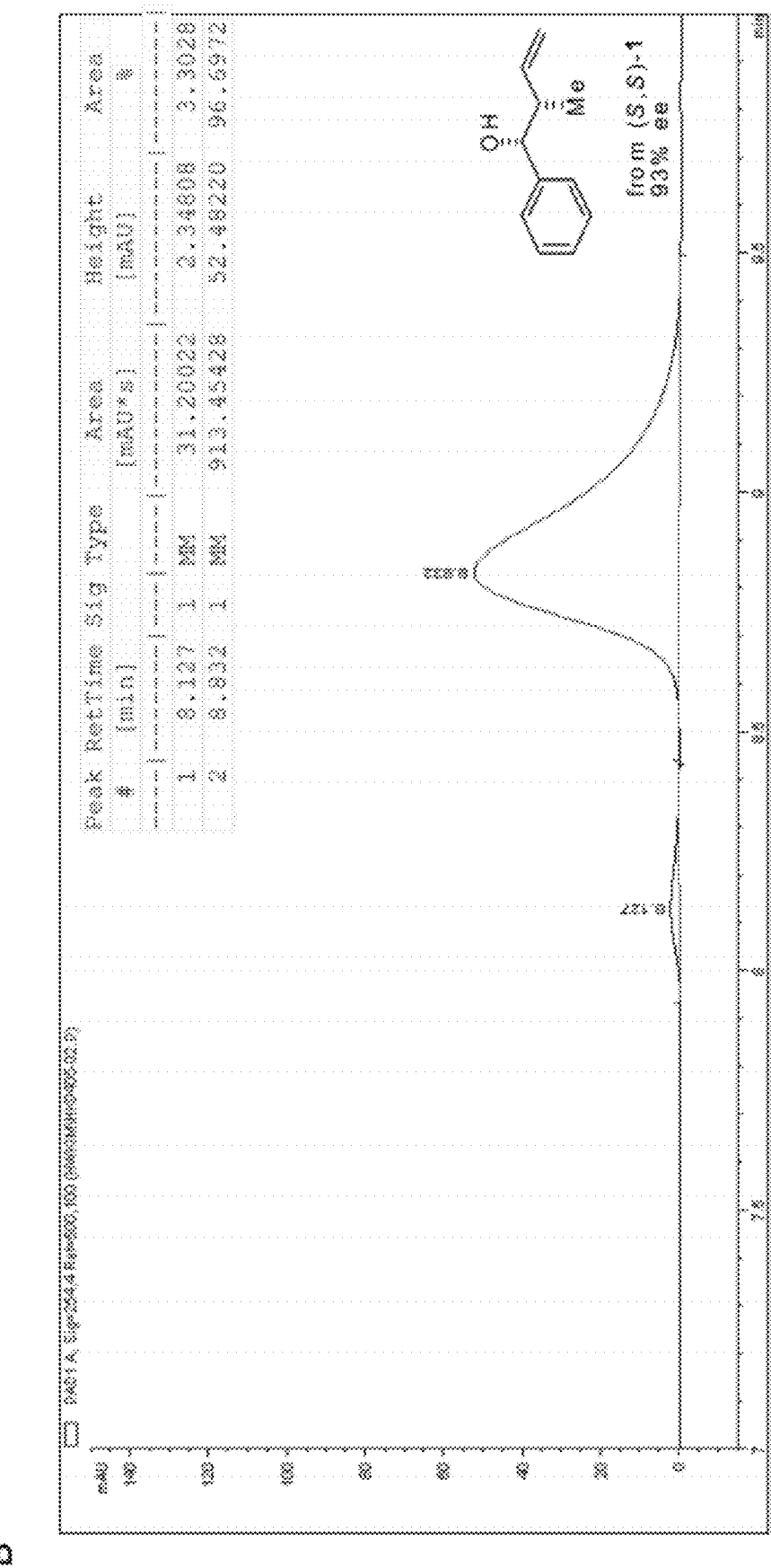
Figure 6A:
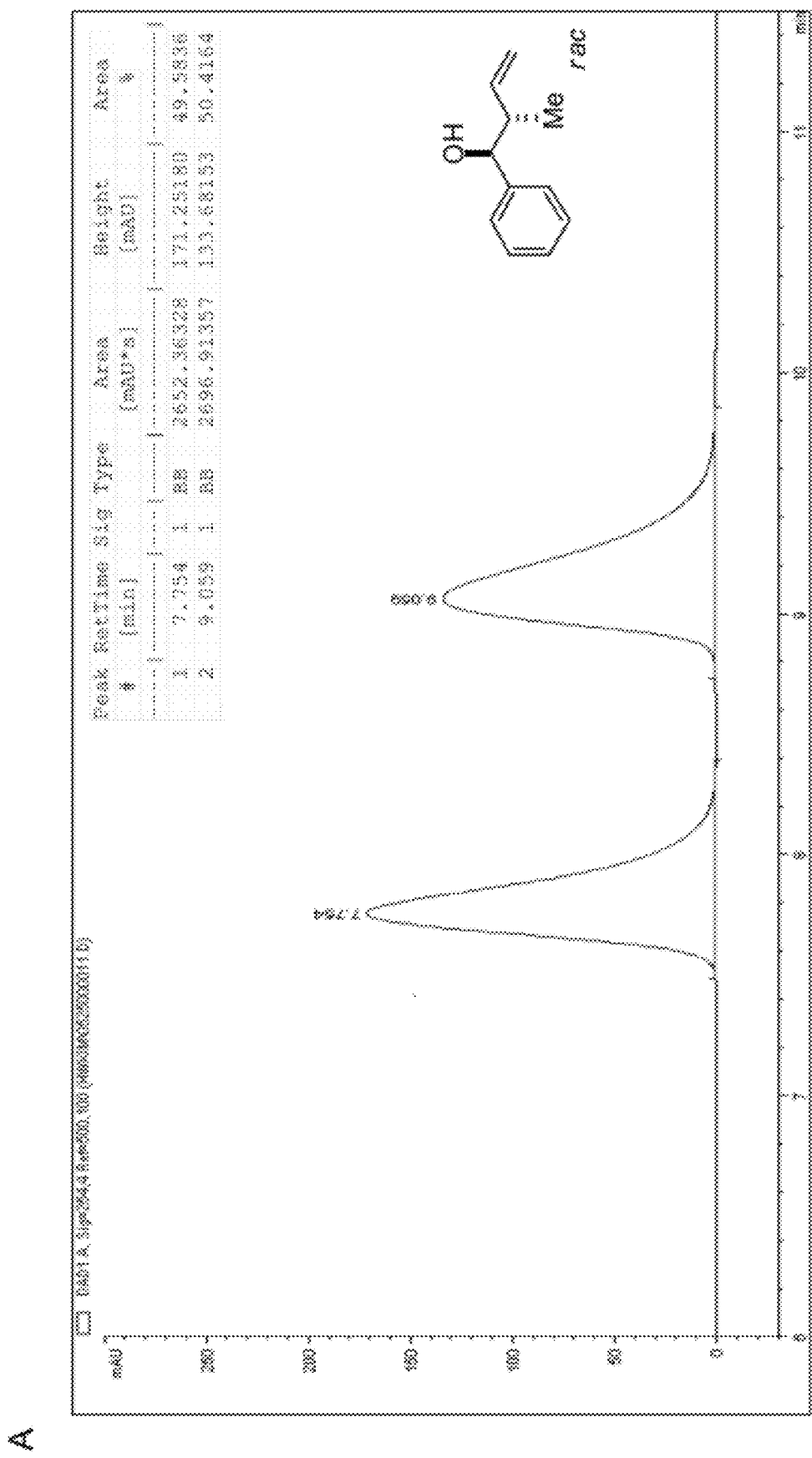
FIG. 6. The HPLC traces of (A) racemic crotylation of benzaldehyde using trans-crotylboronic acid pinacol ester and (B) crotylation of benzaldehyde using (S,S)-2 and Sc(OTf)$_3$ from a Chiracel OD column, 5% i-PrOH in hexanes, 1 mL/min.
Figure 6B:
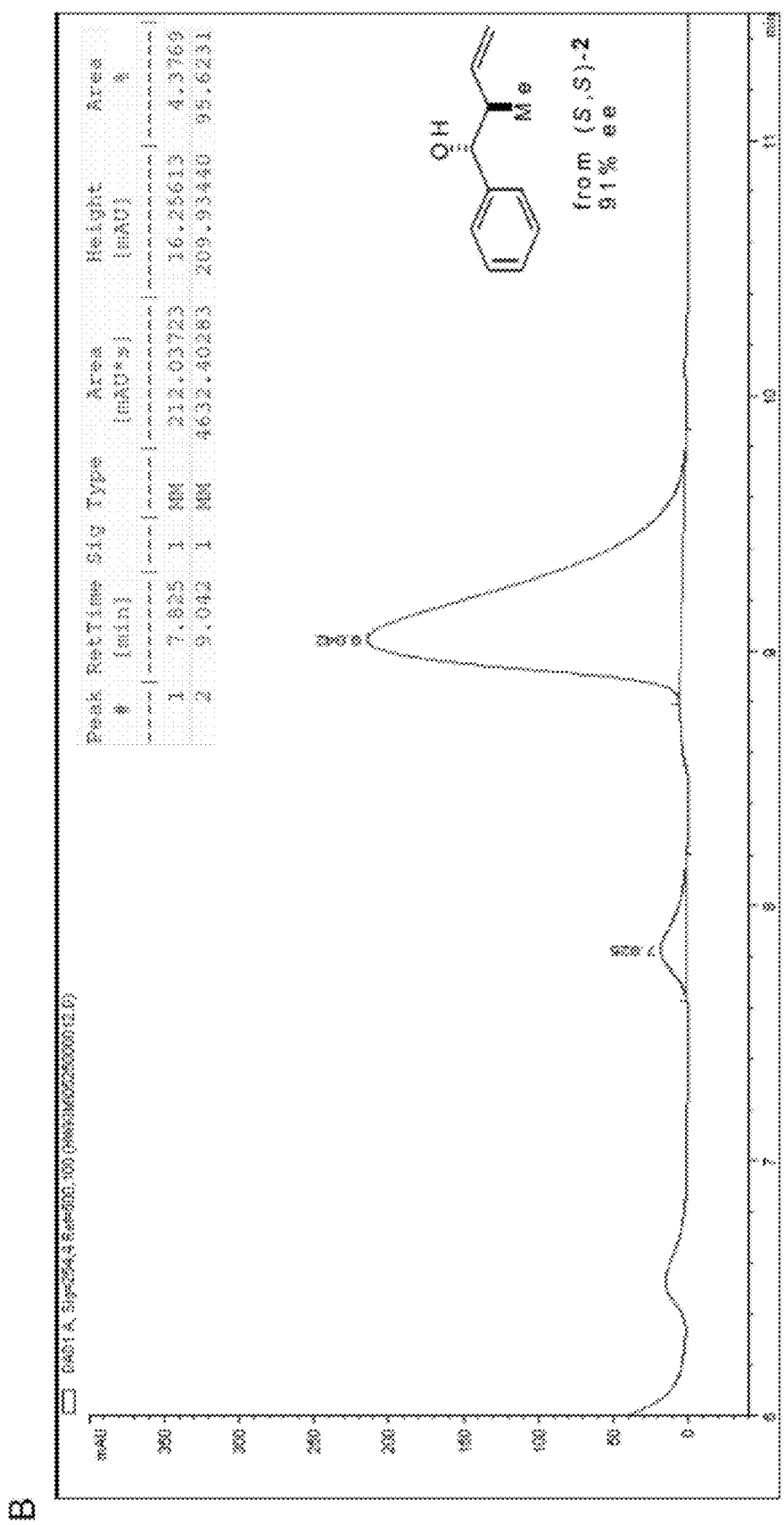
Figure 7A:
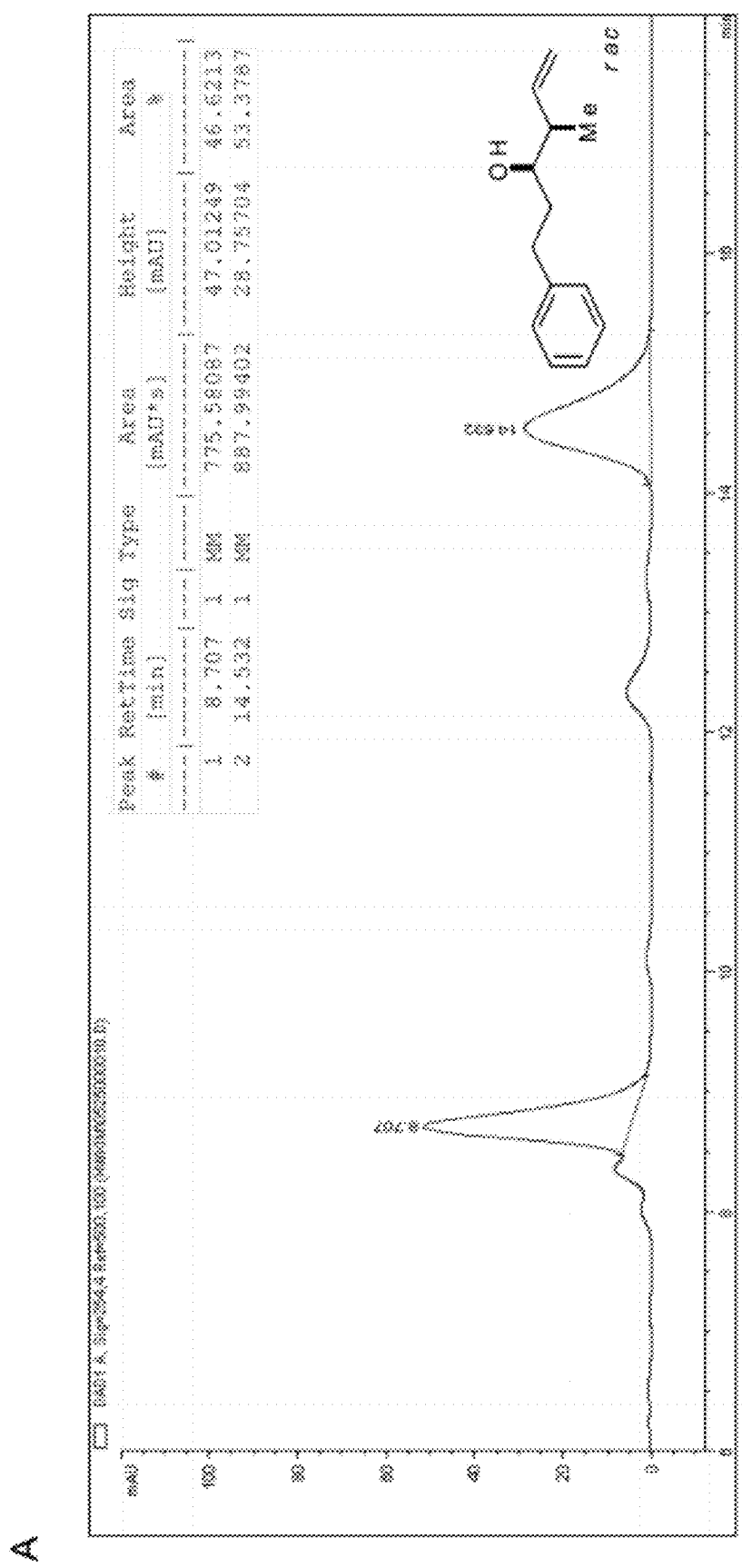
FIG. 7. The HPLC traces of (A) racemic crotylation of 3-phenylpropanal using cis-crotylboronic acid pinacol ester and (B) crotylation of 3-phenylpropanal using (S,S)-1 and Sc(OTf)$_3$ from a Chiracel OD column, 5% i-PrOH in hexanes, 1 mL/min.
Figure 7B:
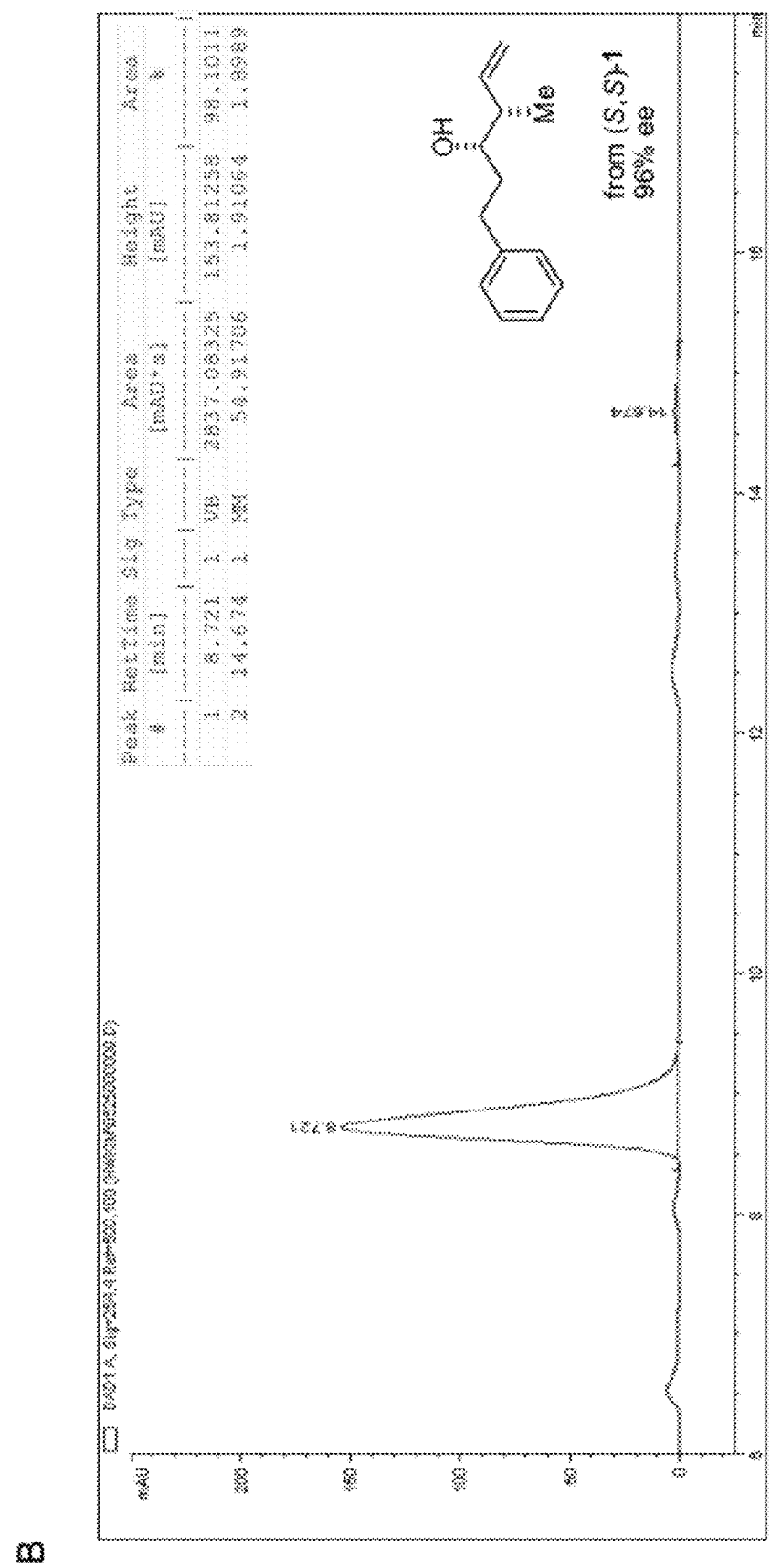
Figure 8A:
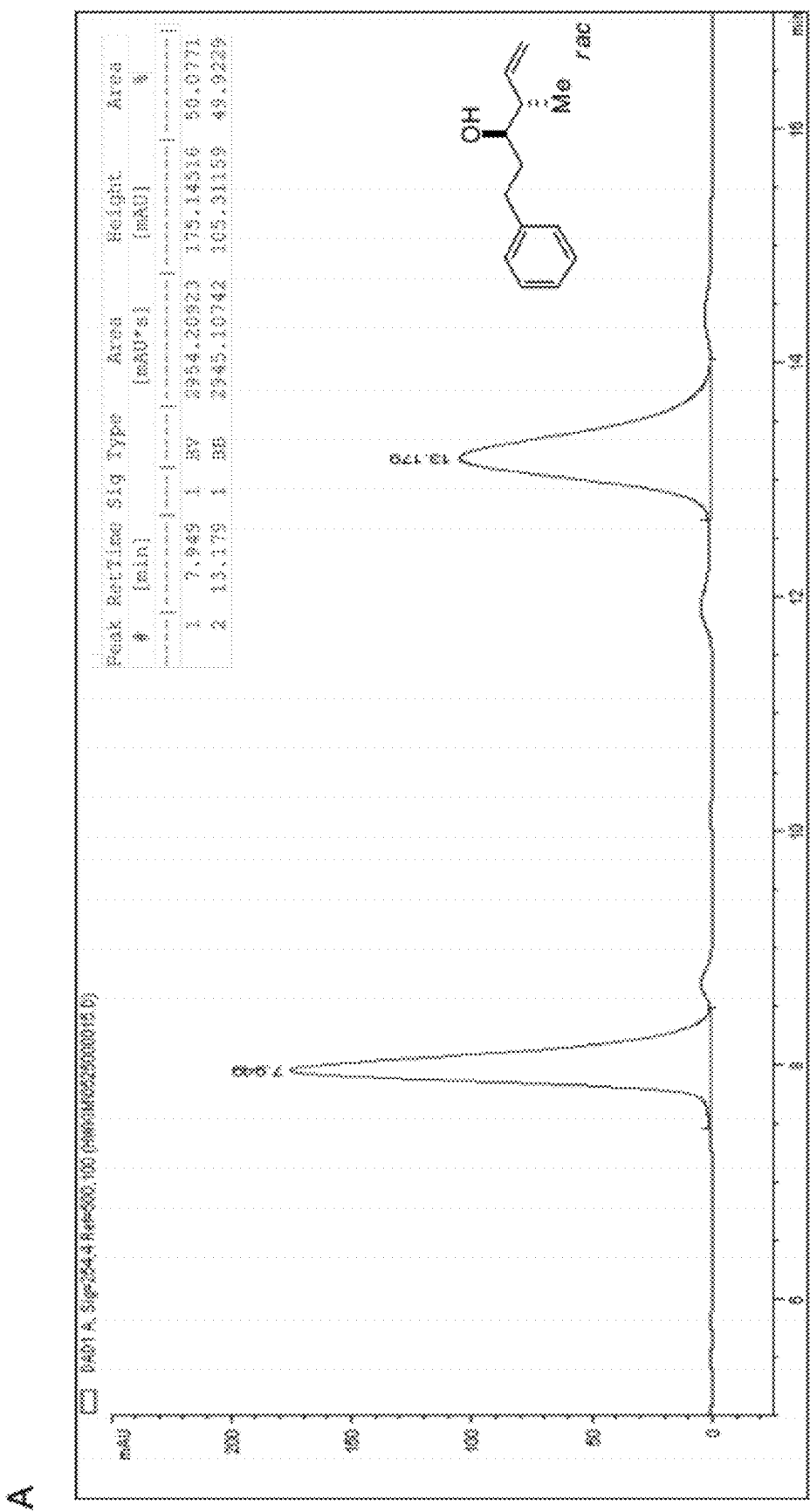
FIG. 8. The HPLC traces of (A) racemic crotylation of 3-phenylpropanal using trans-crotylboronic acid pinacol ester and (B) crotylation of 3-phenylpropanal using (S,S)-2 and Sc(OTf)$_3$ from a Chiracel OD column, 5% i-PrOH in hexanes, 1 mL/min.
Figure 8B:
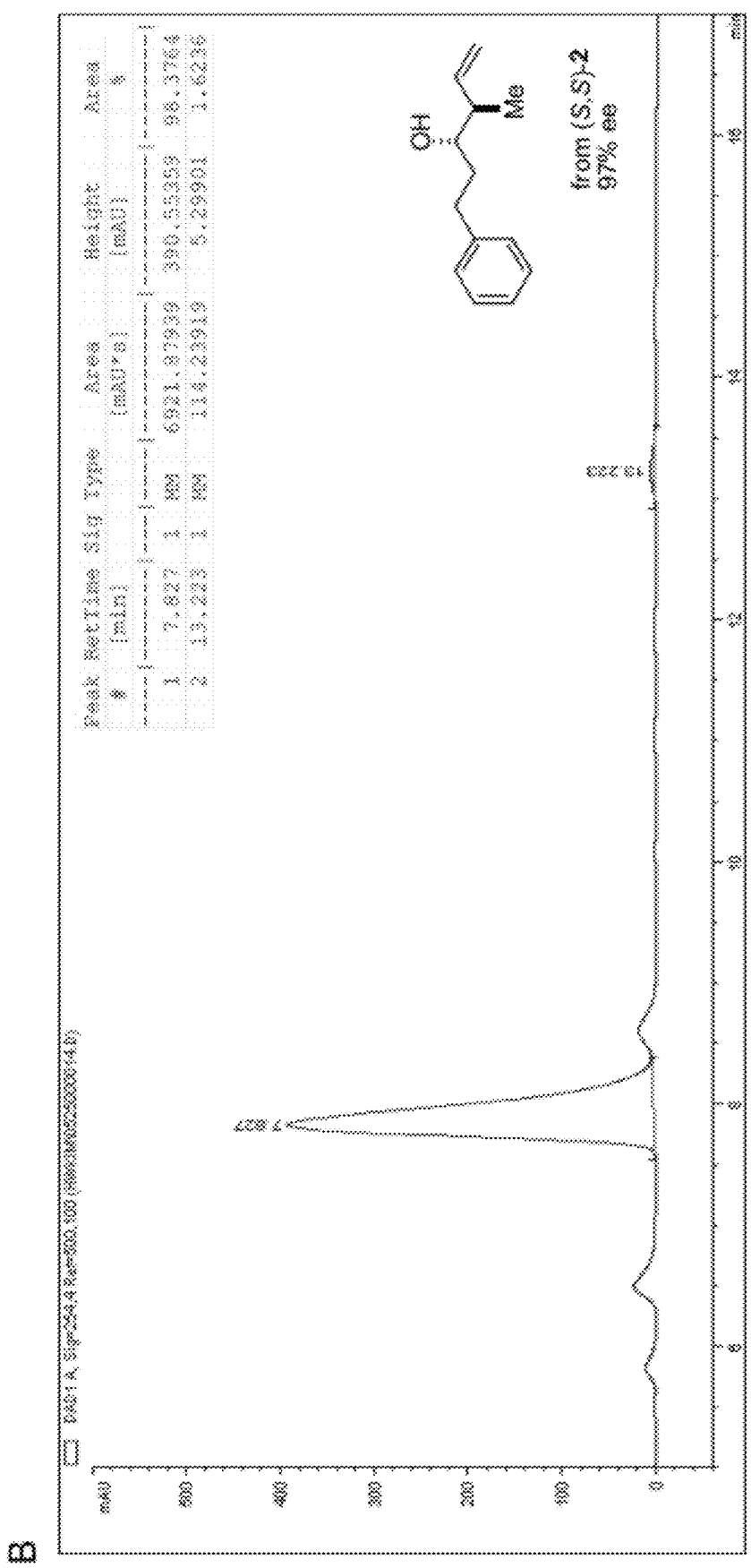
Figure 9A:
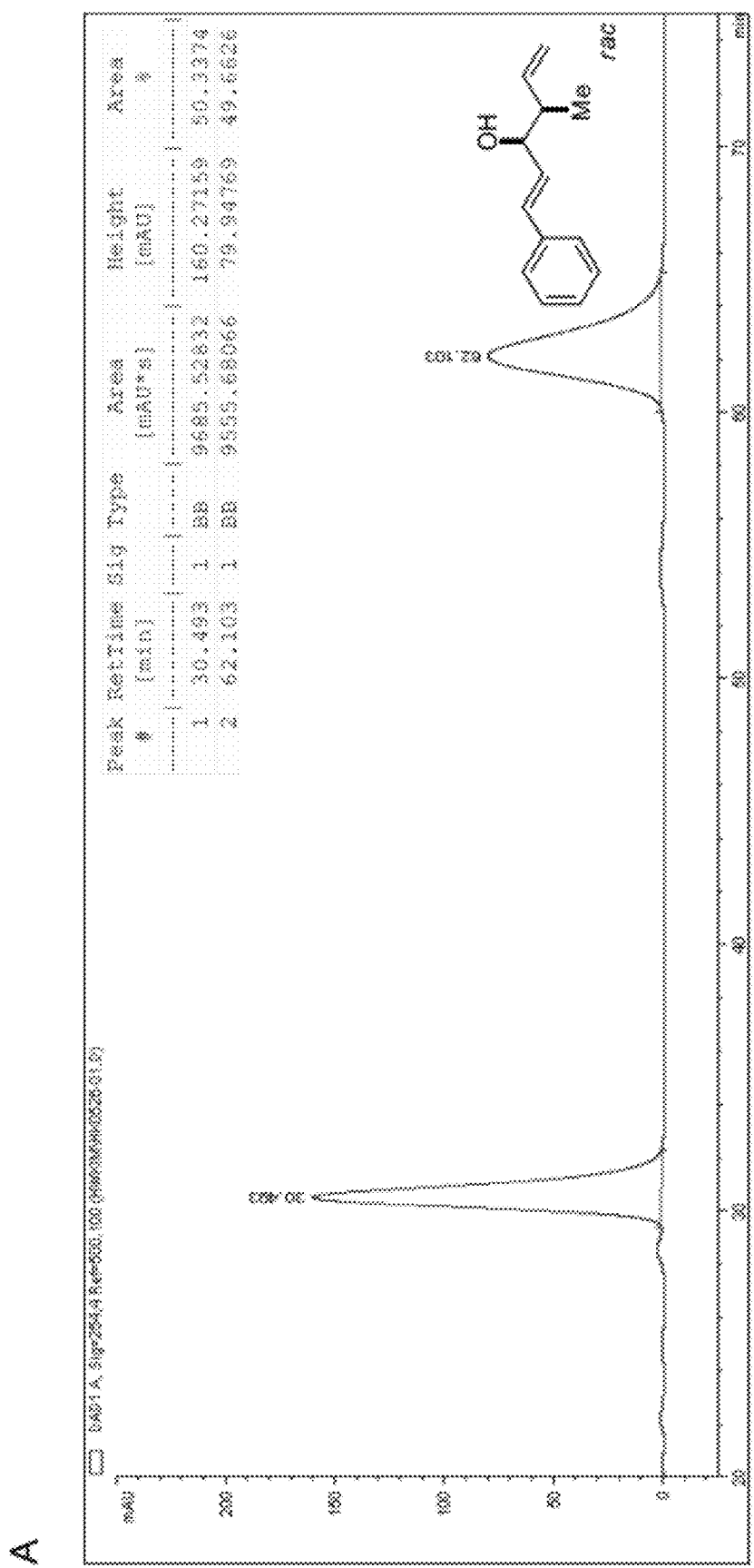
FIG. 9. The HPLC traces of (A) racemic crotylation of trans-cinnamaldehyde using cis-crotylboronic acid pinacol ester and (B) crotylation of trans-cinnamaldehyde using (S,S)-1 and Sc(OTf)$_3$ from a Chiracel OD column, 2% i-PrOH in hexanes, 1 mL/min.
Figure 9B:
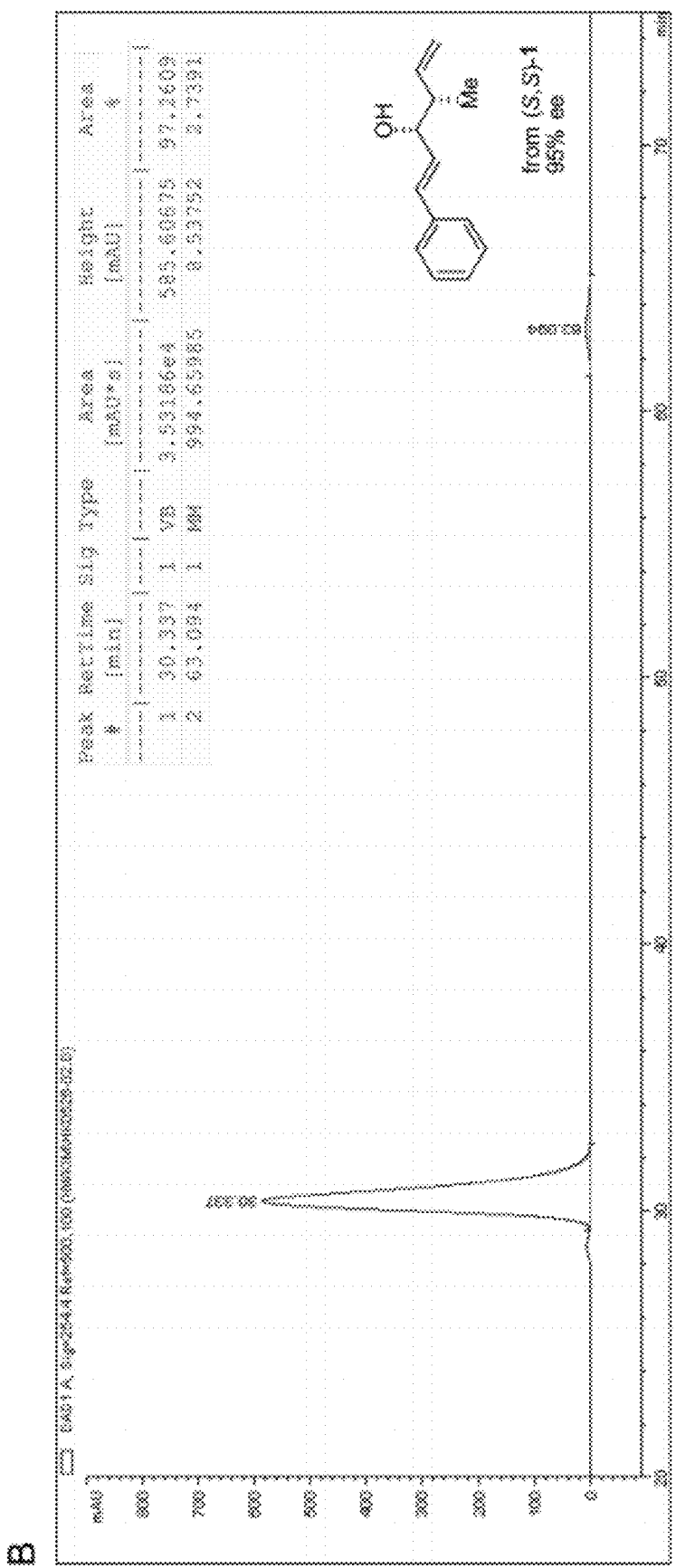
Figure 10A:
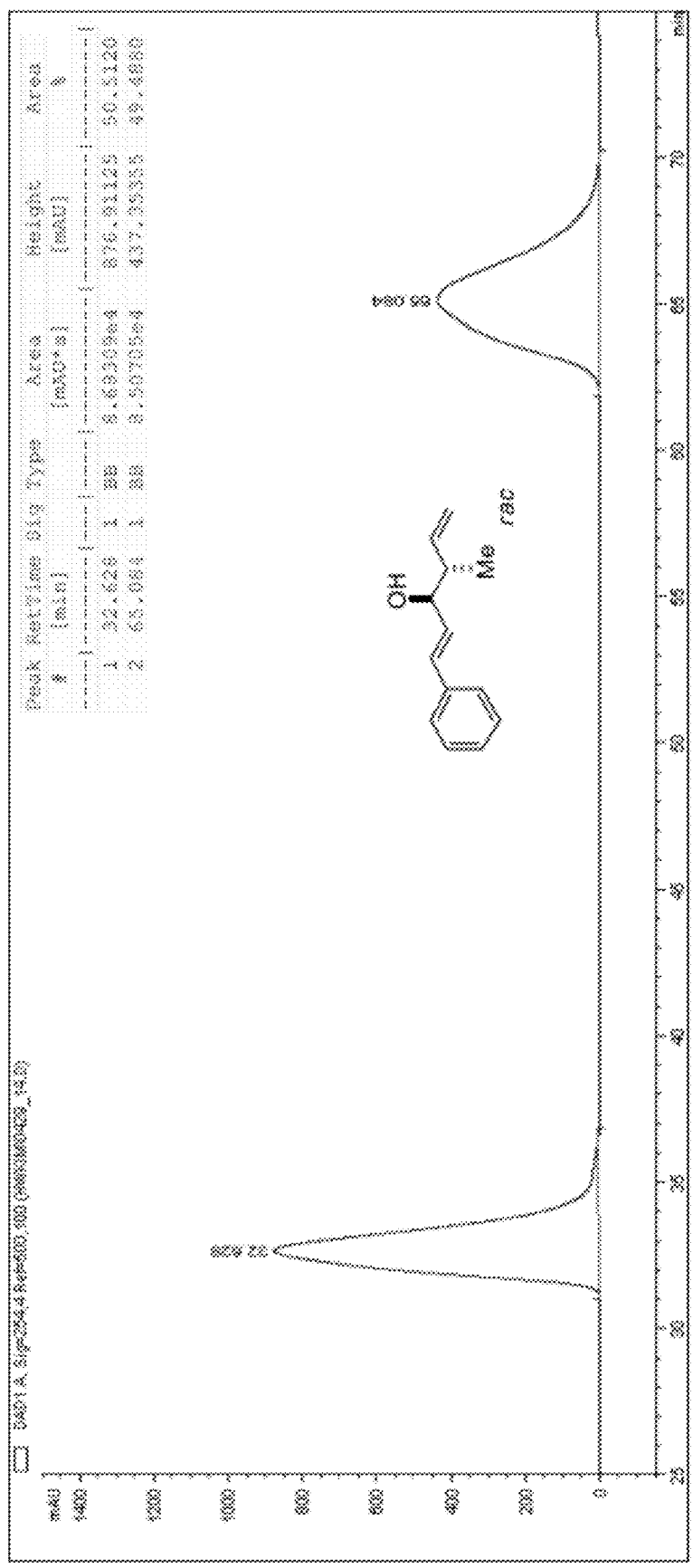
FIG. 10. The HPLC traces of (A) racemic crotylation of trans-cinnamaldehyde using trans-crotylboronic acid pinacol ester and (B) crotylation of trans-cinnamaldehyde using (S,S)-2 and Sc(OTf)$_3$ from a Chiracel OD column, 2% i-PrOH in hexanes, 1 mL/min.
Figure 10B:
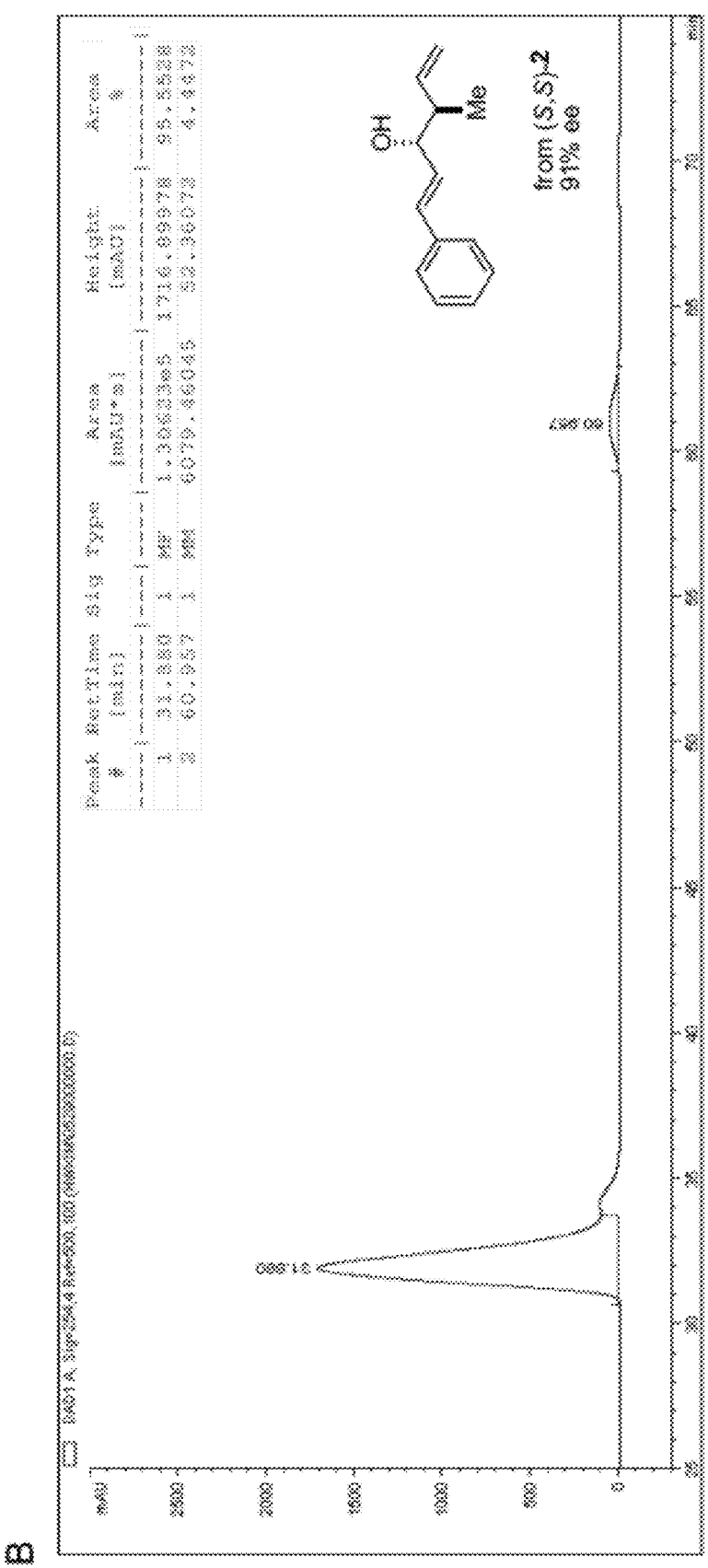

While attempts to catalyze the reactions of silanes 1 and 2 by the addition of Brønsted acids were unsuccessful, it was found that Lewis acids were effective, with Sc(OTf)$_3$ proving the most effective (FIG. 1). The affinity of Sc(OTf)$_3$ toward nitrogen-derived silanes 1 and 2 was surprising, particularly in light of studies indicating that the oxygen atoms are required for allylboronate activation with Sc(OTf)$_3$ (Rauniyar, V.; Hall, D. G. *J. Am. Chem. Soc.* 2004, 126, 4518; hereby incorporated by reference in its entirety). Thus, treatment of α-methylcinnamaldehyde with reagents (S,S)-1 and (S,S)-2 and 5 mol % Sc(OTf)$_3$ in CH$_2$Cl$_2$ at 0° C. for 1 h led to the isolation of products 5 and 6 as single diastereomers ($\geq$40:1 dr) in 87% yield and 94% and 91% ee, respectively (Scheme 2; FIGS. 2, 3, and 4; Kim, H.; Ho, S.; Leighton, J. L. *J. Am. Chem. Soc.* 2011, DOI: 10.1021/ja200712f; hereby incorporated by reference in its entirety). This is quite unexpected in contrast to the case in which no Sc(OTf)$_3$ is used, which produced no reaction with α-methylcinnamaldehyde using the same reagents (Scheme 1).

Scheme 2.

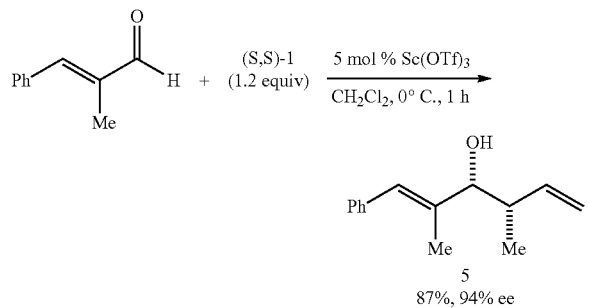

5
87%, 94% ee

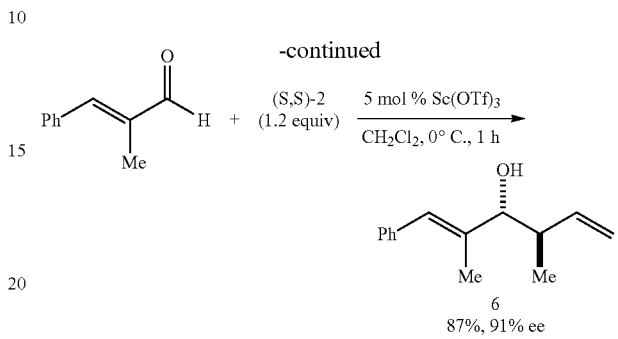

6
87%, 91% ee

Thus, in some embodiments, the aldehyde substrates may be, for example, aryl, aliphatic, saturated or unsaturated, chiral or achiral. Exemplary aryl aldehydes include aldehydes substituted with an aromatic or heteroaromatic functional group. Exemplary aromatic groups include phenyl, naphthyl, anthracenyl and the like, and may or may not be further substituted. Exemplary heteroaromatic functional groups include aromatic groups comprised of one or more heteroatoms selected from the group consisting of nitrogen, oxygen and sulfur, and may or may not be further substituted.

In other embodiments, the aldehyde substrates may also be alkyl-, alkenyl- or alkynyl-derived, and further substituted with one or more alkyl, aryl, heteroaryl, oxygen, nitrogen, and/or silicon-derived functional groups.

In still other embodiments, the aldehyde substrates are achiral. In other embodiments, the aldehyde substrates contain one or more stereogenic centers.

In one embodiment, the aldehyde substrates are simple aldehydes. Simple aldehydes include, for example, achiral alkyl aldehydes, optionally substituted with one or more oxygen-derived functional groups.

In another embodiment, the aldehyde substrates are complex aldehydes. Complex aldehydes include, for example, aldehydes containing a chiral center, aromatic aldehydes, unsaturated aldehydes, sterically hindered aldehydes, alkyl aldehydes that may be substituted with one or more alkyl, aryl, heteroaryl, oxygen, nitrogen, and/or silicon-derived functional groups.

The results of a study of the crotylation reactions of three aldehydes using silanes (S,S)-1 and (S,S)-2 are compiled in Table 1 (Kim, H.; Ho, S.; Leighton, J. L. *J. Am. Chem. Soc.* 2011, DOI: 10.1021/ja200712f; hereby incorporated by reference in its entirety). As shown, the yields and enantioselectivities are excellent across the board (in all cases the diastereoselectivity was $\geq$40:1), whereas the corresponding reactions without Sc(OTf)$_3$ typically required significantly longer reaction times (~20 h) and provided yields that were in the range of 52-83% (Hackman, B. M.; Lombardi, P. J.; Leighton, J. L. *Org. Lett.* 2004, 6, 4375; hereby incorporated by reference in its entirety). HPLC traces for the reaction products are provided in FIGS. 5B-10B. FIGS. 5A-10A provide the reference products from the corresponding racemic crotylation methods.

TABLE 1

Sc(OTf)₃-Catalyzed Aldehdye Crotylation Reactions

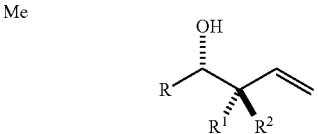

(1.2 equiv.)
(S,S)-1: R¹ = Me, R² = H
(S,S)-2: R¹ = H, R² = Me

| entry | R | silane | yield (%) | ee(%) |
|---|---|---|---|---|
| 1 | PhCH₂CH₂ | (S,S)-1 | 96 | 96 |
| 2 | PhCH₂CH₂ | (S,S)-2 | 96 | 97 |
| 3 | Ph | (S,S)-1 | 94 | 93 |
| 4 | Ph | (S,S)-2 | 96 | 91 |
| 5 | (E)-PhCH=CH | (S,S)-1 | 96 | 95 |
| 6 | (E)-PhCH=CH | (S,S)-2 | 93 | 91 |

Figure 11A:
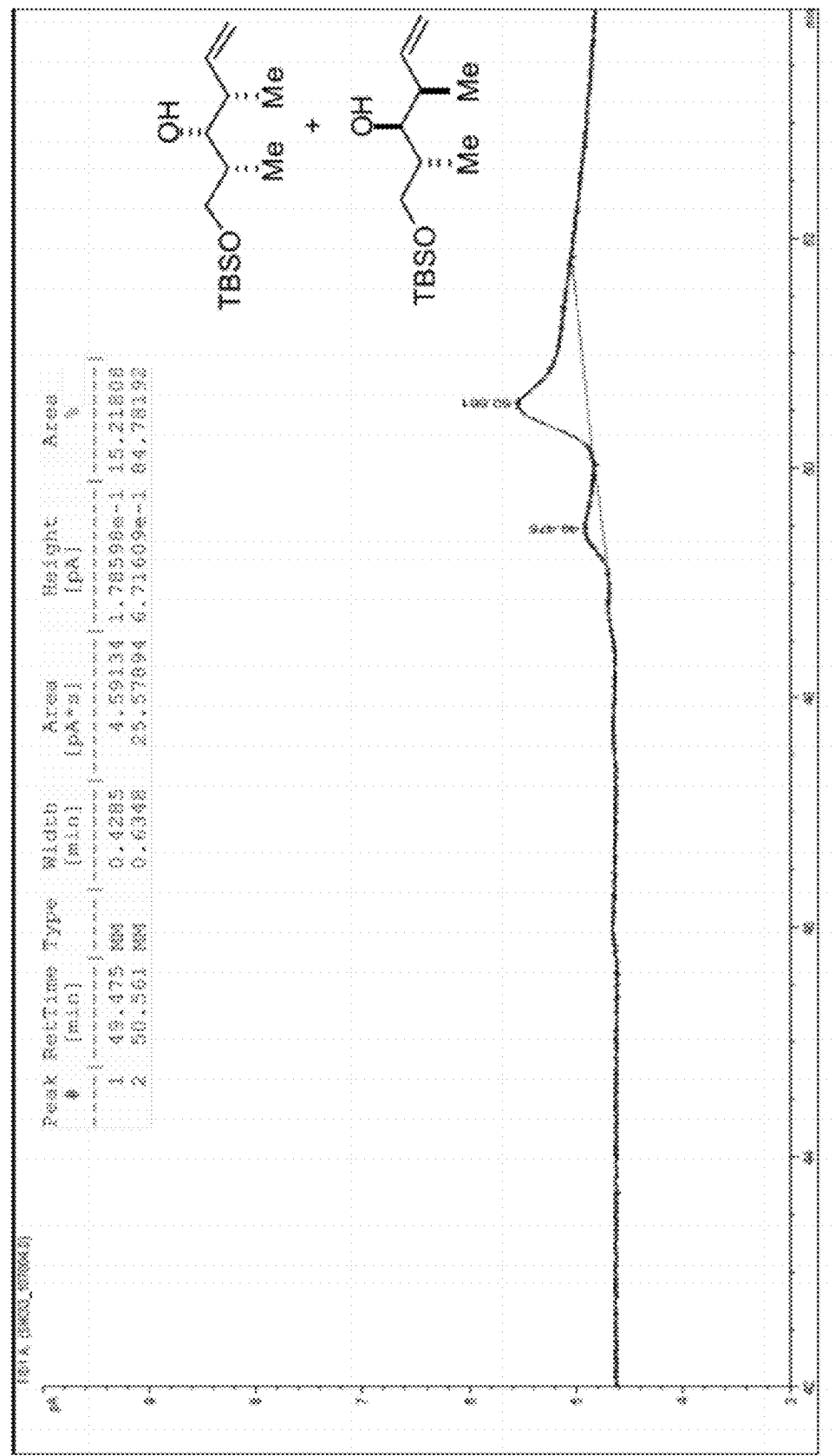
FIG. 11. The HPLC traces of (A) diastereomeric mixtures by crotylation of 7 using cis-crotylboronic acid pinacol ester, (B) diastereomeric mixtures by crotylation of 7 using trans-crotylboronic acid pinacol ester, and (C) a mixture of all diastereomers shown in (A) and (B) from a Supelco β-Dex column, isothermal 110° C., 1 mL/min.
Figure 11B:
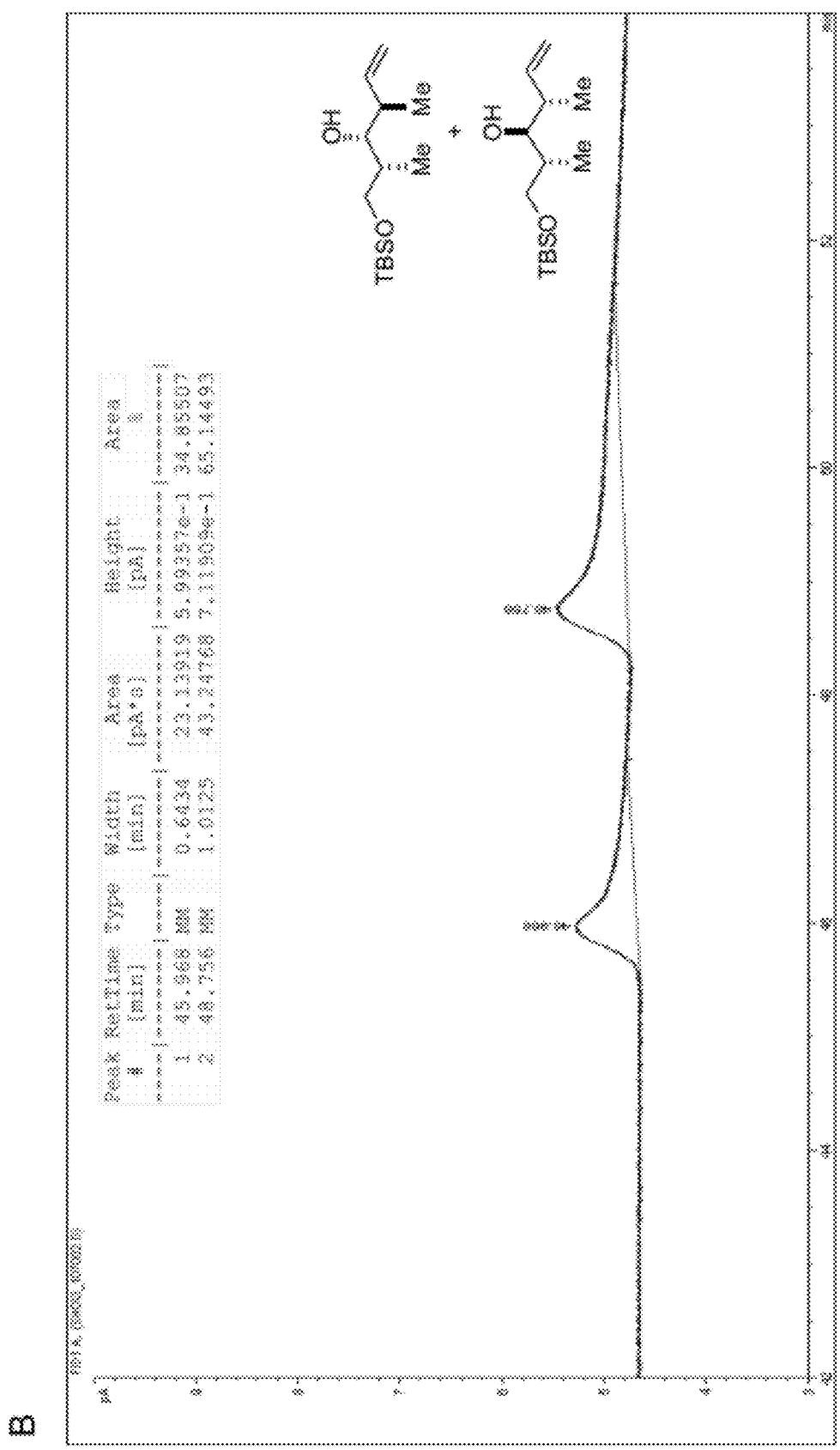
Figure 11C:
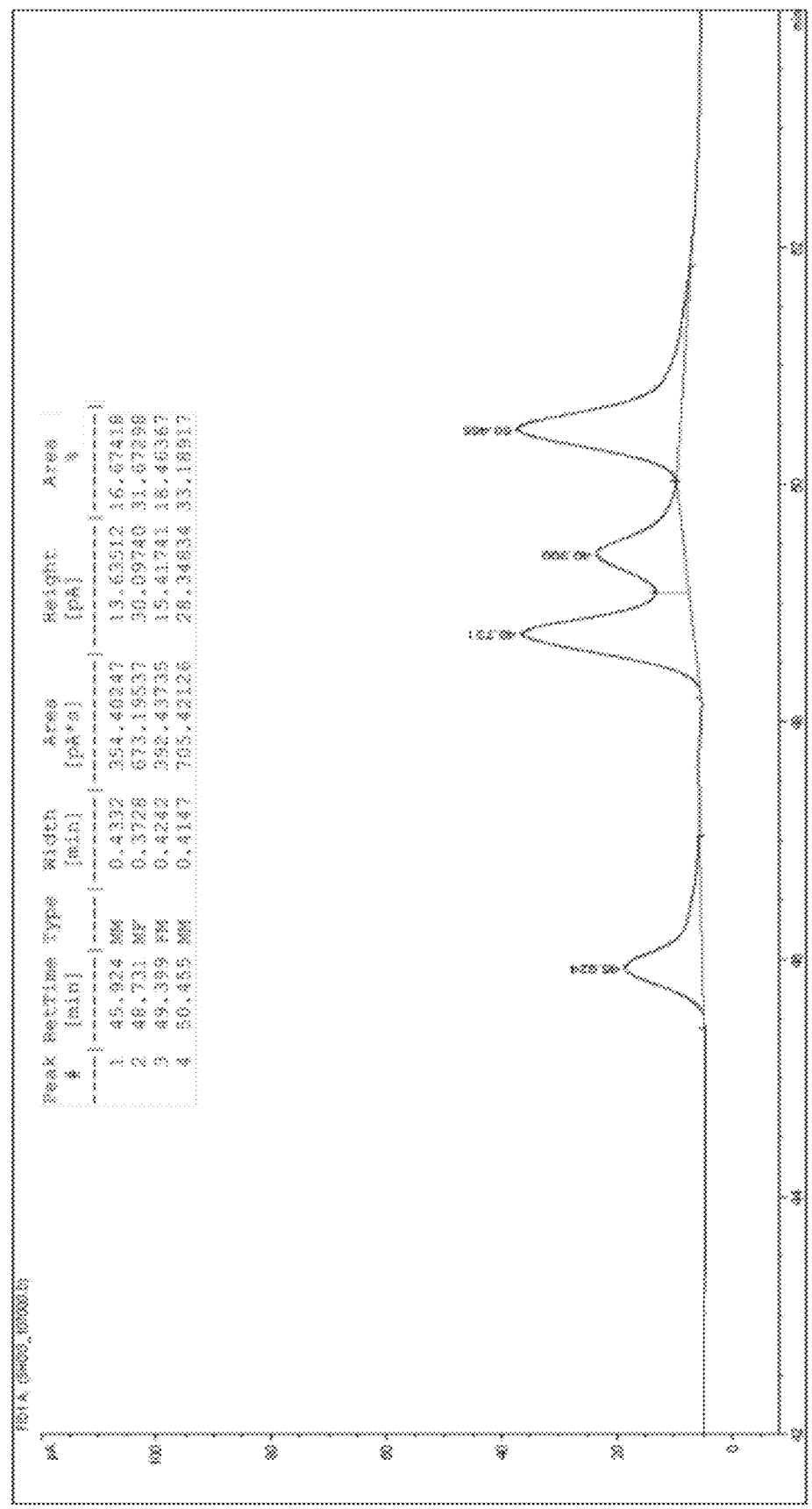
Figure 12A:
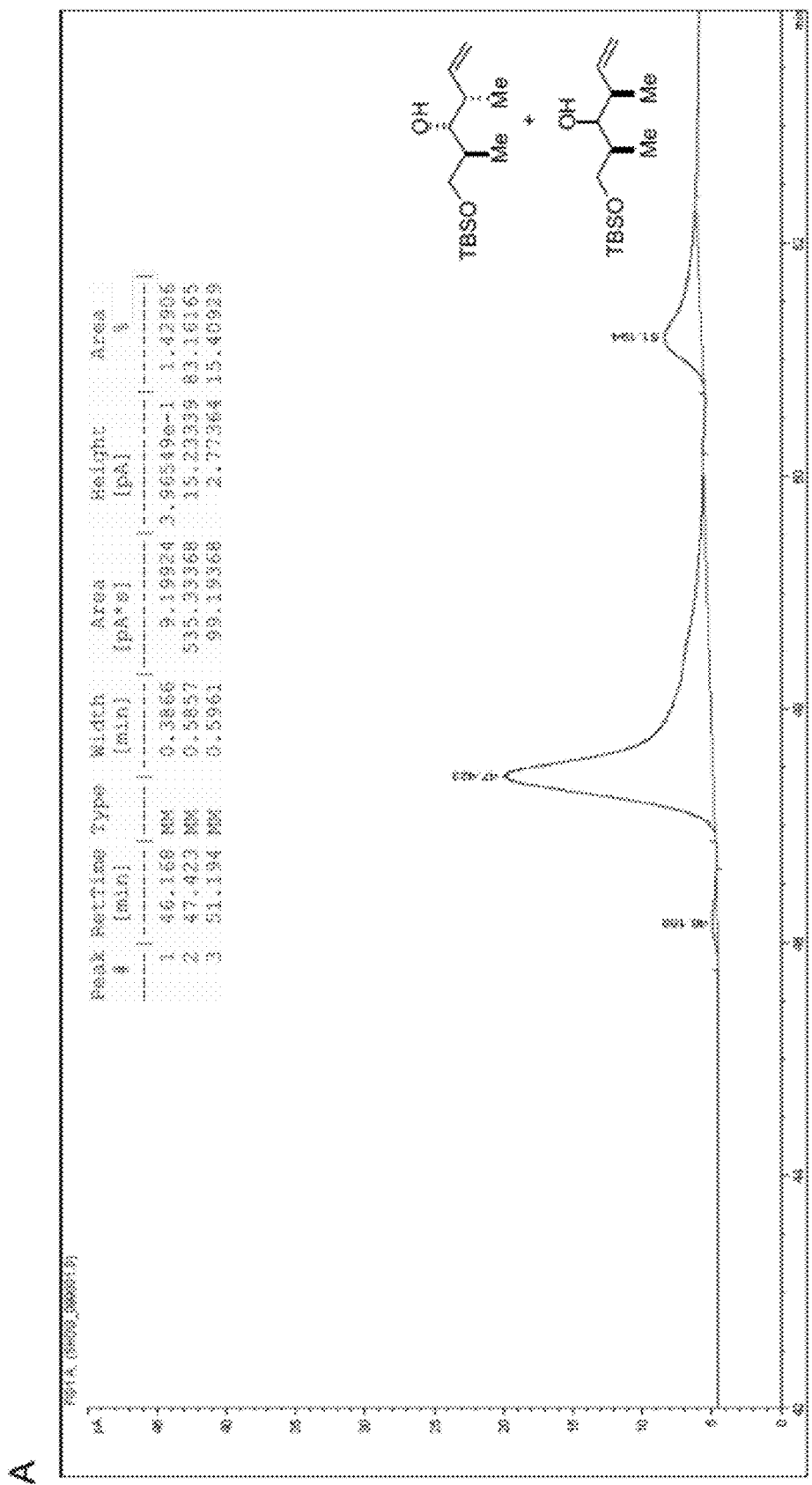
FIG. 12. The HPLC traces of (A) diastereomeric mixtures by crotylation of 8 using cis-crotylboronic acid pinacol ester, (B) diastereomeric mixtures by crotylation of 8 using trans-crotylboronic acid pinacol ester, and (C) a mixture of all diastereomers shown in (A) and (B) from a Supelco β-Dex 325 column, isothermal 110° C., 1 mL/min.
Figure 12B:
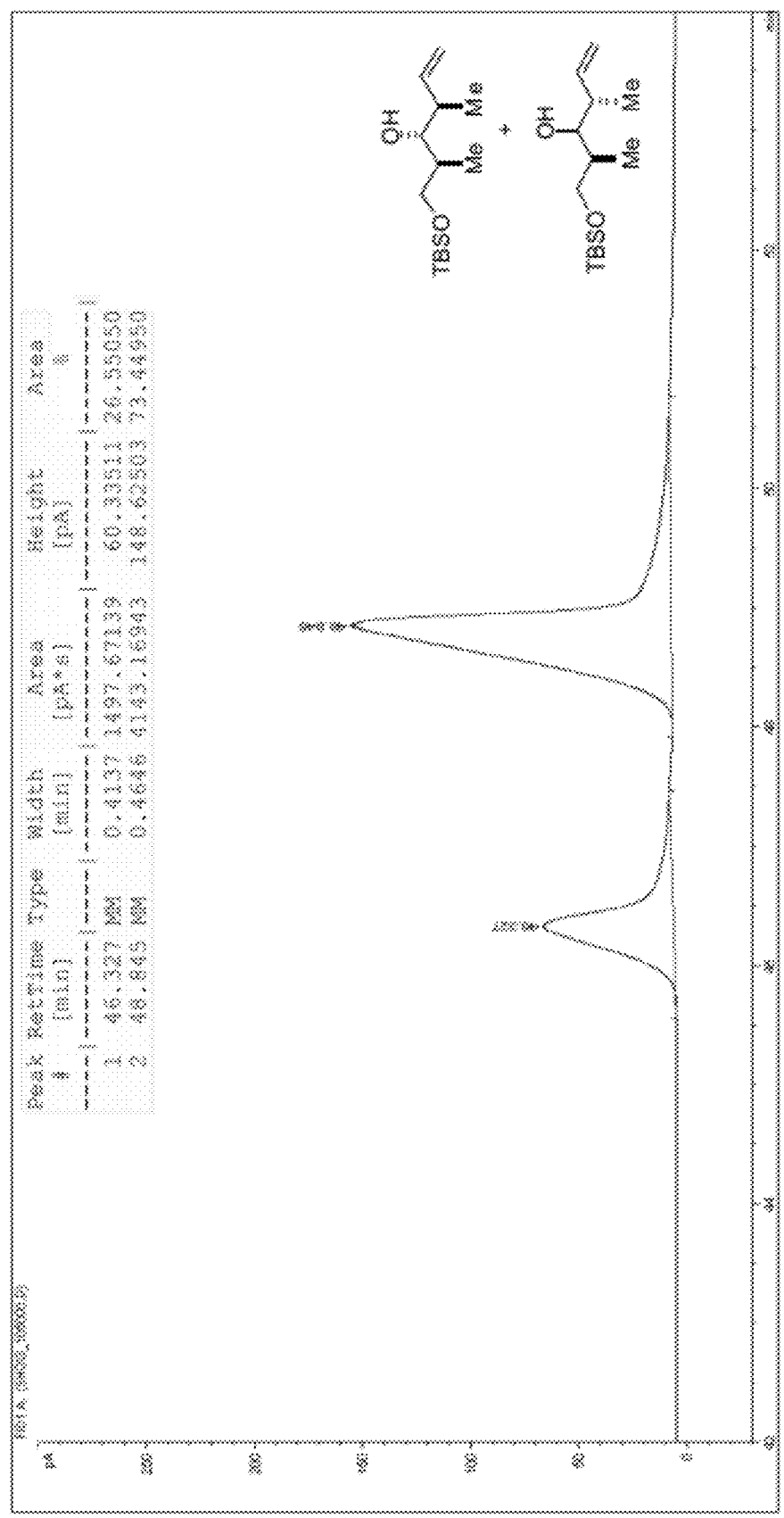
Figure 12C:
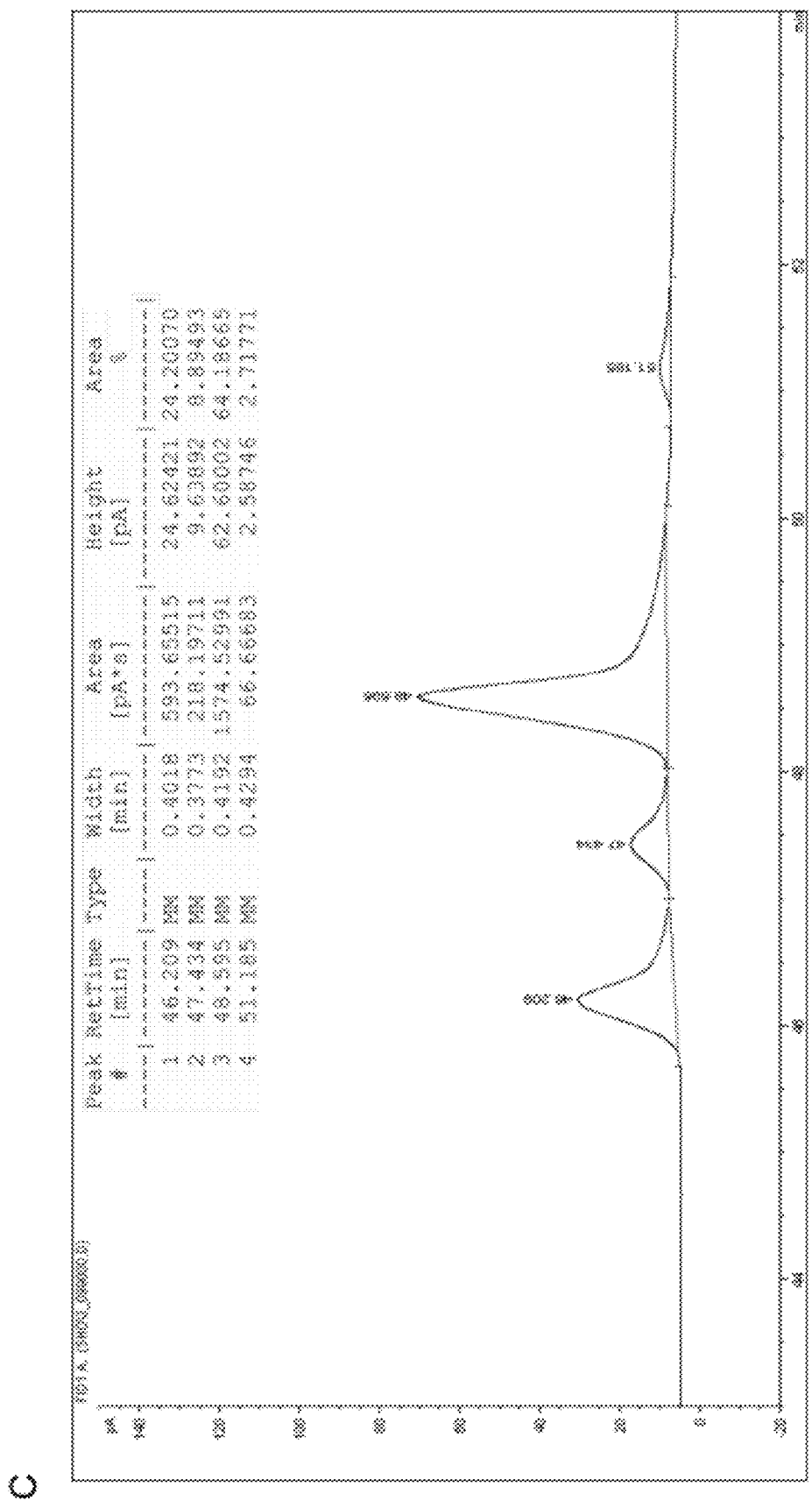
Figure 13A:
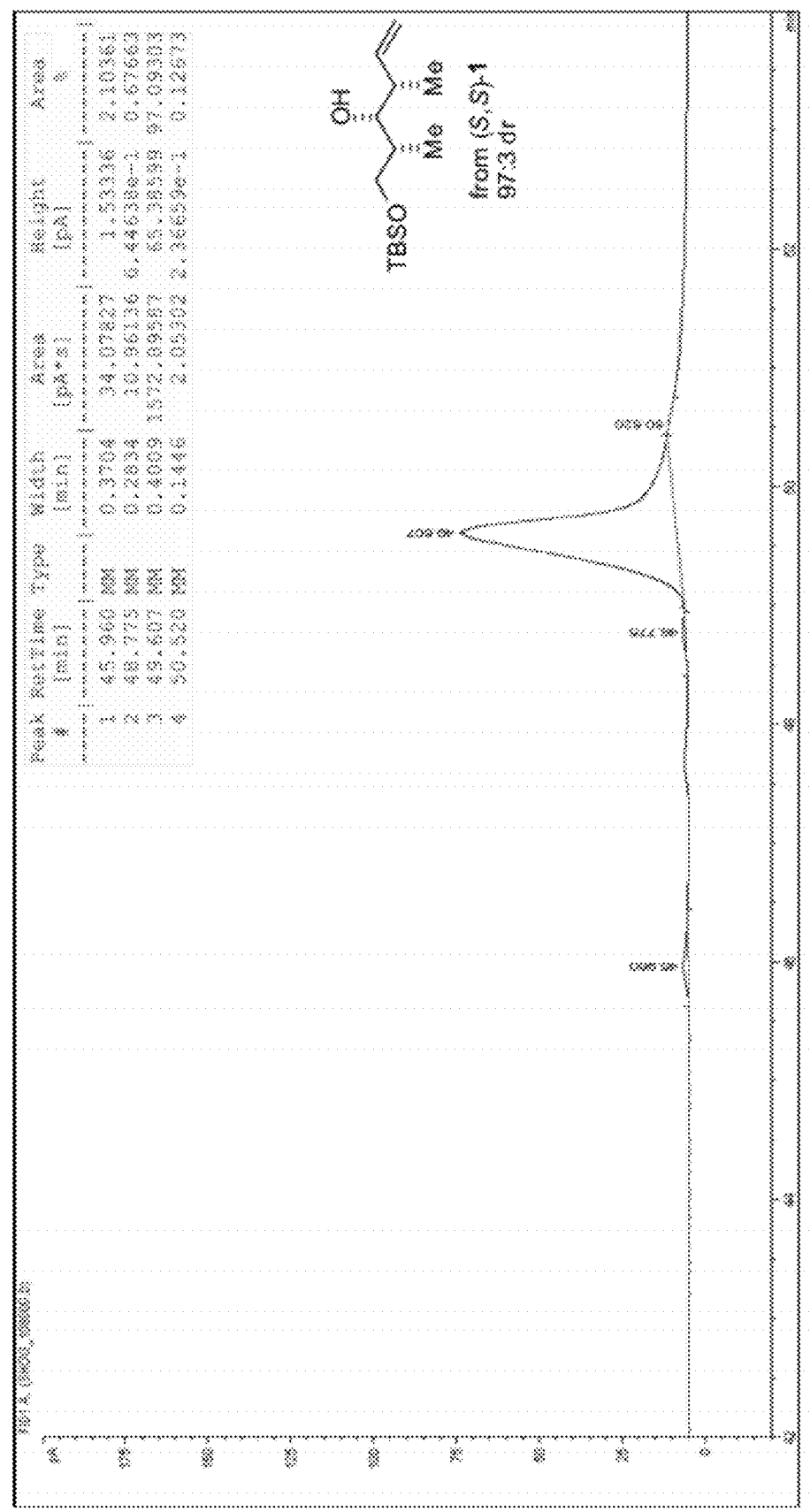
FIG. 13. The HPLC traces of (A) crotylation product of 7 produced using (S,S)-1 and Sc(OTf)$_3$ and (B) crotylation product of 7 produced using (S,S)-2 and Sc(OTf)$_3$ from a Supelco β-Dex column, isothermal 110° C., 1 mL/min.
Figure 13B:
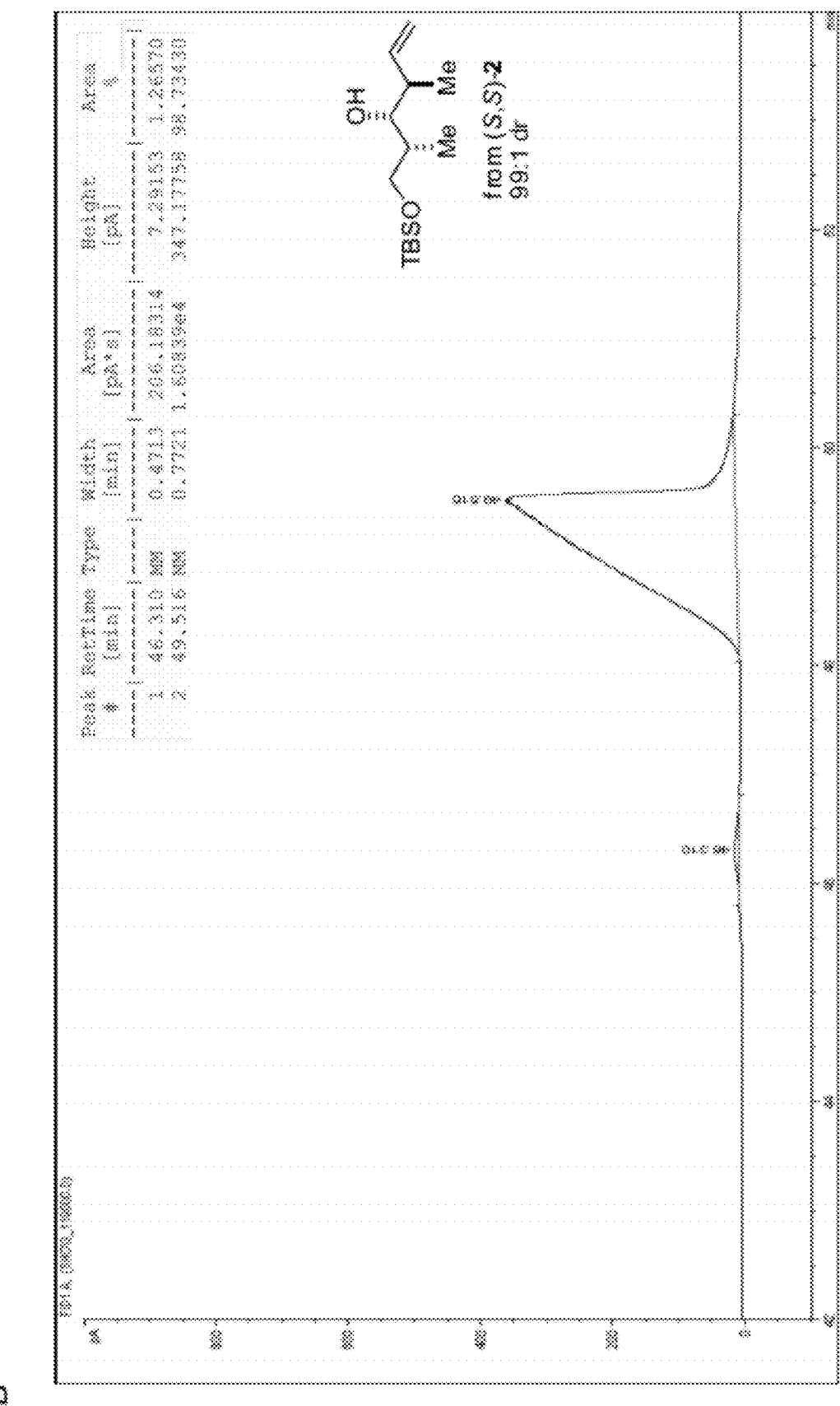
Figure 14A:
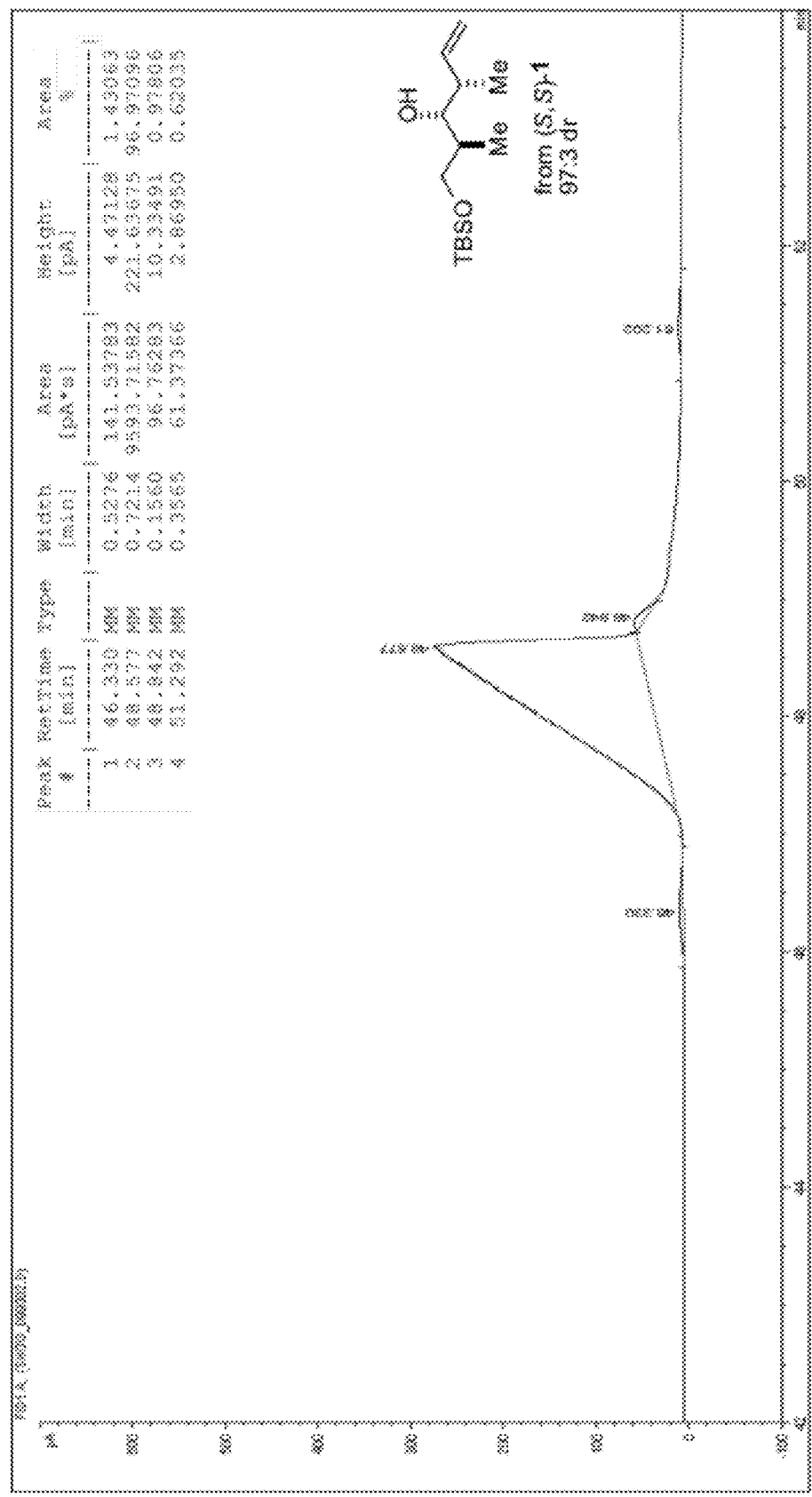
FIG. 14. The HPLC traces of (A) crotylation product of 8 produced using (S,S)-1 and Sc(OTf)$_3$ and (B) crotylation product of 8 produced using (S,S)-2 and Sc(OTf)$_3$ from a Supelco β-Dex column, isothermal 110° C., 1 mL/min.
Figure 14B:
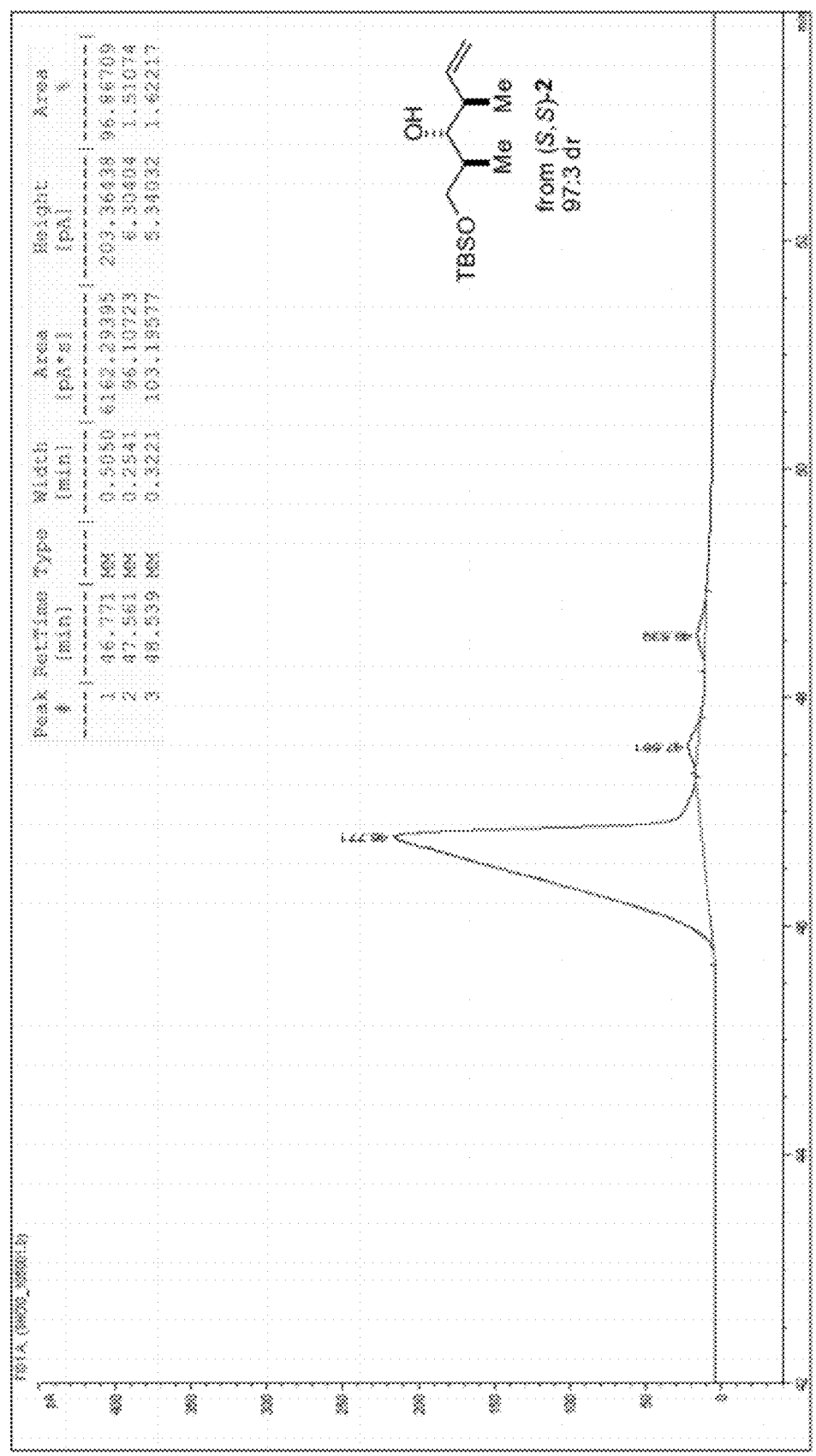
Figure 15A:
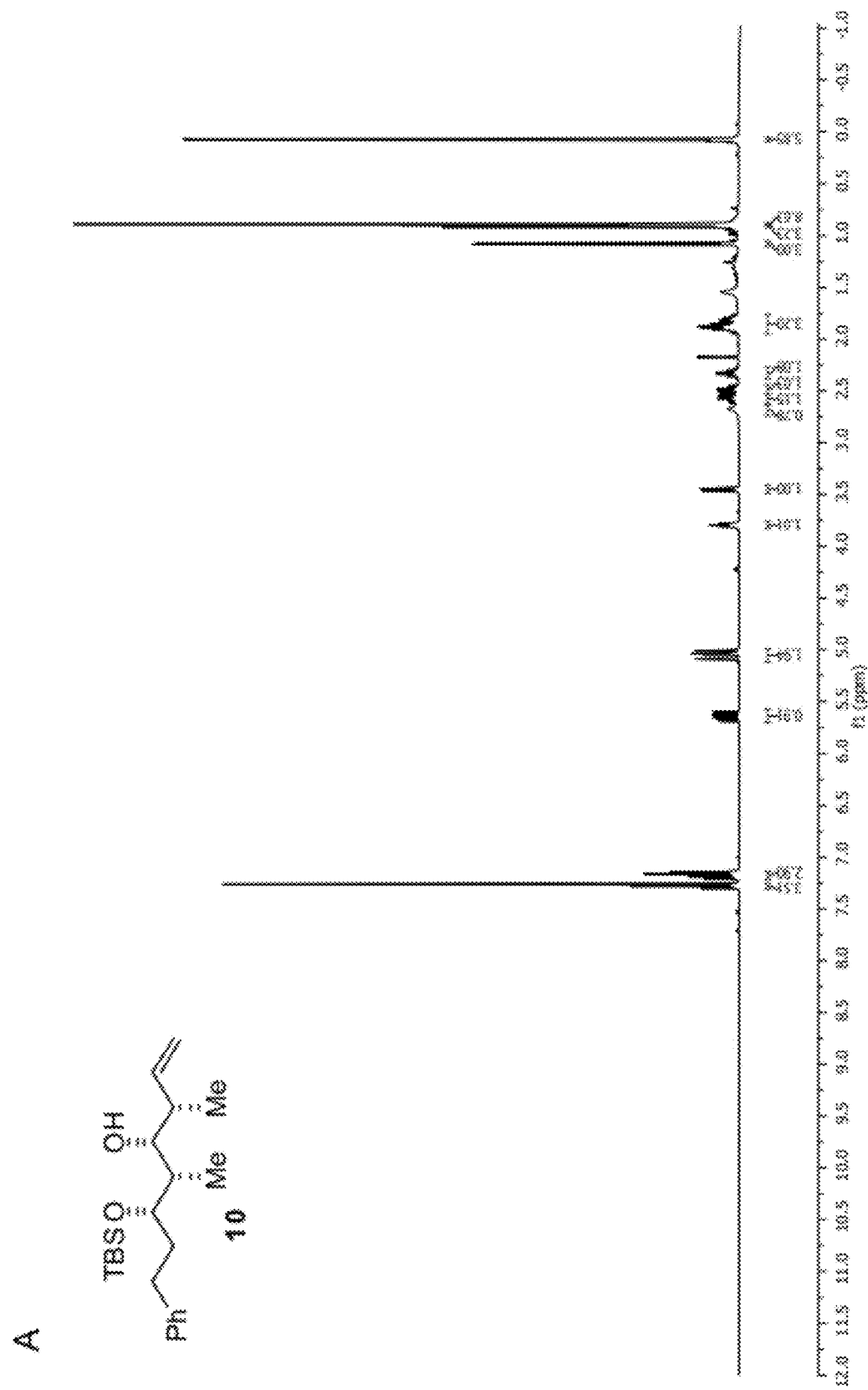
FIG. 15. The (A) $^1$H NMR spectrum and (B) $^{13}$C NMR spectrum of (3S,4S,5R,6S)-10 in CDCl$_3$.
Figure 15B:
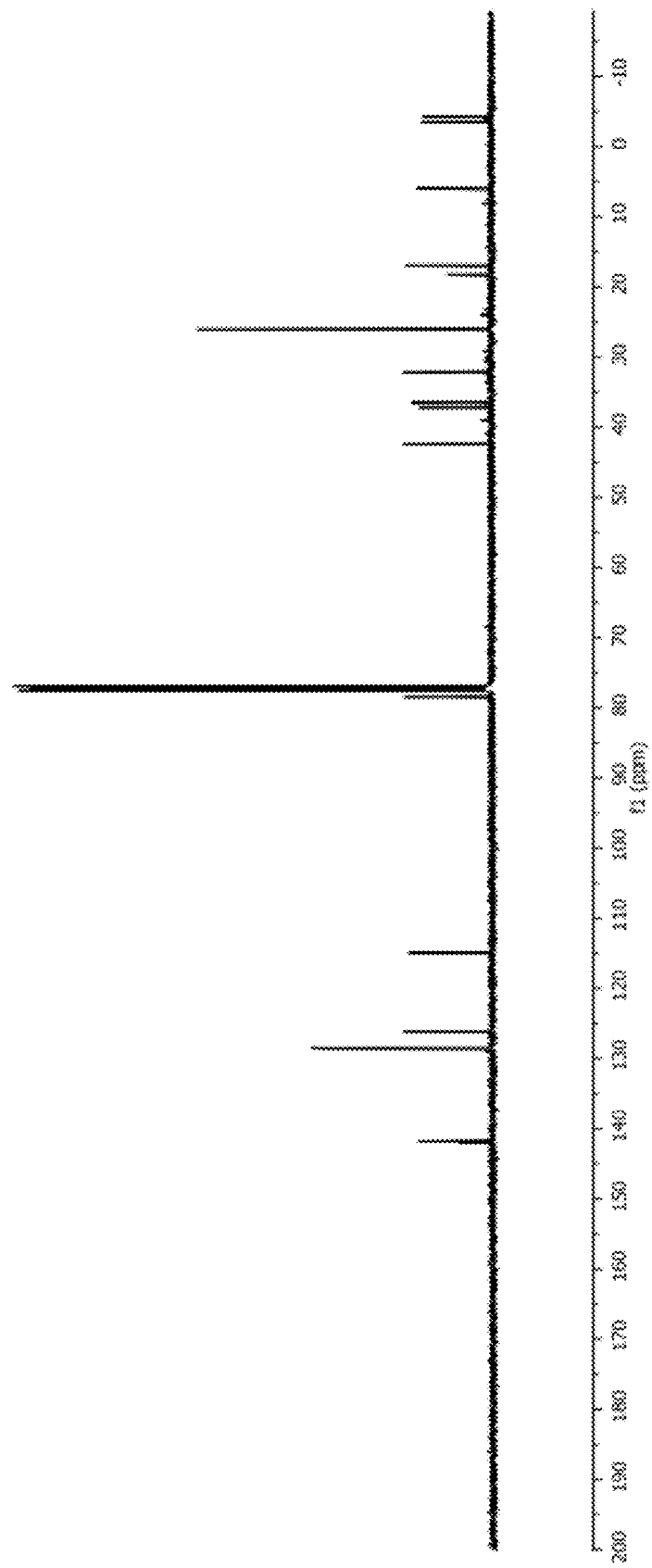
Figure 16A:
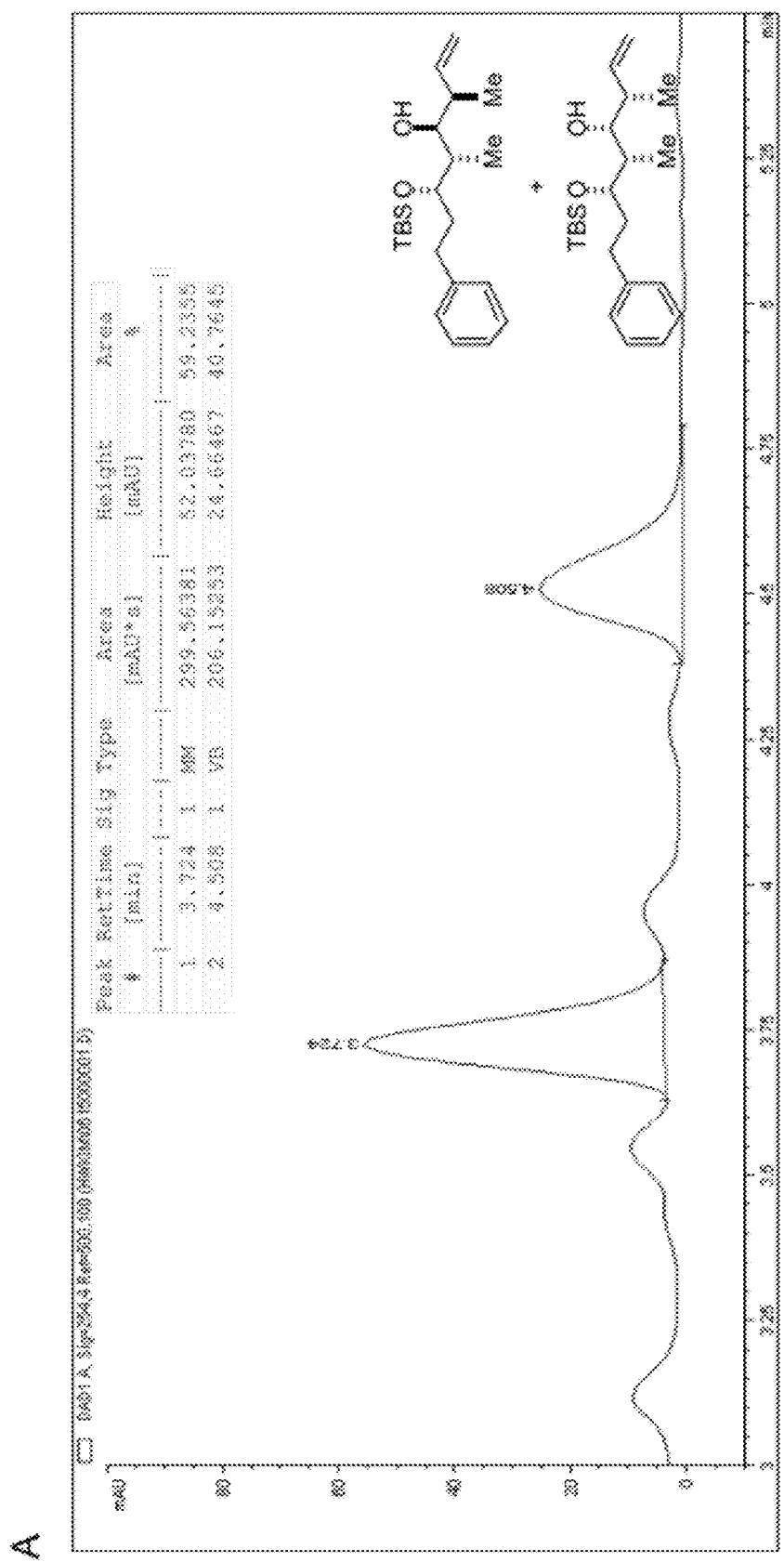
FIG. 16. The HPLC traces of (A) diastereomeric mixtures by crotylation of 9 using cis-crotylboronic acid pinacol ester and (B) crotylation of 9 to produce (3S,4S,5R,6S)-10 using (S,S)-1 and Sc(OTf)$_3$ from a Chiralpak AD-H column, 2% i-PrOH in hexanes, 1 mL/min.
Figure 16B:
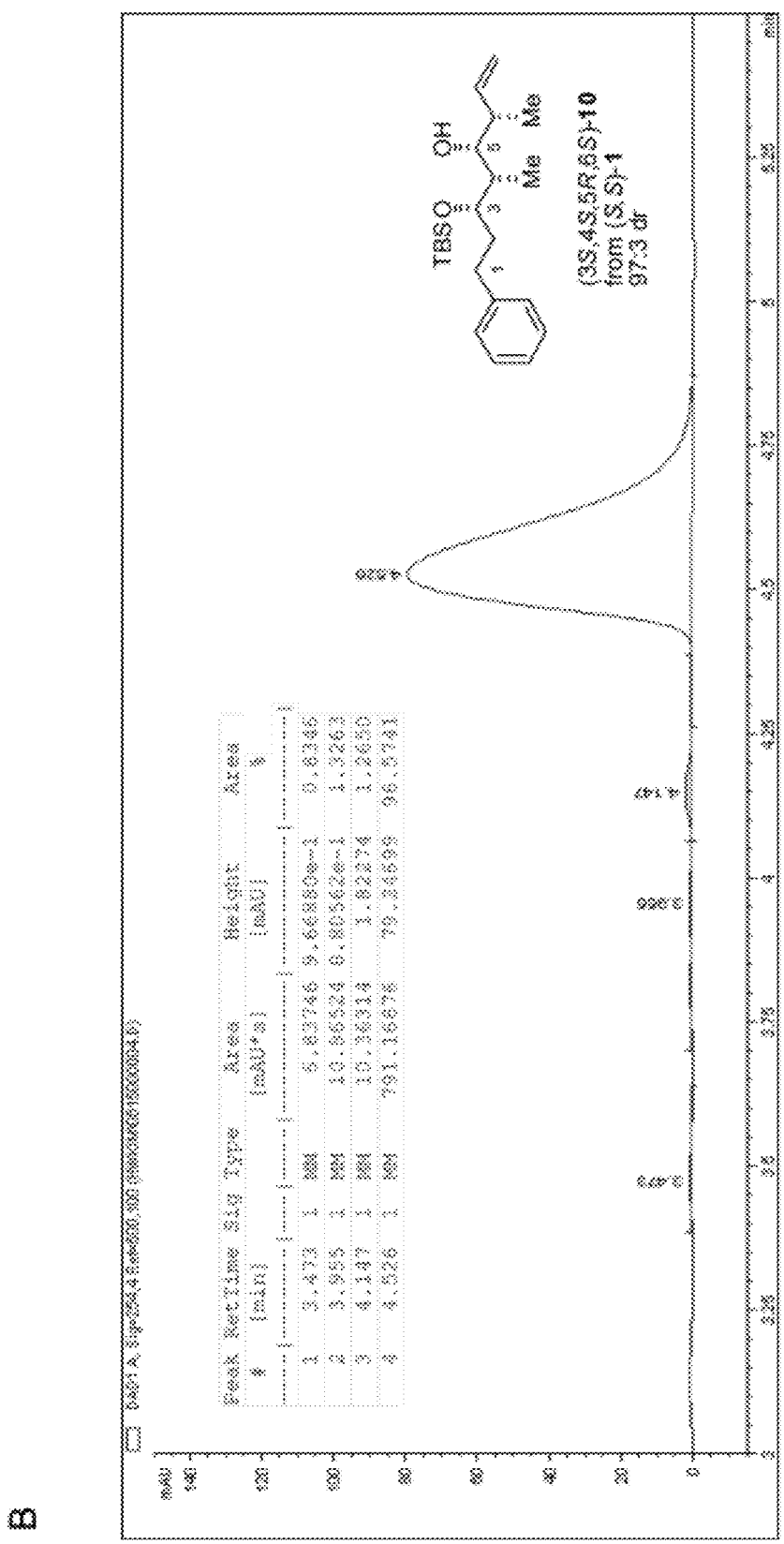

Complex chiral aldehydes such as 3 represent one of the more important classes of aldehydes for crotylation reactions, and any method that would lay claim to being a comprehensive solution should be able to provide for high levels of reagent control for all possible stereochemical permutations. Commonly employed Roche ester-derived aldehydes 7 and 8 were treated with (S,S)-1 and (S,S)-2 using the standard conditions outlined above, and in every case the reactions proceeded with excellent diastereoselectivity (≧97:3 dr, major diastereomer:sum of all minor diastereomers) corresponding to reagent control (Scheme 3). HPLC traces of reference diastereomeric mixtures are shown in FIGS. 11 and 12, and HPLC traces of the products obtained using the present invention are shown in FIGS. 13 and 14. Additionally, although it was slower, crotylation of aldehyde 9 with (S,S)-1—a fully mismatched reaction (Evans, D. A.; Dart, M. J.; Duffy, J. L.; Rieger, D. L. *J. Am. Chem. Soc.* 1995, 117, 9073; hereby incorporated by reference in its entirety)—provided the product of reagent control, 10, in 80% yield and with excellent (97:3) diastereoselectivity (FIG. 15). The HPLC traces of the reference diastereomeric mixture are shown in FIG. 16A and the product obtained using the present invention are shown in FIG. 16B.

Scheme 3.

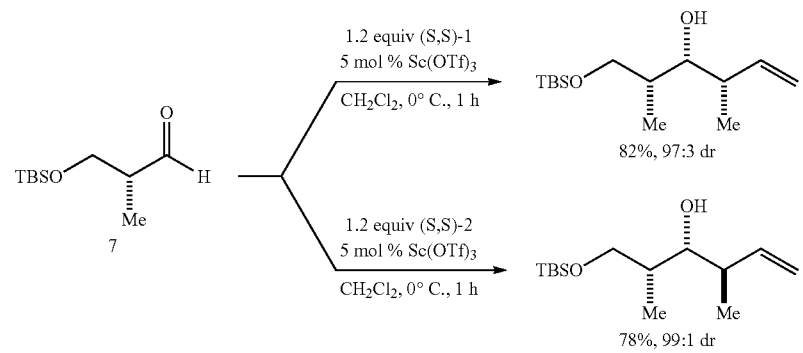

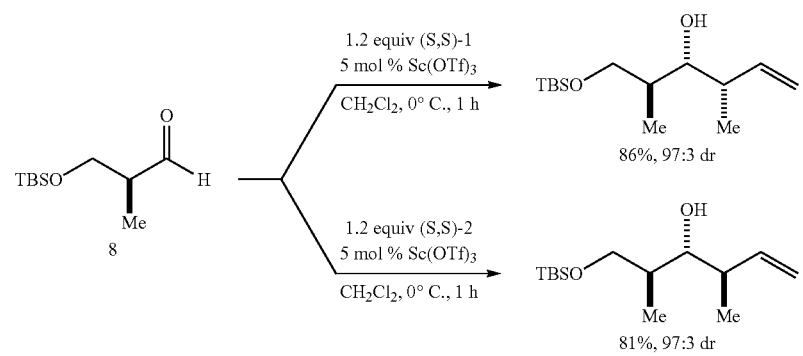

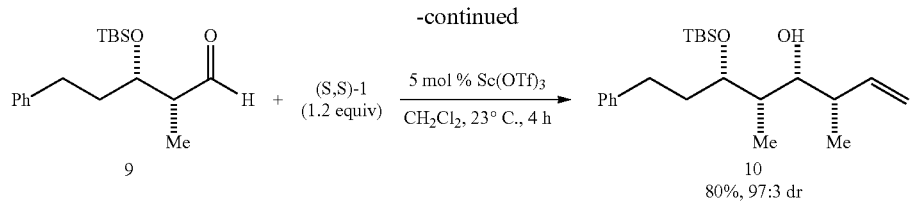

10

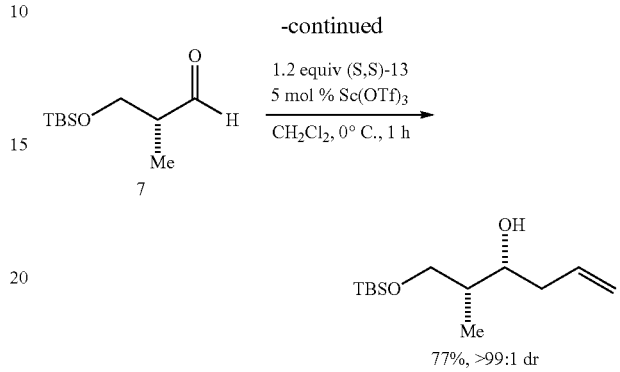

Figure 17A:
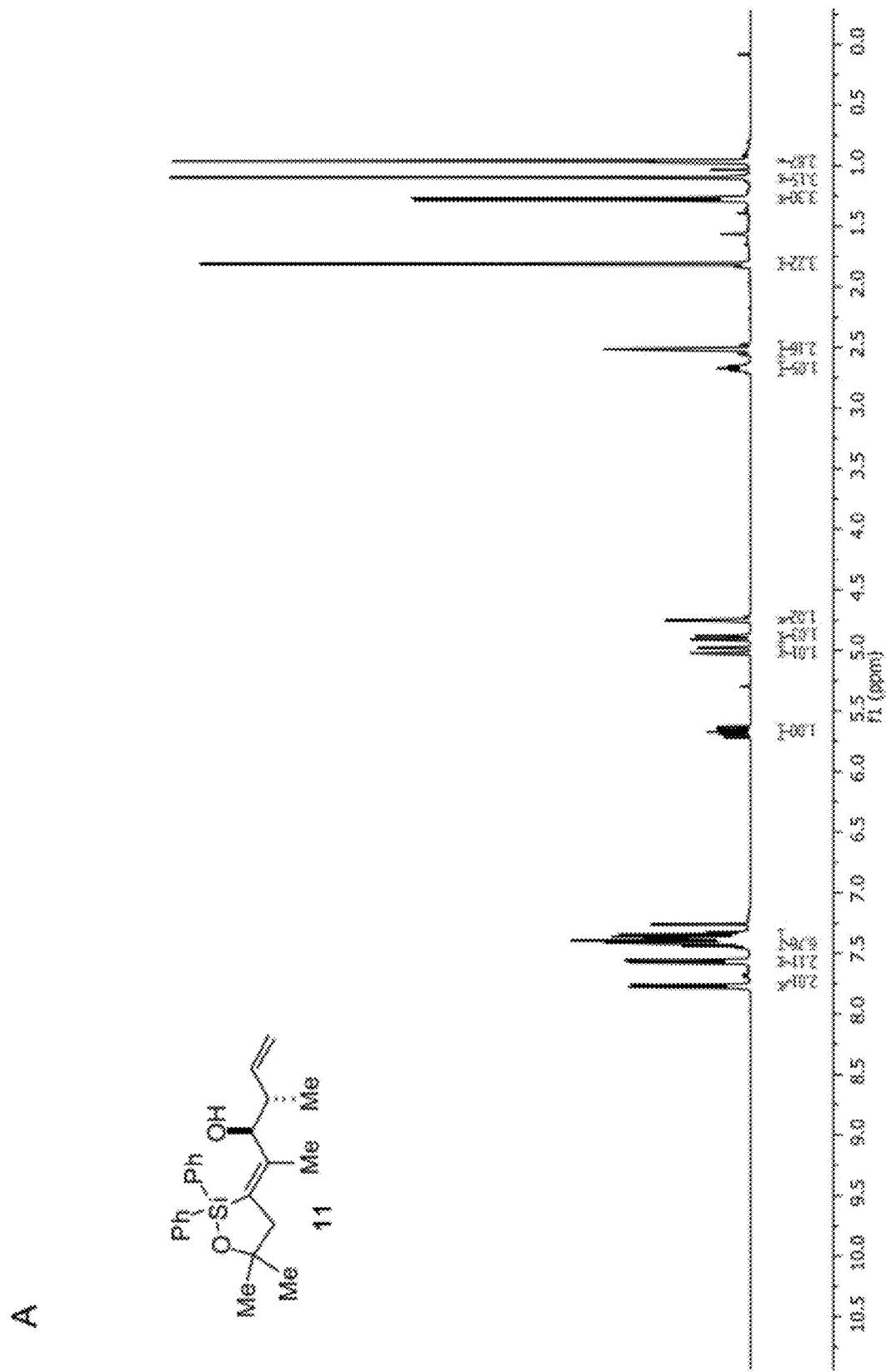
FIG. 17. The (A) $^1$H NMR spectrum and (B) $^{13}$C NMR spectrum of (5S,6R)-11 in CDCl$_3$.
Figure 17B:
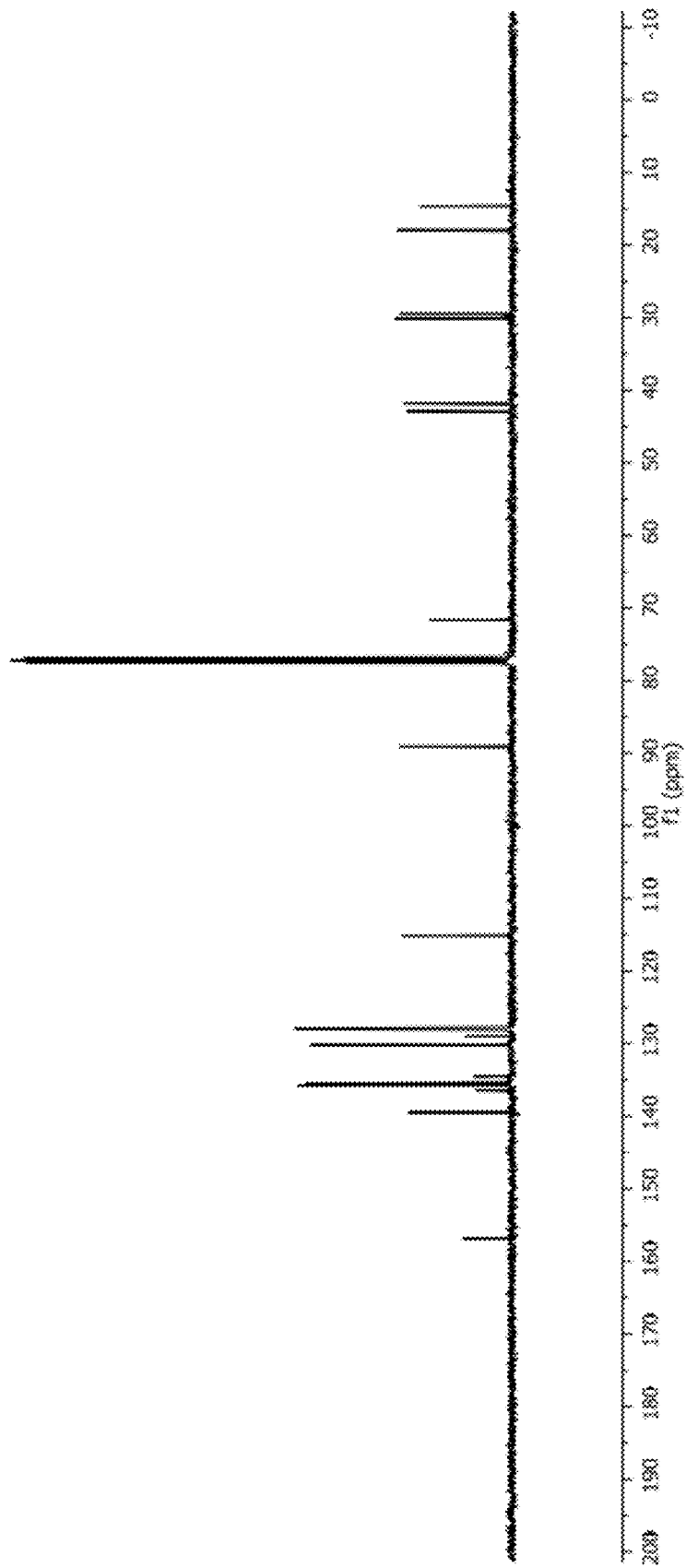
Figure 18A:
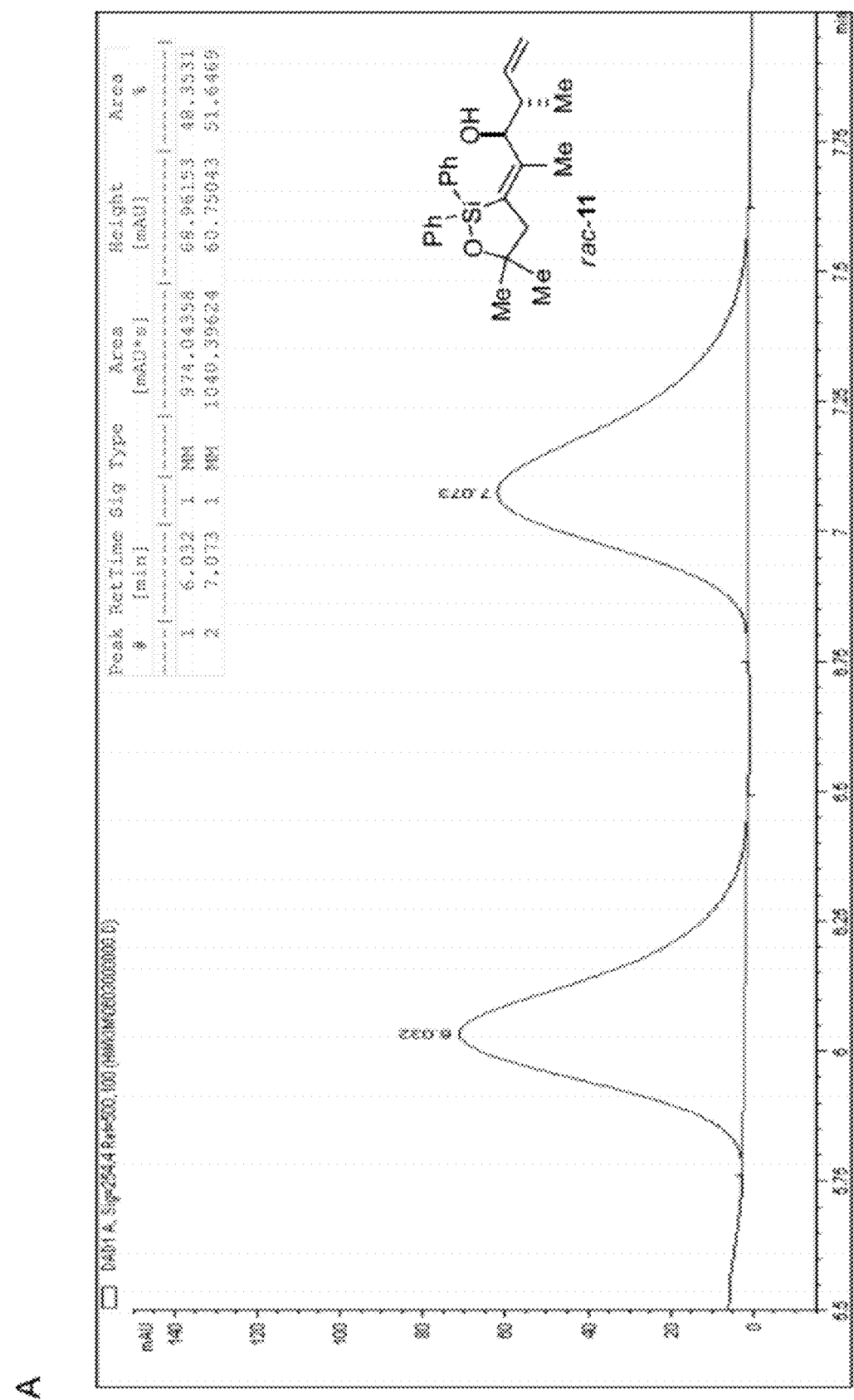
FIG. 18. The HPLC traces of (A) racemic 11, (B) (5R,6S)-11 produced using (R,R)-2 and Sc(OTf)$_3$ and (C) the oxidation product of (5R,6S)-11 from a Chiracel OD column, 2% i-PrOH in hexanes, 1 mL/min.

Finally, crotylation of aldehyde 4, one of the more sterically and electronically deactivated aldehydes relevant to polyketide natural product synthesis imaginable, was examined Reaction with (R,R)-2 and 5 mol % Sc(OTf)$_3$ (CH$_2$Cl$_2$, 23° C., 3 h) led to the isolation of 11 in 81% yield and 97% ee (Scheme 4; FIGS. 17 and 18). Alternatively, the unpurified reaction mixture may be submitted to a Tamao oxidation/diastereoselective tautomerization reaction (Spletstoser, J. T.; Zacuto, M. J.; Leighton, J. L. Org. Lett. 2008, 10, 5593; hereby incorporated by reference in its entirety) to provide 12 in 82% yield (with 8:1 diastereoselectivity for the stereocenter α to the ketone) (FIG. 19) and 97% ee (FIG. 18C). Thus, the Sc(OTf)$_3$-catalyzed crotylsilylation methodology described here has a substrate scope as broad as or broader than any other crotylation methodology, and enables crotylsilylation with substrates that are otherwise unreactive using other methods

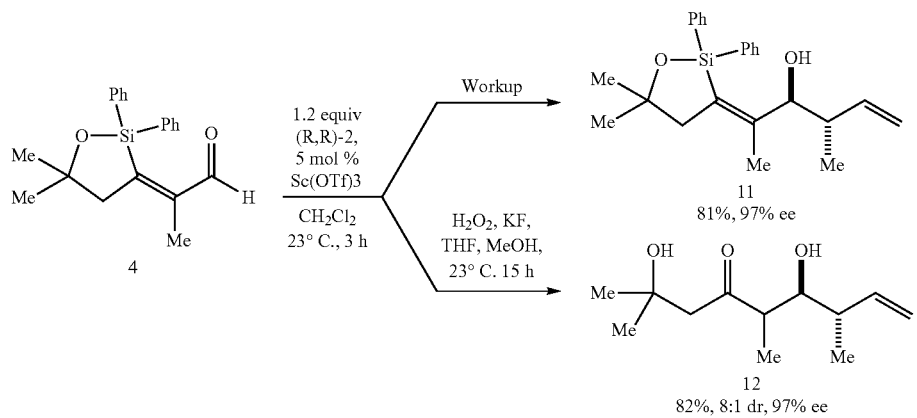

Figure 20A:
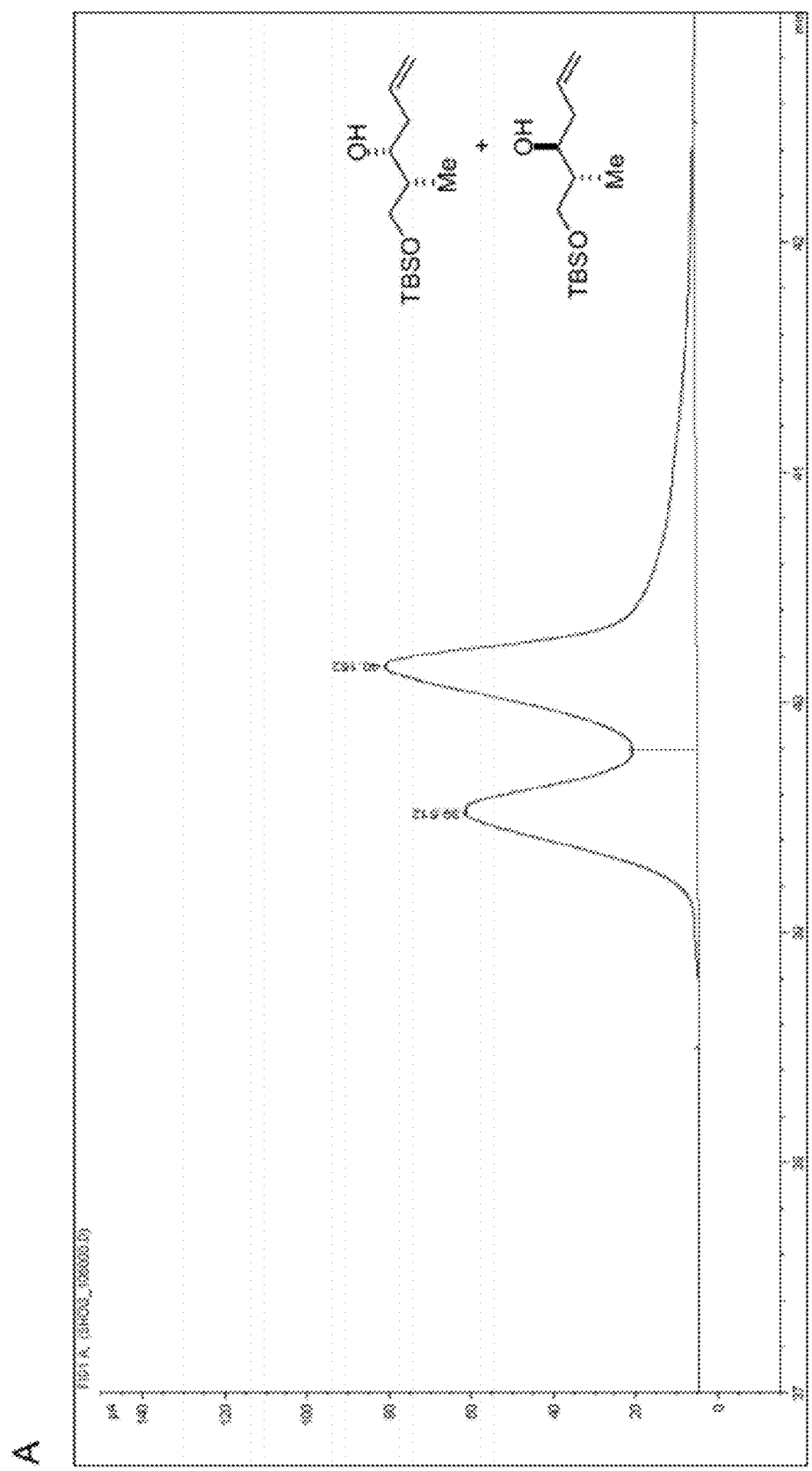
FIG. 20. The HPLC traces of (A) diastereomeric mixtures of allylation product of 7 produced using achiral allylation reagents and (B) allylation product of 7 produced using (S,S)-13 and Sc(OTf)$_3$ from a Supelco β-Dex 325 column, isothermal 110° C., 1 mL/min.
Figure 20B:
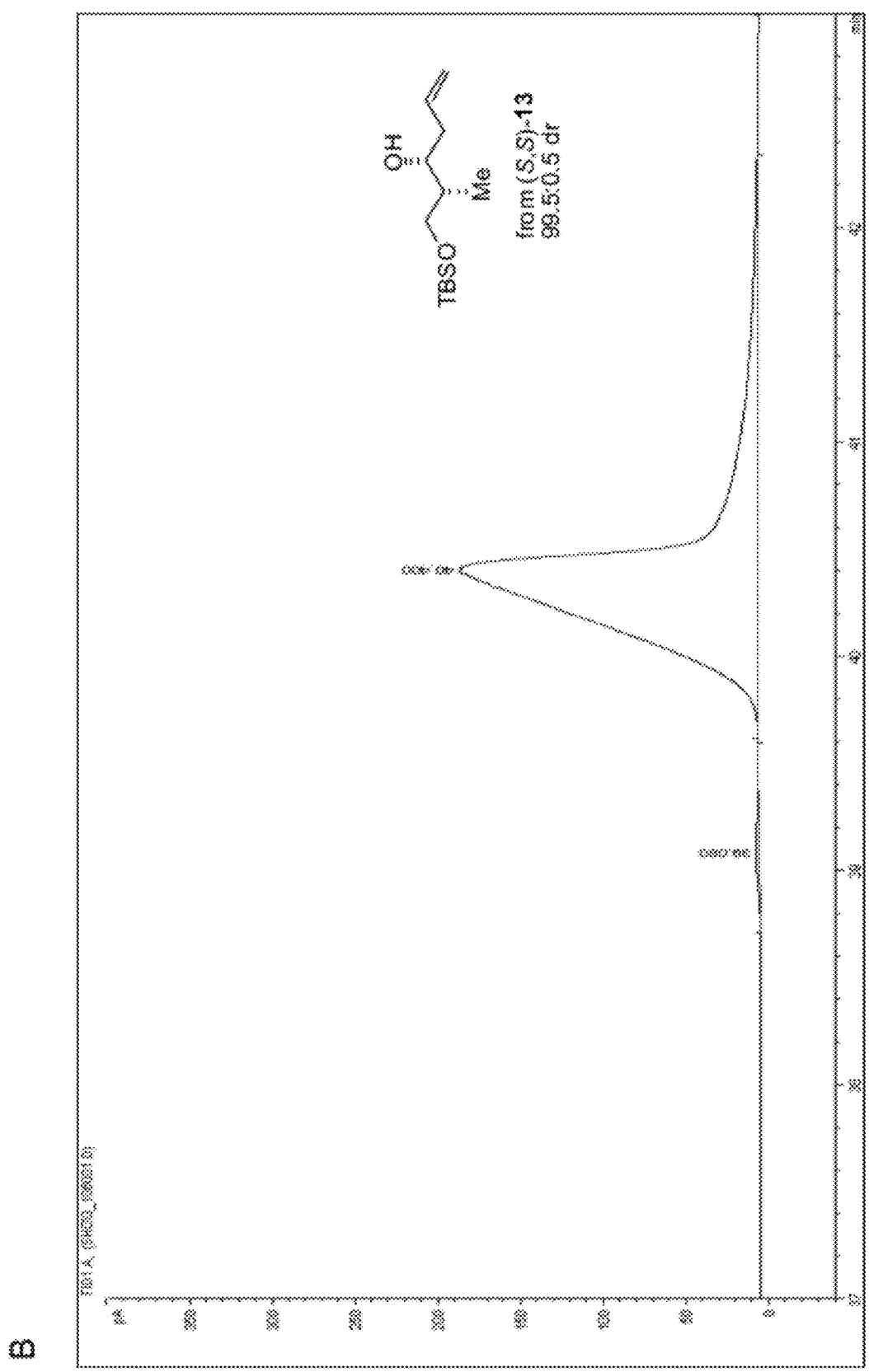
Figure 21A:
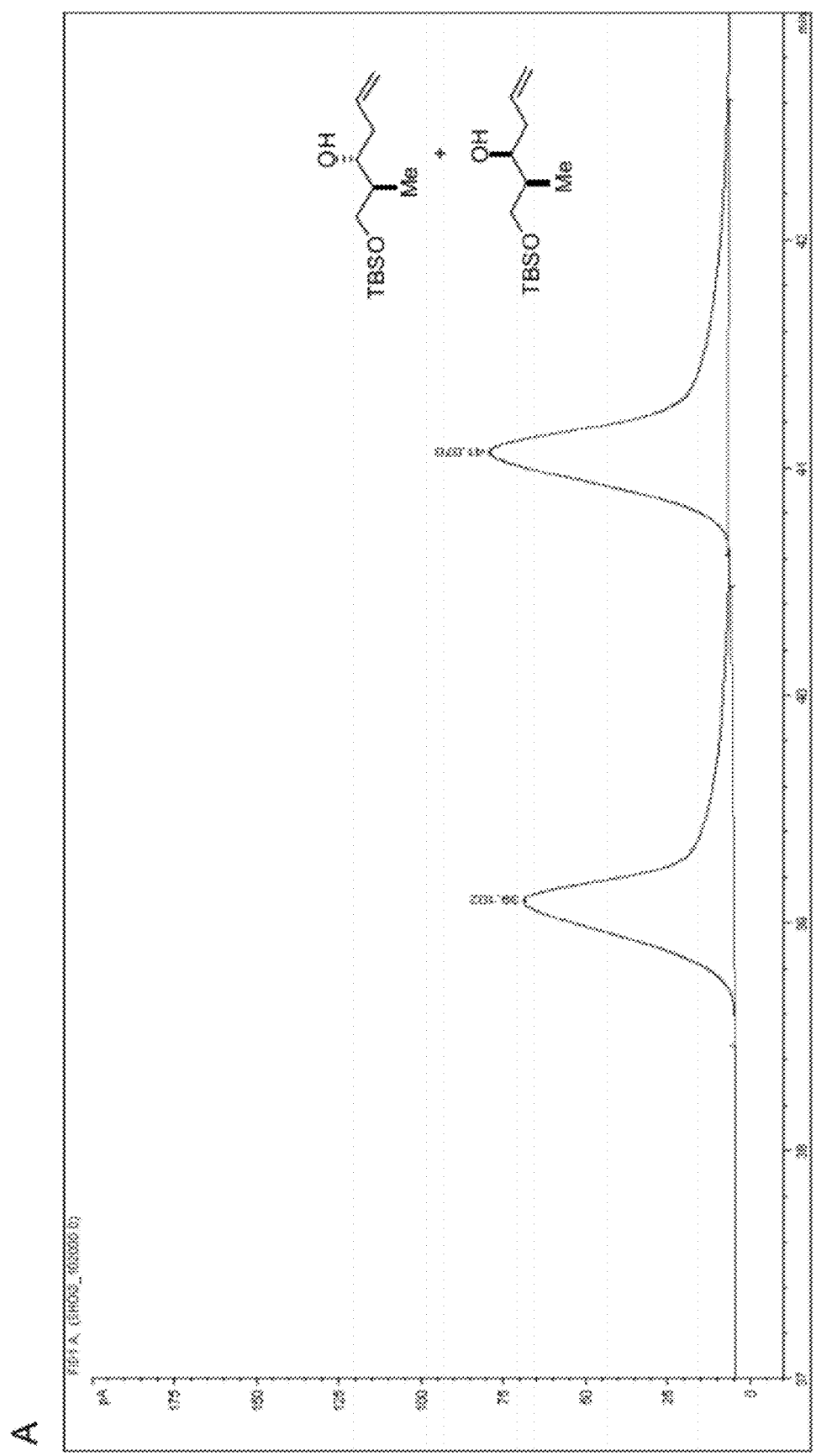
FIG. 21. The HPLC traces of (A) diastereomeric mixtures of allylation product of 8 produced using achiral allylation reagents and (B) allylation product of 8 produced using (S,S)-13 and Sc(OTf)$_3$ from a Supelco β-Dex 325 column, isothermal 110° C., 1 mL/min.
Figure 21B:
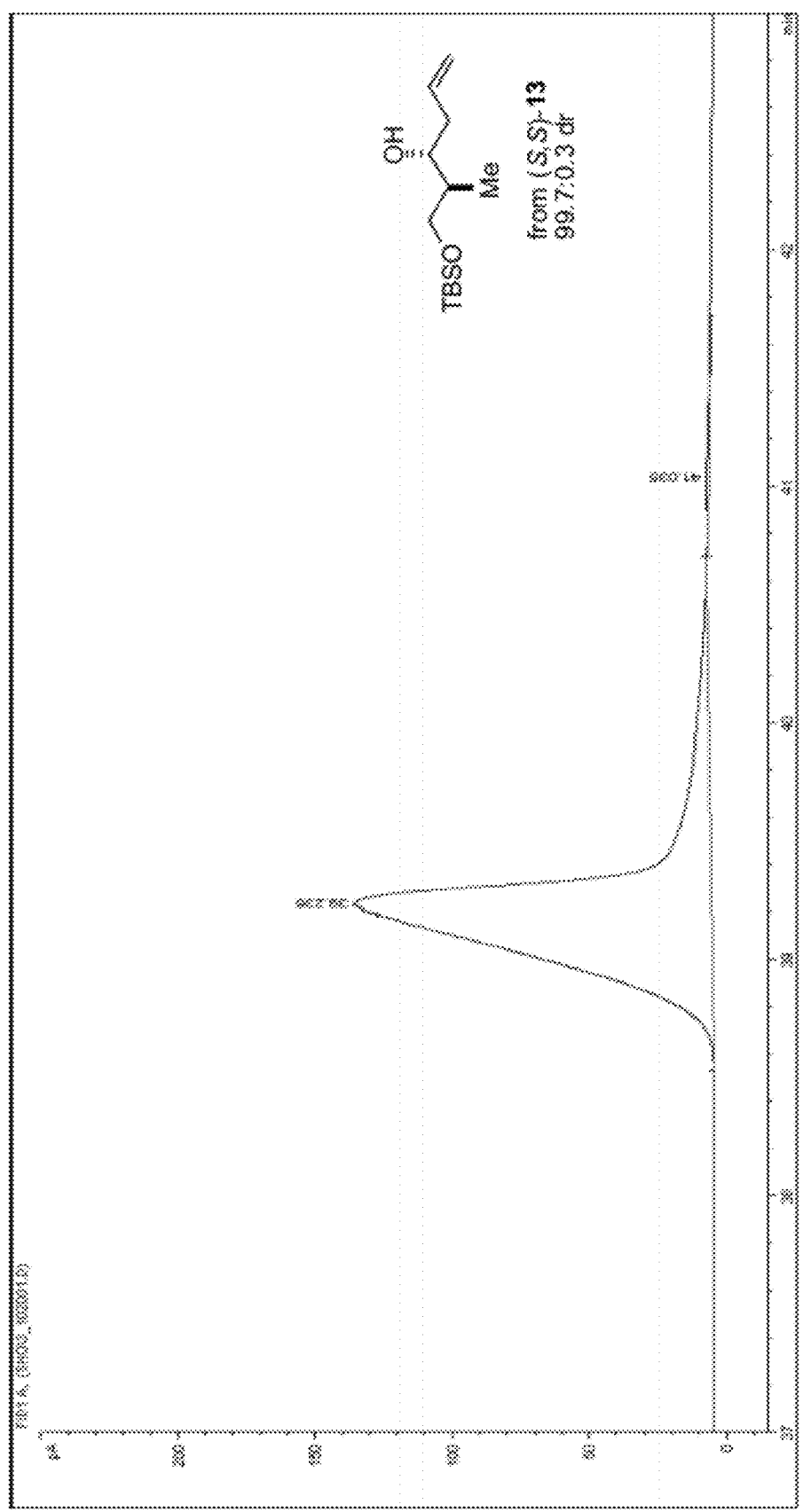

The allylation of aldehydes with allylsilane 13 is also effectively catalyzed by Sc(OTf)$_3$. Thus, treatment of aldehydes 7 and 8 with (S,S)-13 and 5 mol % Sc(OTf)$_3$ in CH$_2$Cl$_2$ at 0° C. for one hour led to the isolation of the illustrated products in 77% and 83% yields respectively, and in both cases with excellent levels (>99:1) of diastereoselectivity (Scheme 5; FIGS. 20 and 21). FIGS. 20A and 21A show reference diastereomeric mixtures of the allylation products, and FIGS. 20B and 21B show products obtained using the current invention.

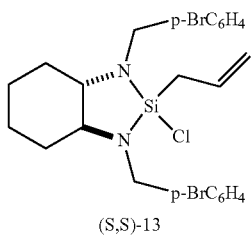

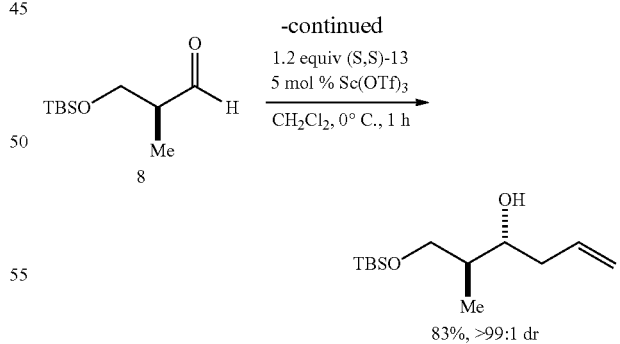

Figure 22:
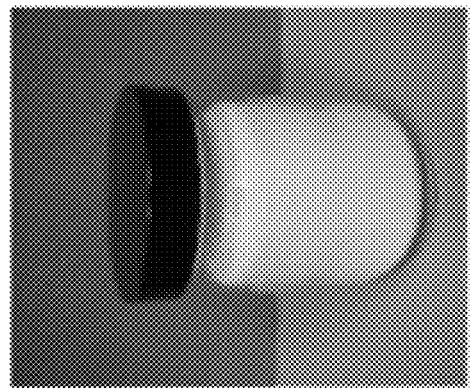
FIG. 22. Preparation of (R,R)-cis EZ-CrotylMix from (R,R)-1 and Sc(OTf)$_3$ in a 25:1 molar ratio.
Figure 23A:
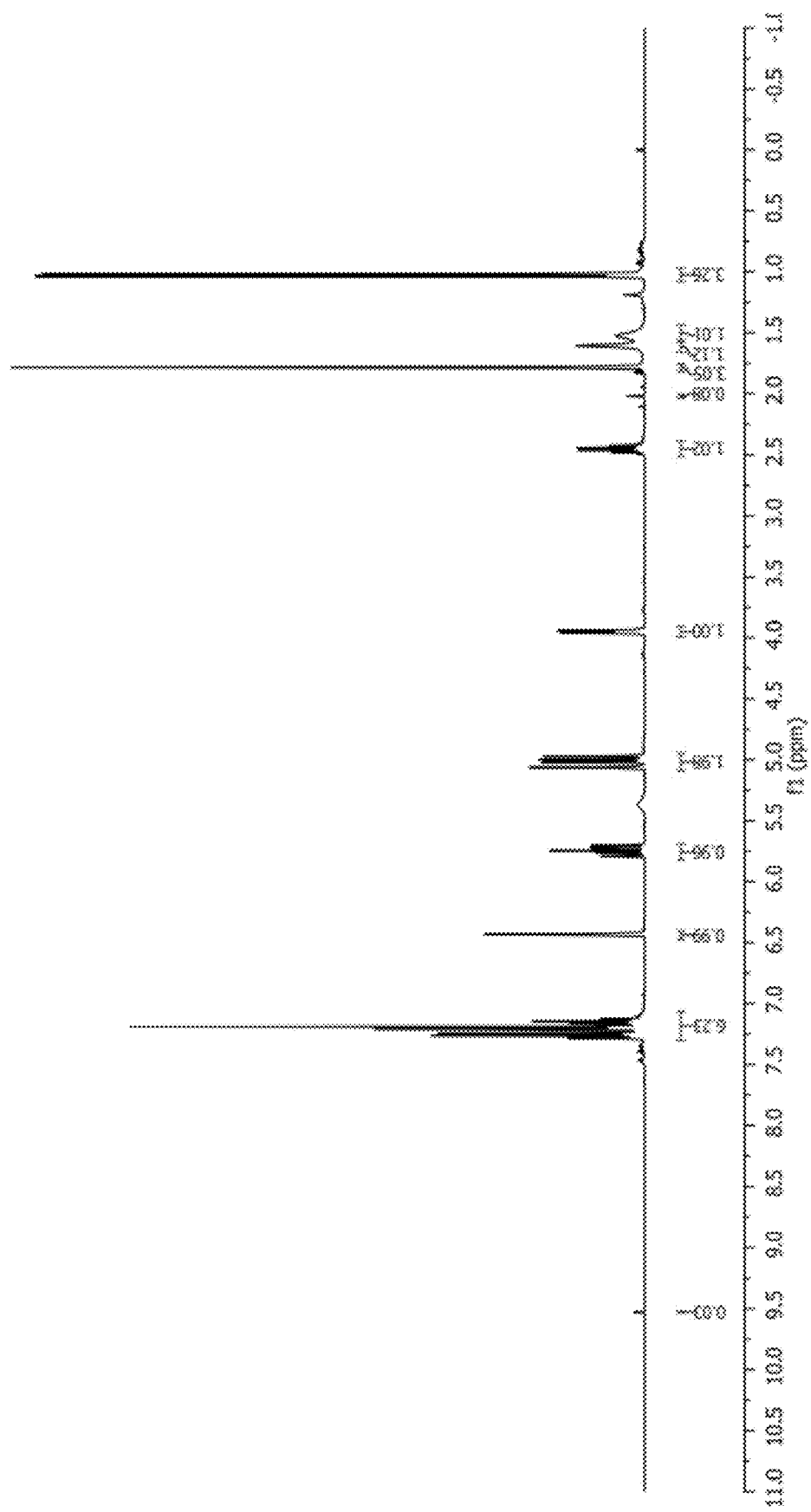
FIG. 23. The $^1$H NMR spectrum of (A) unpurified 5 and (B) chromatographically purified 5 in CDCl$_3$ from EZ-CrotylMix crotylation of α-methyl cinnamaldehyde.
Figure 23B:
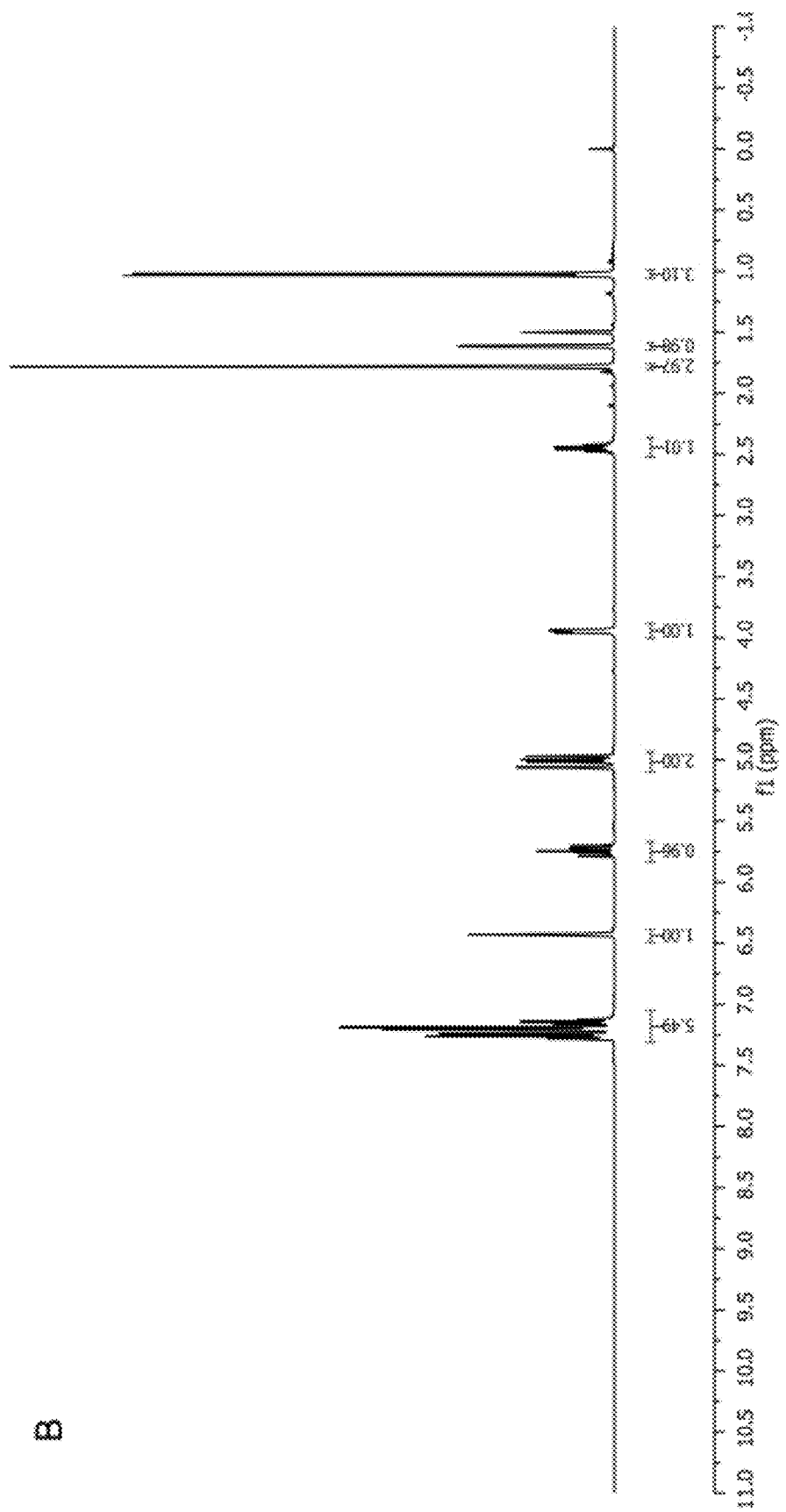

In order further to optimize the methodology and render the experimental procedures as straightforward as possible, mixtures (termed "EZ-CrotylMix") of the crotylsilanes and Sc(OTf)$_3$ in a 25:1 molar ratio were prepared (FIG. 22). The use of 650 mg of an EZ-CrotylMix to crotylate 1.0 mmol of an aldehdye corresponds to 1.1 equiv of the silane, and 4.4 mol % of Sc(OTf)$_3$ (Scheme 6). Thus, treatment of 1.0 mmol of α-methylcinnamaldehyde with 650 mg of (S,S)-cis EZ-CrotylMix (in CH$_2$Cl$_2$ at ambient temperature for 30 min) resulted in the isolation of 5 in 89% yield and 92% ee (FIG. 23).

Figure 18B:
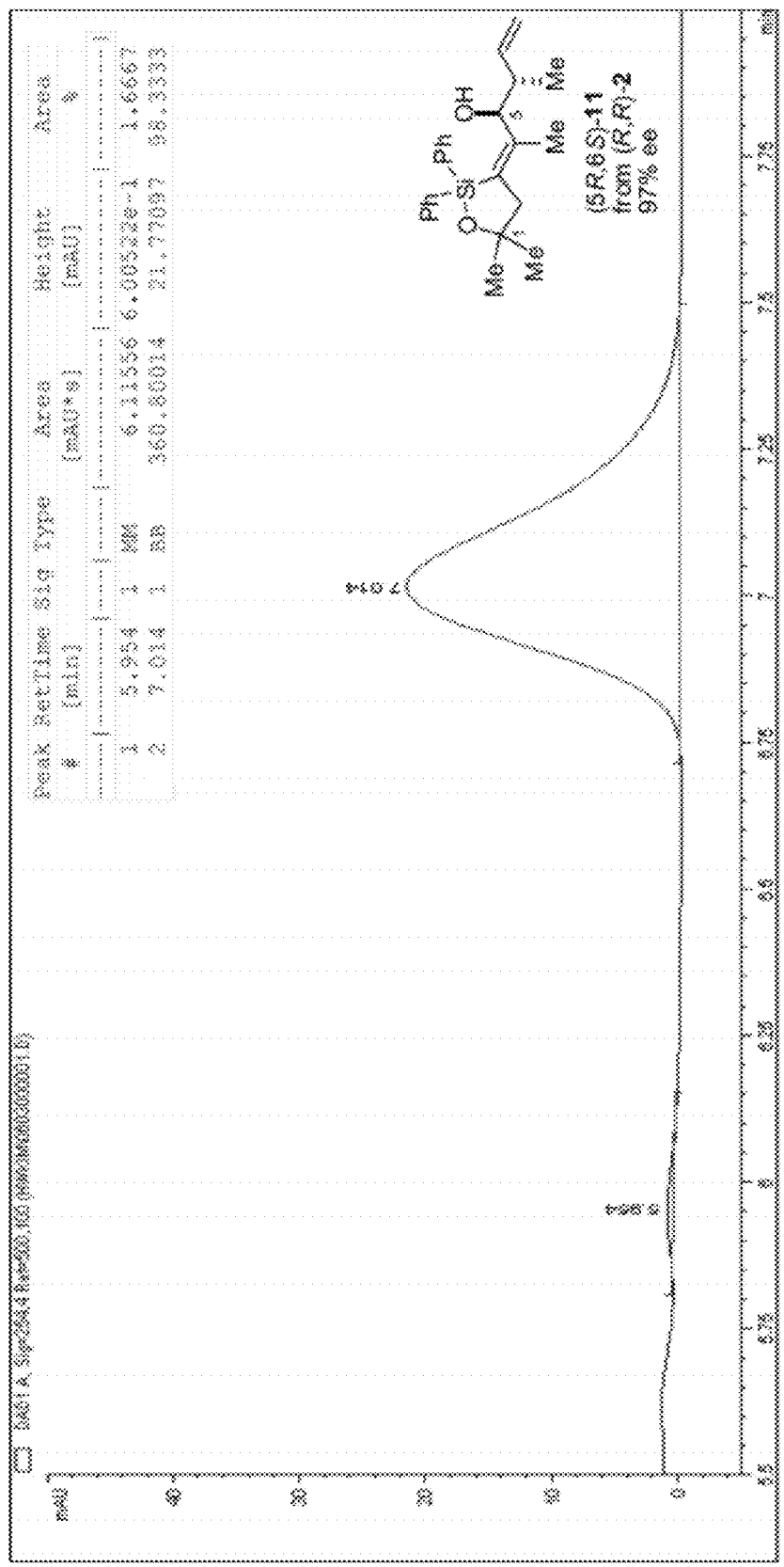
Figure 18C:
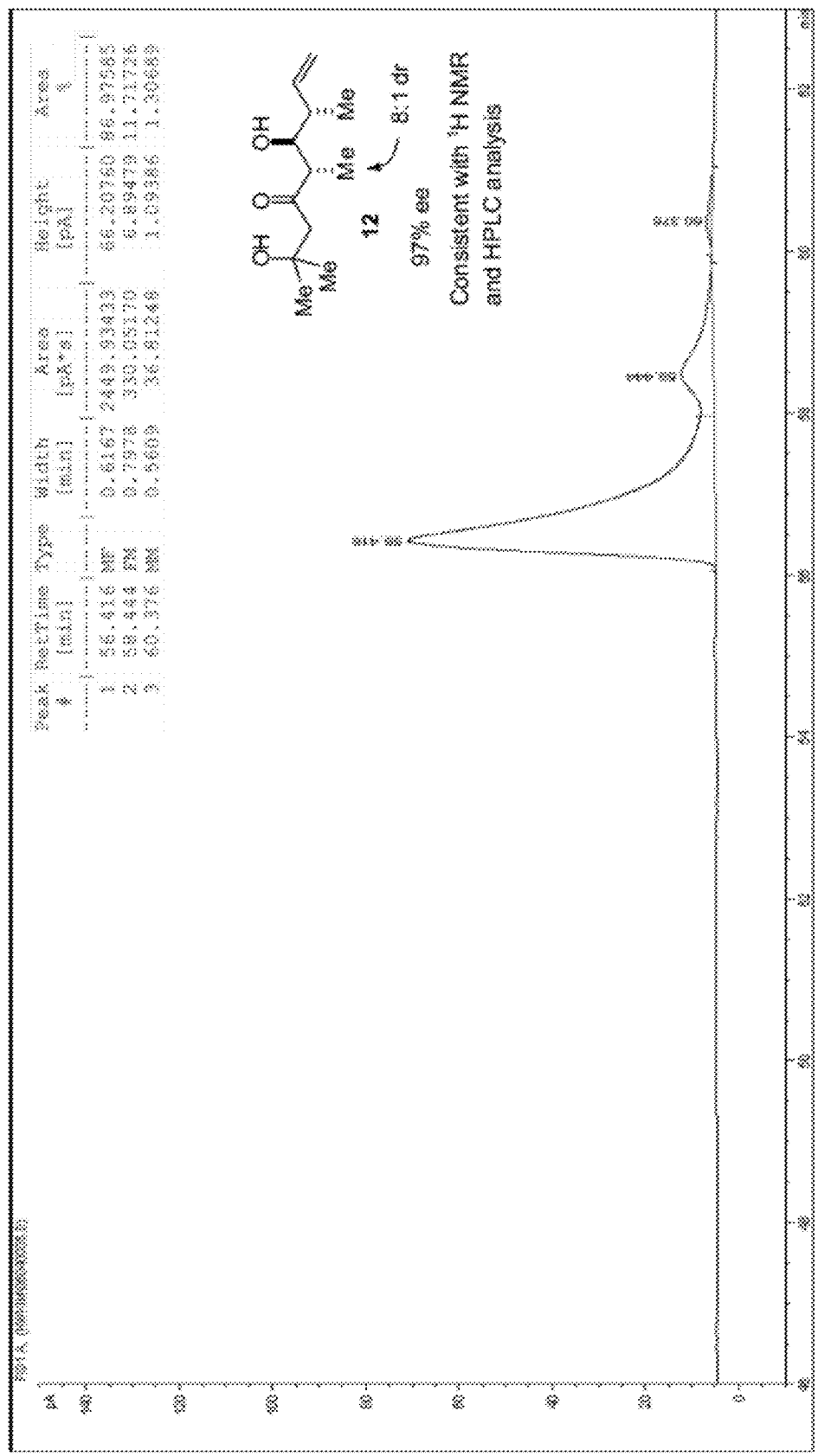

The EZ-CrotylMix stoichiometry using (R,R)-2 ((R,R)-trans EZ-CrotylMix) also sufficed for less reactive aldehyde 4, giving 11 in 85% yield and 97% ee (FIG. 18B). Additional Sc(OTf)$_3$ or EZ-CrotylMix may be added to the reactions of particularly unreactive aldehydes, but this EZ-CrotylMix formulation appears to be effective for most aldehydes.

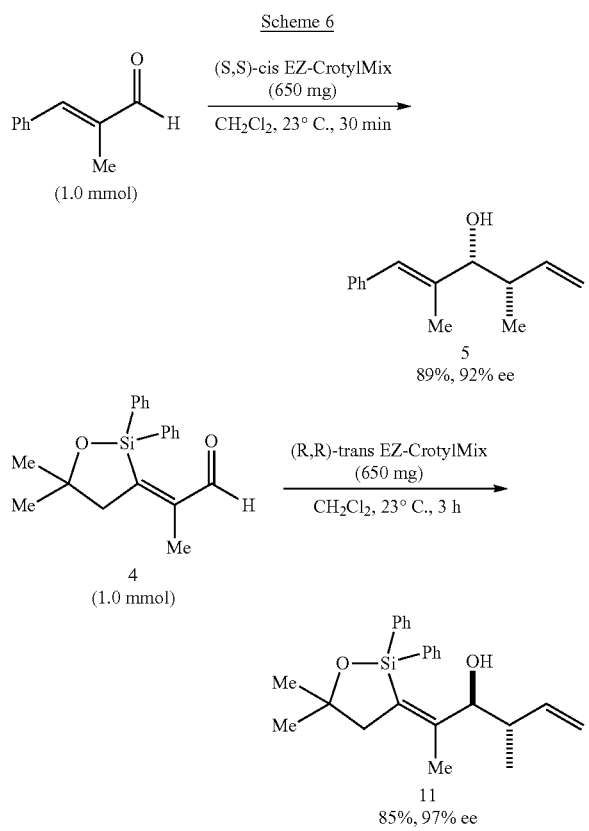

Scheme 6

Sc(OTf)$_3$ is an effective catalyst for the enantioselective crotylsilylation of aldehydes using silanes 1 and 2, and this has resulted in a dramatic increase in the scope of aldehydes that may be effectively crotylated using this methodology. That crotylsilanes 1 and 2 are crystalline solids has further facilitated the EZ-CrotylMix formulation, rendering this methodology the first comprehensive and highly practical solution to the enduring problem of enantioselective aldehyde crotylation.

As allylsilane 13 is also a crystalline solid, it too may be pre-mixed with the Sc(OTf)$_3$ in an analogous fashion, and the two resultant enantiomeric allylsilane/Sc(OTf)$_3$ mixtures may respectively be termed "(R,R)-EZ-AllylMix" and "(S,S)-EZ-AllylMix."

The following examples illustrate the present invention, and are set forth to aid in the understanding of the invention, and should not be construed to limit in any way the scope of the invention as defined in the claims which follow thereafter.

EXAMPLES

General Information.

All reactions were carried out under an atmosphere of nitrogen in flame-dried glassware with magnetic stirring unless otherwise indicated. All reaction solvents were purified by degassing with argon and passage through an activated alumina column. Z- and E-crotyltrichlorosilane were prepared according to literature procedures ((a) Tsuji, J.; Hara, M.; Ohno, K. *Tetrahedron Lett.* 1974, 30, 2143. (b) Furuya, N.; Sukawa, T. *J. Organomet. Chem.* 1975, 96, C1. (c) Kira, M.; Hino, T.; Sakurai, H. *Tetrahedron Lett.* 1989, 30, 1099. (d) Iseki, K.; Kuroki, Y.; Takahashi, M.; Kishimoto, S.; Kobayashi, Y. *Tetrahedron* 1997, 53, 3513. (e) Denmark S. E.; Fu, J. *J. Am. Chem. Soc.* 2001, 123, 9488. (f) Kotani, S.; Hashimoto, S.; Nakajima, M. *Tetrahedron* 2007, 63, 3122; each of which are also hereby incorporated by reference into this application in its entirety). $^1$H NMR spectra were recorded on a Bruker Avance III 400 (400 MHz) spectrometer. $^1$H NMR chemical shifts (δ) are reported in parts per million (ppm) relative to residual protiated solvent (CDCl$_3$, 7.26). Data are reported as follows: (br=broad singlet, s=singlet, d=doublet, t=triplet, q=quartet, m=multiplet, dd=doublet of doublets, td=triplet of doublets; integration; coupling constant(s) in Hz). Proton decoupled $^{13}$C NMR spectra were recorded on a Bruker Avance III 400 (100 MHz) spectrometer and are reported in ppm from CDCl$_3$ internal standard (77.23 ppm). HPLC analyses were performed on an Agilent 1200 Series HPLC, UV detection monitored at 254 nm, using a Chiralpak AD-H column (25 cm) or a Chiralcel OD column (25 cm). Gas chromatographic analyses were performed on a Hewlett-Packard 6890 Series GC equipped with a flame ionization detector (FID) using a Supelco β-Dex 325 (30 m×0.25 mm) capillary column. Optical rotations were recorded on a Jasco DIP-1000 digital polarimeter. High resolution mass spectra were obtained from the Mass Spectrometry Laboratory at Columbia University.

Example 1

Effect of Lewis Acids or Brønsted Acids on the Silane-Mediated Aldehyde Crotylation

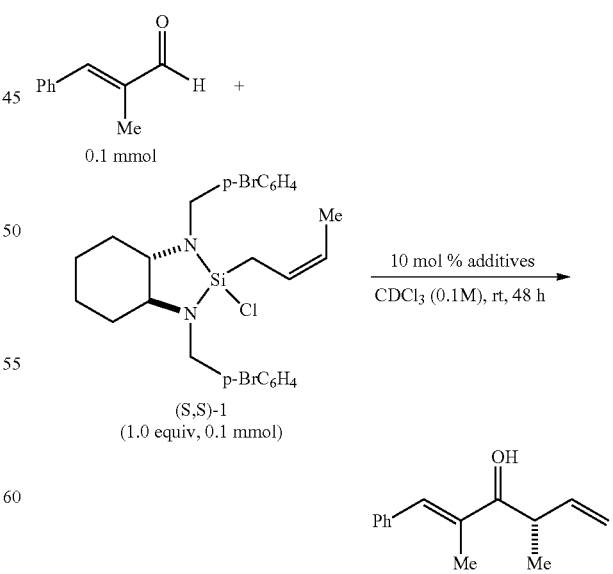

The additives resulted in the conversion and enantiomeric excesses shown in FIG. 1 and are listed according to the nature of the acid additives.

General Procedure for the Aldehyde Allylation and Crotylation

To a cooled (0° C.) solution of the aldehyde (0.30 mmol) in $CH_2Cl_2$ (3.0 mL, 0.1 M) was added reagent 1 or 2 (1.2 equiv, 0.36 mmol, 205 mg; for crotylation) or 13 (1.2 equiv, 0.36 mmol, 200 mg; for allylation) followed by $Sc(OTf)_3$ (0.05 equiv, 0.015 mmol, 7.4 mg). The mixture was stirred vigorously at 0° C. In most cases, the reaction was complete within 1 h as monitored by $^1H$ NMR spectroscopy.

HCl Workup:

The solvent was removed under reduced pressure. $Et_2O$ (5.0 mL, ethanol free) and 1.0 M HCl solution (3 mL) were added to the mixture, and stirred for 1 h. The white precipitate was filtered and dried to give the diamine dihydrochloride in 92-94% yield. The layers were separated and the aqueous layer was extracted with $Et_2O$ (2×5.0 mL). The combined organic layers were washed with sat $NaHCO_3$, dried over anhydrous $MgSO_4$, filtered, and concentrated. Purification of the residue by chromatography on silica gel afforded the product.

TBAF Workup:

Tetrabutylammonium fluoride (TBAF) trihydrate (1 equiv, 0.30 mmol, 95 mg) was added to the mixture. The solution was stirred for 30 min at ambient temperature. After concentrating the solvent, the residue was purified by chromatography on silica gel to afford the product.

For known compounds ((a) Hackman, B. M.; Lombardi, P. J.; Leighton, J. L. *Org. Lett.* 2004, 6, 4375. (b) Roush, W. R.; Grover, P. T. *J. Org. Chem.* 1995, 60, 3806. (c) Rauniyar, V.; Hall, D. G. *Angew. Chem., Int. Ed.* 2006, 45, 2426; each if which is also hereby incorporated by reference into this application in its entirety), HPLC or GC chromatograms are provided.

Example 2

Crotylation of α-Methylcinnamaldehyde Using (S,S)-1

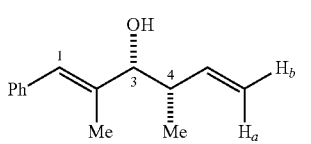

(3R,4S)-5

(S,S)-1 and HCl workup were used. Colorless oil, 87% Yield $^1H$ NMR (400 MHz, $CDCl_3$) (FIG. 2A): δ 7.39-7.23 (m, 5H, ArH), 6.54 (s, 1H, $C_1H$), 5.86 (ddd, J=17.4, 10.4, 7.3 Hz, 1H, $C_5H$), 5.15 (d, J=17.3 Hz, 1H, $C_6H_a$), 5.09 (d, J=10.5 Hz, 1H, $C_6H_b$), 4.06 (dd, J=6.4, 2.6 Hz, 1H, $C_3H$), 2.60-2.51 (m, 1H, $C_4H$), 1.89 (s, 3H, $C_2Me$), 1.72 (d, J=3.2 Hz, 1H, OH), 1.14 (d, J=6.8 Hz, 3H, $C_4\overline{Me}$). $^{13}C$ NMR (100 MHz, $CDCl_3$) (FIG. 2B): δ 141.1, 139.0, 137.9, 129.2, 128.3, 126.8, 126.6, 114.9, 81.1, 41.6, 14.7, 14.4. HRMS (FAB+): calculated for $C_{14}H_{17}O$ [M–H]⁻: 201.1279 found 201.1280. $[α]^{21}_D$ –21.4 (c 0.9, $CH_2Cl_2$).

Enantiomeric excess was determined by HPLC analysis (chiralcel OD column, 3% isopropanol in hexanes, 1.0 mL/min) (FIG. 4A): (3R,4S)-5, $t_R$=13.2 min, (3S,4R)-5, $t_R$=16.0 min.

Example 3

Crotylation of α-Methylcinnamaldehyde Using (S,S)-2

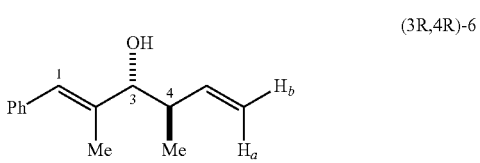

(3R,4R)-6

(S,S)-2 and HCl workup were used. Colorless oil, 87% Yield $^1H$ NMR (400 MHz, $CDCl_3$) (FIG. 3A): δ 7.39-7.23 (m, 5H, ArH), 6.52 (s, 1H, $C_1H$), 5.90-5.78 (m, 1H, $C_5H$), 5.24 (d, J=17.2 Hz, 1H, $C_6H_a$), 5.22 (d, J=10.1 Hz, 1H, $C_6H_b$), 3.88 (d, J=8.3 Hz, 1H, $C_3H$), 2.52-2.41 (m, 1H, $C_4H$), 1.93 (br. s, 1H, OH), 1.91 (s, 3H, $C_2Me$), 1.03 (d, J=6.8 Hz, 3H, $C_4Me$). $^{13}C$ NMR (100 MHz, $CDCl_3$) (FIG. 3B): δ. 141.1, 138.3, 137.7, 129.2, 128.3, 128.4, 126.7, 117.0, 81.8, 42.7, 17.1, 13.1. HRMS (FAB+): calculated for $C_{14}H_{17}O$ [M–H]⁻: 201.1279 found 201.1284. $[α]^{21}_D$ –40.9 (c 1.0, $CH_2Cl_2$).

Enantiomeric excess was determined by HPLC analysis (chiralcel OD column, 3% isopropanol in hexanes, 1.0 mL/min) (FIG. 4B): (3R,4R)-6, $t_R$=11.7 min, (3S,4S)-6, $t_R$=13.7 min.

Example 4

Crotylation of Aldehydes 7 and 8 Using (S,S)-1 and (S,S)-2

For crotylation of chiral aldehydes 7 and 8,[2c] TBAF workup was used. Diastereomeric ratios were determined by GC analysis (Supelco β-Dex 325 (30 m×0.25 mm) capillary column, isothermal 120° C., 1 mL/min) (FIGS. 13 and 14).

Example 5

Crotylation of Aldehyde 9 Using (S,S)-1

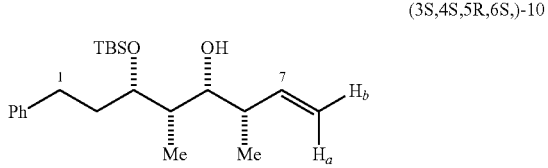

(3S,4S,5R,6S,)-10

(S,S)-1 and TBAF workup were used. Colorless oil, 80% Yield $^1H$ NMR (400 MHz, $CDCl_3$) (FIG. 15A): δ 7.31-7.24 (m, 2H, ArH), 7.22-7.12 (m, 3H, ArH), 5.64 (ddd, J=17.2, 10.3, 8.5 Hz, 1H, $C_7H$), 5.07 (ddd, J=17.2, 1.8, 0.9 Hz, 1H, $C_8H_a$), 5.02 (ddd, J=10.3, 1.8, 0.9 Hz, 1H, $C_8H_b$), 3.83-3.76 (m, 1H, $C_3H$), 3.46 (dd, J=8.6, 2.1 Hz, 1H, $C_5H$), 2.68 (br. s, 1H, OH), 2.62-2.53 (ddd, J=13.8, 10.1, 5.3 Hz, 1H, $C_1H$), 2.48 (ddd, J=13.8, 9.8, 6.9 Hz, 1H, $C_1H$), 2.38-2.27 (m, 1H, $C_6H$), 1.95-1.76 (m, 3H, $C_2H_2$, $C_4H$), 1.08 (d, J=6.6 Hz, 3H, Me), 0.91 (d, J=7.0 Hz, 3H, Me), 0.89 (s, 9H, TBS), 0.08 (s, 3H, TBS), 0.07 (s, 3H, TBS). $^{13}C$ NMR (100 MHz, $CDCl_3$) (FIG. 15B): δ. 142.0, 141.8, 128.7, 128.5, 126.1, 114.9, 78.5, 77.4, 42.4, 37.2, 36.5, 32.2, 26.1, 18.2, 17.0, 5.9, −3.5, −4.3. HRMS (FAB+): calcd for $C_{22}H_{39}O_2Si$ [M+H]$^+$: 363.2719. found 363.2718. $[\alpha]^{23}_D$ +24.4 (c 1.30, CHCl$_3$), Diastereomeric excess was determined by HPLC analysis (chiralpak AD-H column, 2% isopropanol in hexanes, 1.0 mL/min): (3S,4S,5S,6R)-10, $t_R$=3.7 min, (3S,4S,5R,6S)-10, $t_R$=4.5 min (FIG. 16).

Example 6

Procedure for the Stepwise Silylformylation, Crotylation, and Tamao Oxidation

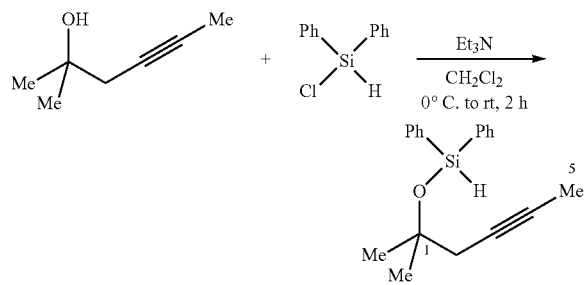

Figure 24A:
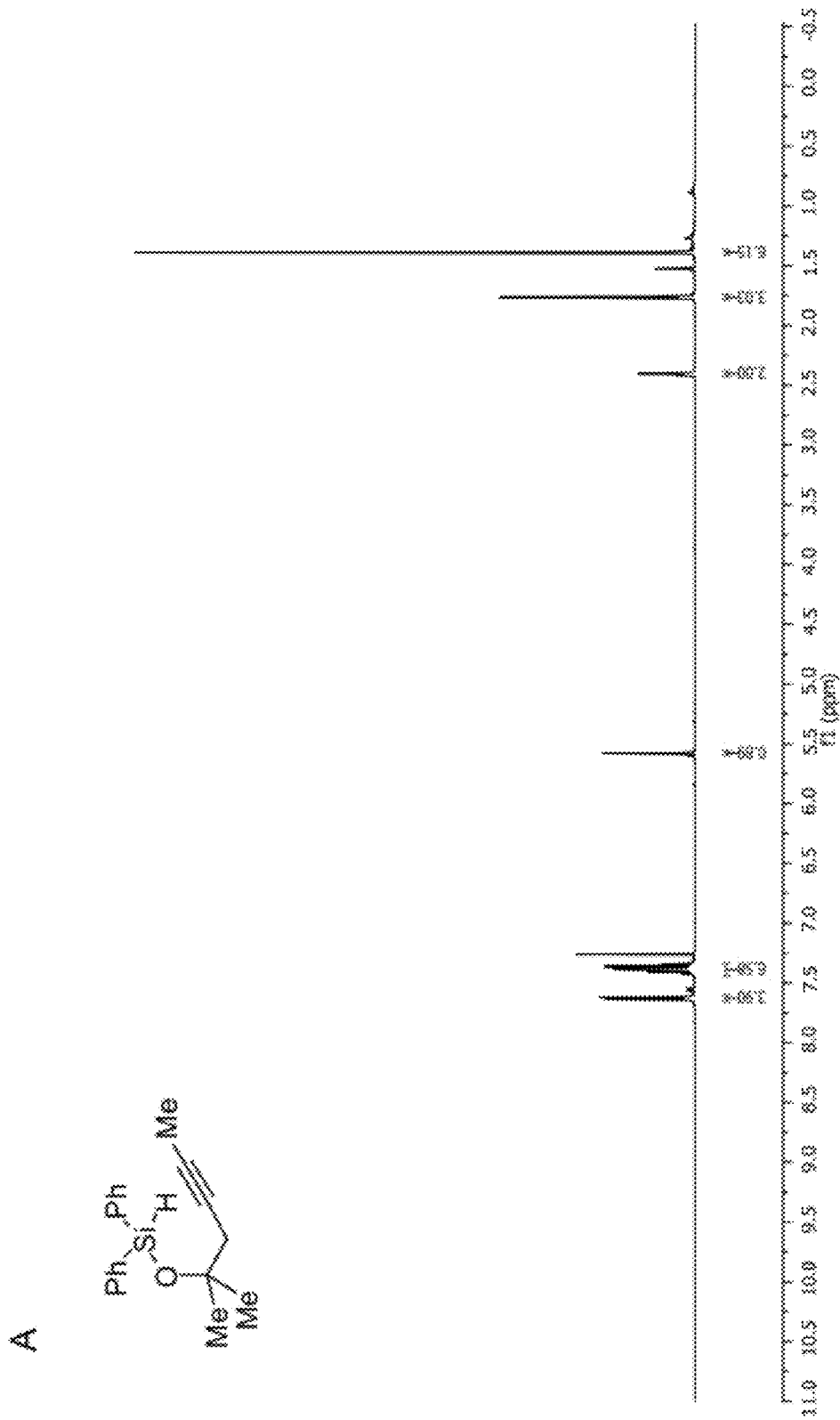
FIG. 24. The (A) $^1$H NMR spectrum and (B) $^{13}$C NMR spectrum of the alkyne precursor to aldehyde 4 in CDCl$_3$.
Figure 24B:
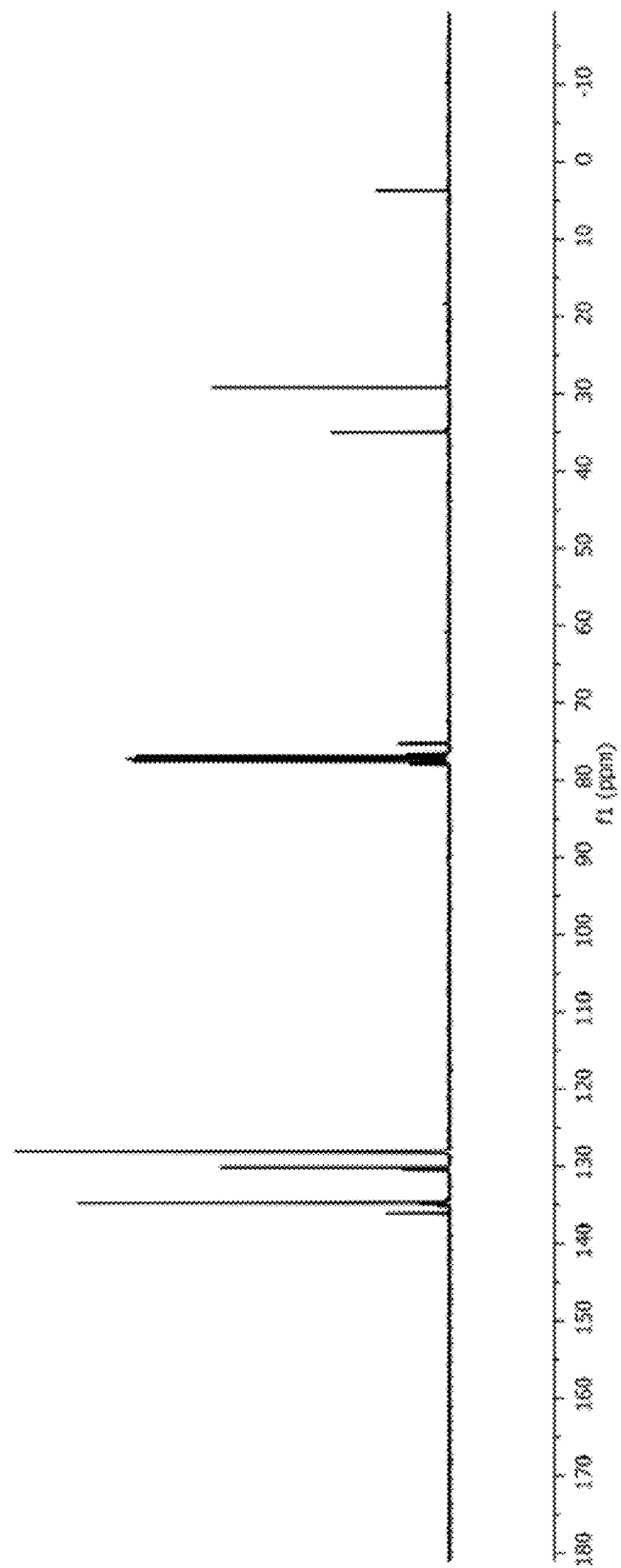

To a cooled (0° C.) solution of 2-methyl-4-heptyl-2-ol (9.27 mmol, 1.0 g) and chlorodiphenylsilane (1.1 equiv, 10.2 mmol, 2.2 g) in CH$_2$Cl$_2$ (18.7 mL, 0.5 M) was added Et$_3$N (2.0 equiv, 18.5 mmol, 2.6 mL). The mixture was allowed to warm to ambient temperature and stirred for 2 h. The solvent was concentrated under reduced pressure. The residue was diluted with hexanes (30 mL) and vigorously stirred for 30 min to ensure complete precipitation of Et$_3$N—HCl salts. The heterogeneous mixture was filtered through Celite, rinsing with hexanes (20 mL). After removing the solvent under reduced pressure, the residue was purified by chromatography on silica gel to yield the product as a colorless oil (2.49 g, 8.46 mmol, 91%). $^1$H NMR (400 MHz, CDCl$_3$) (FIG. 24A): δ 7.64-7.62 (m, 4H, ArH), 7.41-7.34 (m, 6H, ArH), 5.58 (s, 1H, SiH), 2.41 (q, J=2.5 Hz, 2H, C$_2$H), 1.76 (t, J=2.5 Hz, 3H, —C≡C-Me), 1.39 (s, 6H, C$_1$Me$_2$). $^{13}$C NMR (100 MHz, CDCl$_3$) (FIG. 24B): δ 136.1, 134.7, 130.1, 128.1, 77.9, 76.6, 75.3, 35.0, 29.2, 3.7. HRMS (FAB+): calcd for $C_{19}H_{21}OSi$ [M−H]$^-$: 293.1362. found 293.1371.

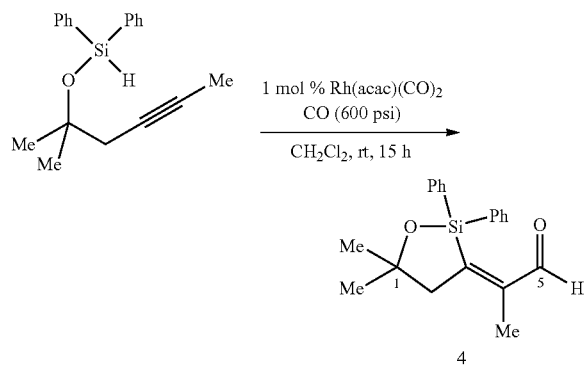

Figure 25A:
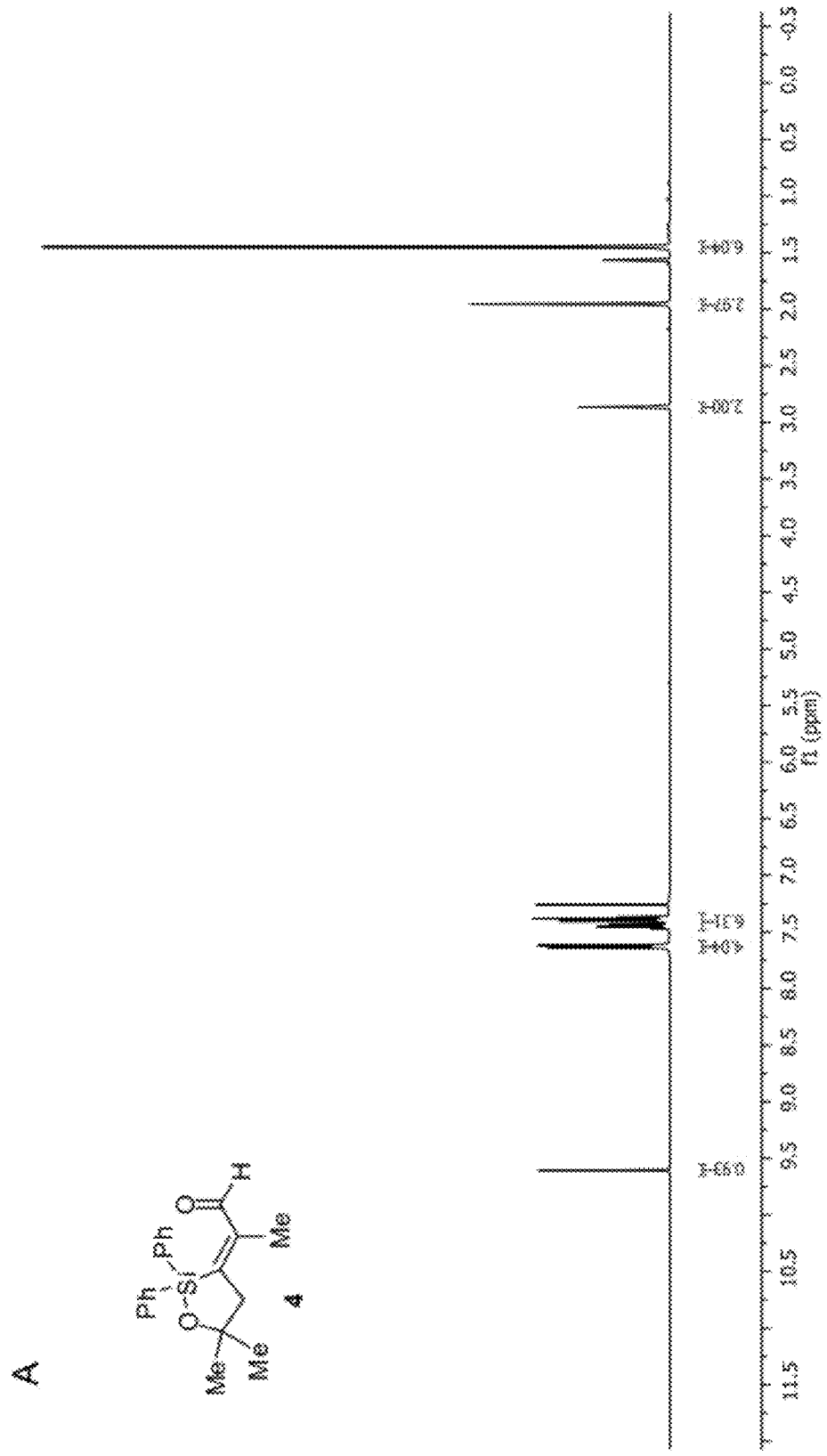
FIG. 25. The (A) $^1$H NMR spectrum and (B) $^{13}$C NMR spectrum of aldehyde 4 in CDCl$_3$.
Figure 25B:
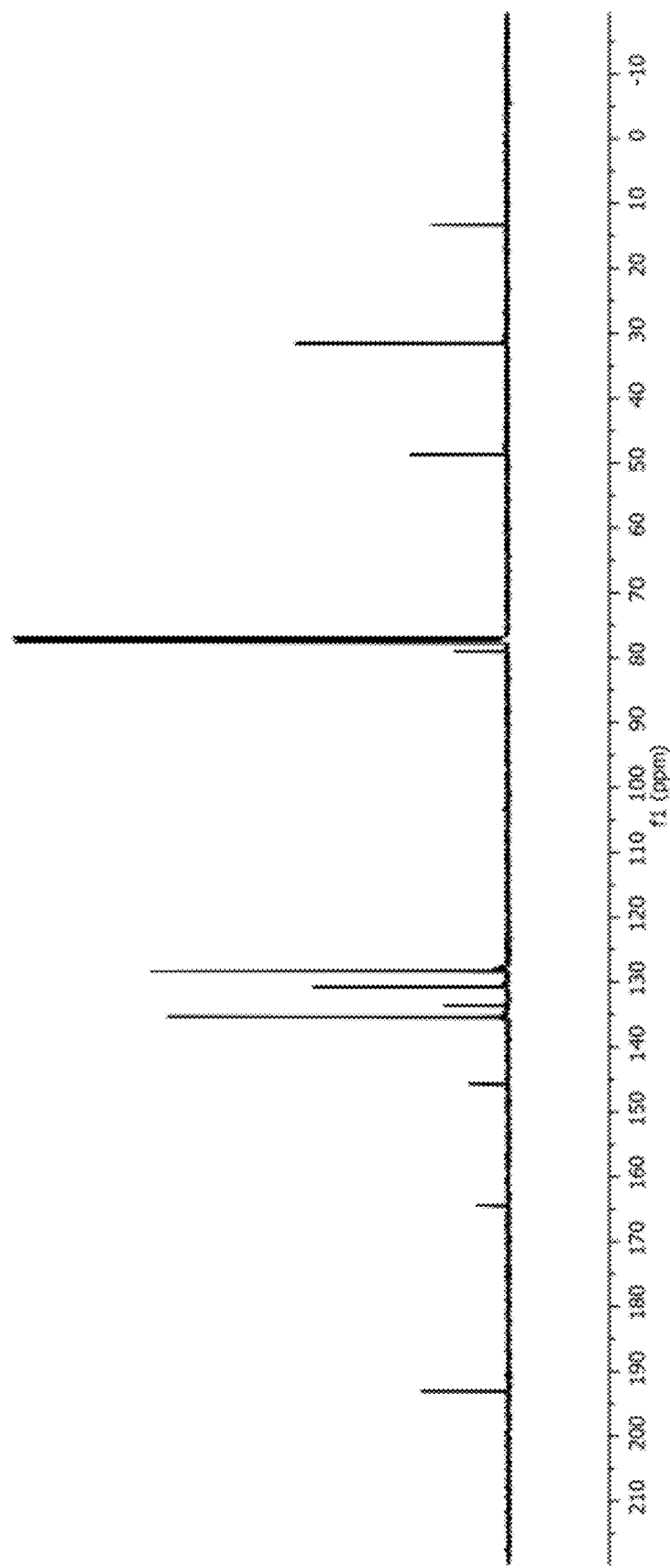
Figure 26A:
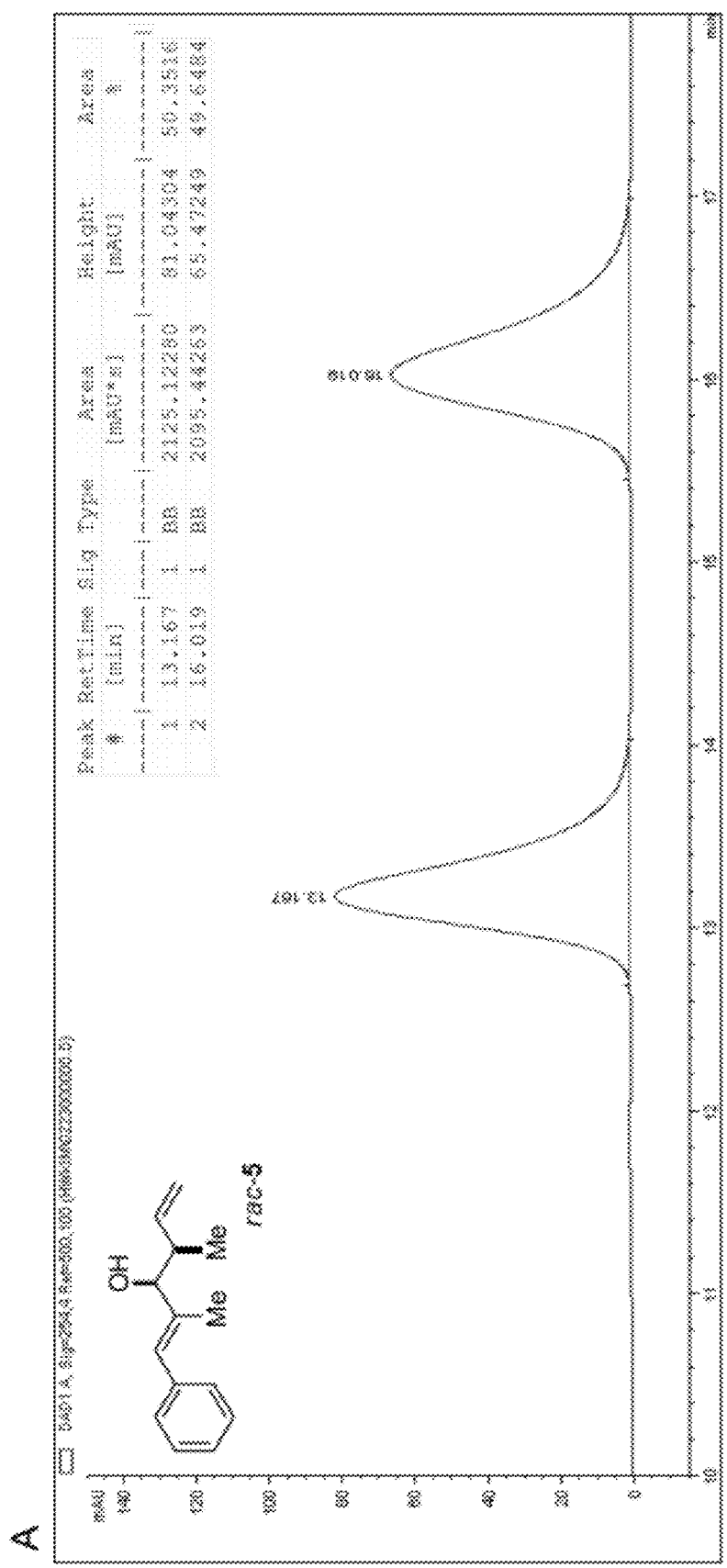
FIG. 26. The HPLC traces of (A) racemic 5, (B) racemic 6 and (C) a mixture of racemic 5 and racemic 6 from a Chiracel OD column, 3% i-PrOH in hexanes, 1 mL/min.
Figure 26B:
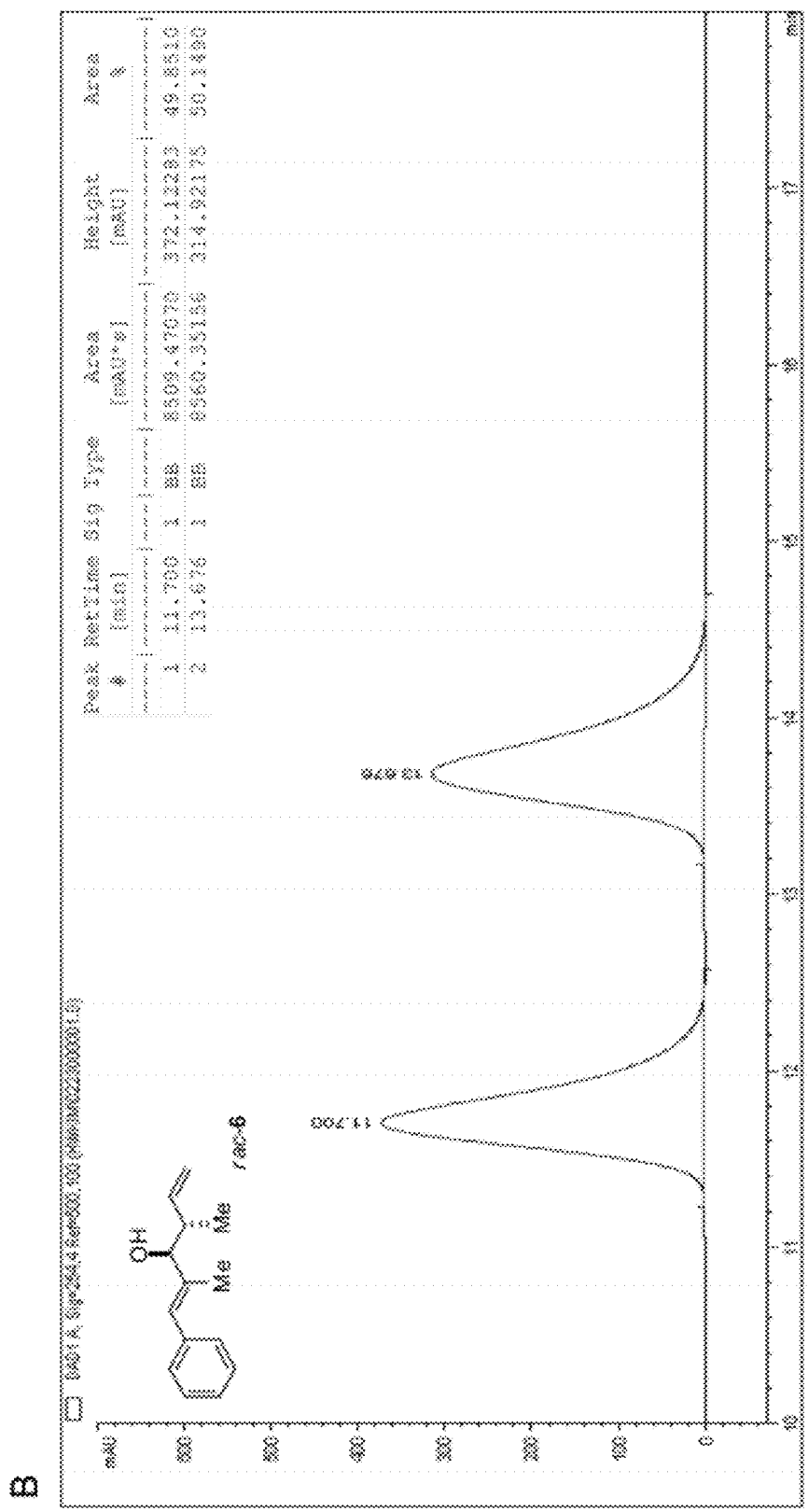
Figure 26C:
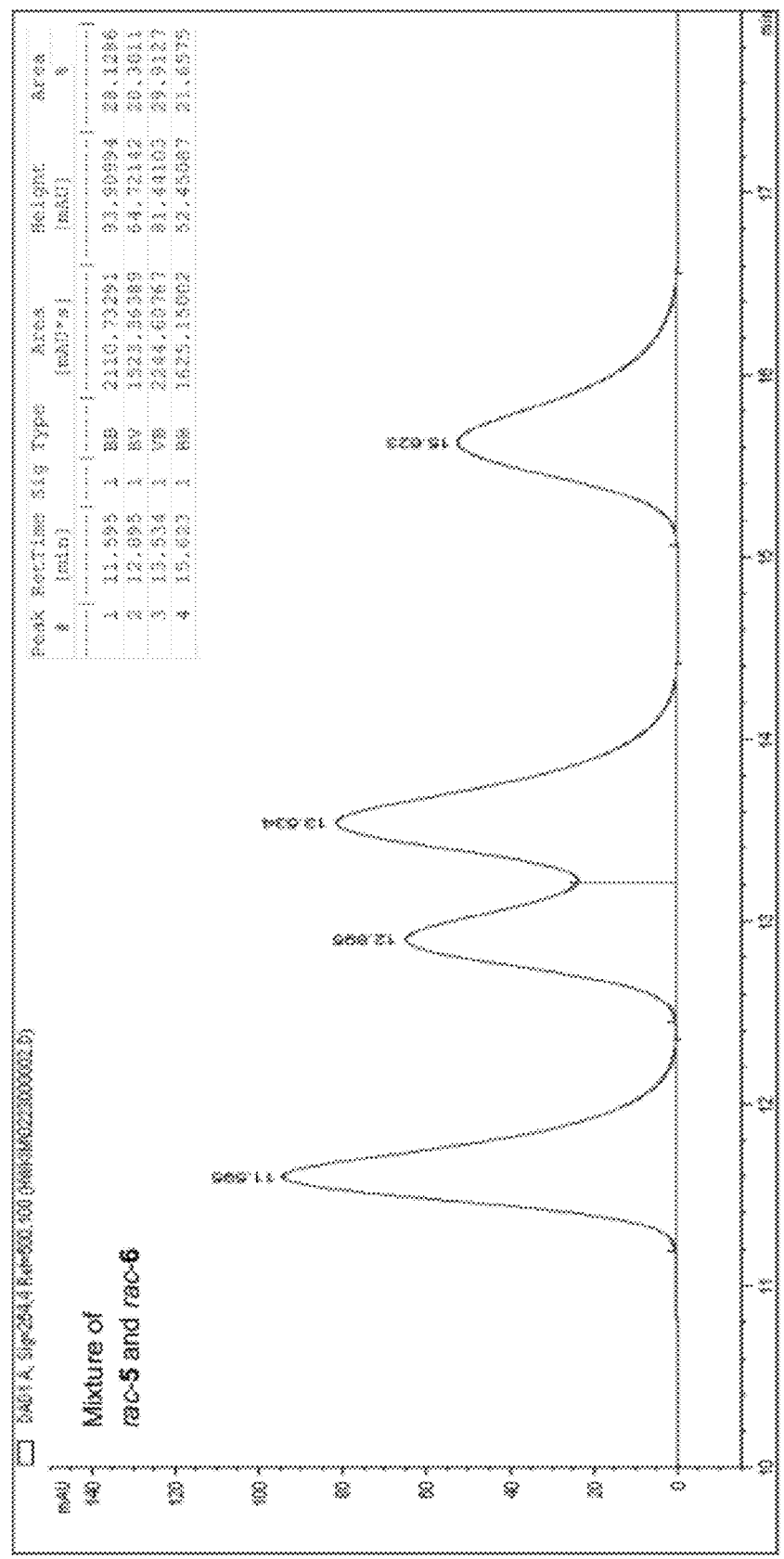

To a bomb reactor equipped with a glass liner and a stir bar was added the substrate (6.0 mmol, 1.77 g) in CH$_2$Cl$_2$ (15 mL, 0.40 M). After adding Rh(acac)(CO)$_2$ (1.0 mol %, 0.060 mmol, 15 mg), the bomb was assembled and charged to 300 psi of CO and vented. This purge was repeated twice and finally the bomb was charged to 600 psi of CO. After stirring for 15 h, the bomb was vented and opened. The solution was evaporated under reduced pressure. The residue was dissolved in pentane (20 mL) and filtered through dry Celite. Evaporation of solvent provided the product as a brown viscous oil (99%, 5.94 mmol). $^1$H NMR (400 MHz, CDCl$_3$) (FIG. 25A): δ 9.61 (s, 1H, CHO), 7.64-7.62 (m, 4H, ArH), 7.47-7.37 (m, 6H, ArH), 2.86 (s, 2H, C$_2$H), 1.96 (s, 3H, C$_4$Me), 1.45 (s, 6H, C$_1$Me$_2$). $^{13}$C NMR (100 MHz, CDCl$_3$) (FIG. 25B): δ 193.0, 164.4, 145.6, 135.4, 133.7, 130.8, 128.4, 79.0, 48.8, 31.5, 13.4. HRMS (FAB+): calcd for $C_{20}H_{23}O_2Si$ [M+H]$^+$: 323.1467. found 323.1477.

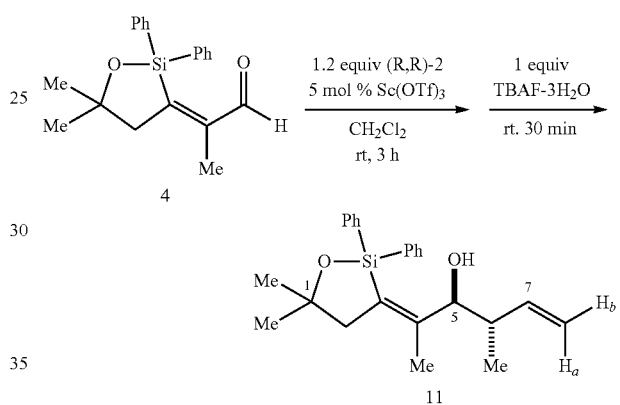

To a solution of the crude aldehyde (0.18 mmol, 57 mg) in CH$_2$Cl$_2$ (1.8 mL) was added (R,R)-2 (1.2 equiv, 0.21 mmol, 121 mg) followed by Sc(OTf)$_3$ (0.05 equiv, 0.0089 mmol, 4.4 mg). The mixture was stirred vigorously for 3 h at ambient temperature. TBAF.3H$_2$O (1 equiv, 0.18 mmol, 56 mg) was added to the mixture. The solution was stirred for 30 min at ambient temperature. Purification of the residue by chromatography on silica gel afforded the product as a clear oil (54 mg, 81%). $^1$H NMR (400 MHz, CDCl$_3$) (FIG. 17A): δ 7.78-7.76 (m, 2H, ArH), 7.58-7.56 (m, 2H, ArH), 7.44-7.33 (m, 6H, ArH), 5.73-5.67 (m, 1H, C$_7$H), 5.00 (d, J=17.3 Hz, 1H, C$_8$H$_a$), 4.89 (dd, J=10.3, 1.9 Hz, 1H, C$_8$H$_b$), 4.75 (s, 1H, C$_5$H), 2.71-2.64 (m, 1H, C$_6$H), 2.52 (s, 2H, C$_2$H), 1.81 (s, 3H, C$_4$Me), 1.28 (d, J=6.9 Hz, 3H, C$_6$Me), 1.10 (s, 3H, C$_1$Me), 0.96 (s, 3H, C$_1$Me). $^{13}$C NMR (100 MHz, CDCl$_3$) (FIG. 17B): δ 156.9, 139.5, 136.4, 135.8, 135.5, 134.5, 130.2, 129.0, 128.1, 127.9, 115.1, 89.1, 71.7, 42.9, 41.8, 30.2, 29.5, 17.9, 14.6. HRMS (FAB+): calcd for $C_{24}H_{31}O_2Si$ [M+H]$^+$: 379.2093. found 379.2102. $[\alpha]^{19}_D$ +55.4 (c 0.7, CH$_2$Cl$_2$).

Diastereomeric excess was determined by HPLC analysis (chiralcel OD column, 2% isopropanol in hexanes, 1.0 mL/min): (5S,6R)-11, $t_R$=6.0 min, (5R,6S)-11, $t_R$=7.1 min (FIG. 18).

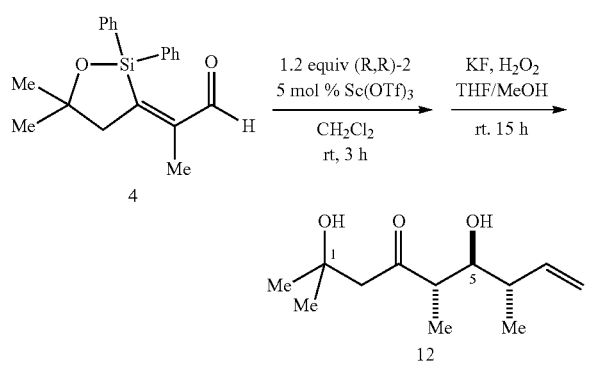

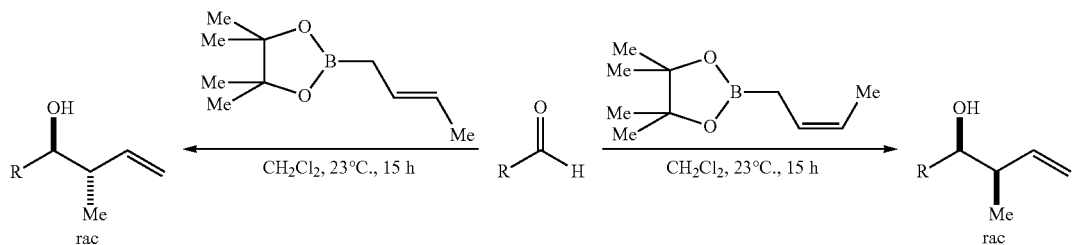

Compound 12 was previously characterized (Spletstoser, J. T.; Zacuto, M. J. Leighton, J. L. *Org. Lett.* 2008, 10, 5593; hereby incorporated by reference in its entirety).

To a solution of the crude aldehyde (0.45 mmol, 146 mg) in $CH_2Cl_2$ (4.5 mL) was added (R,R)-2 (1.2 equiv, 0.54 mmol, 309 mg) followed by $Sc(OTf)_3$ (0.05 equiv, 0.023 mmol, 11.3 mg). The mixture was stirred vigorously for 3 h at ambient temperature. The solvent was removed under reduced pressure. The residue was dissolved in THF (3.0 mL) and MeOH (3.0 mL). After adding KF (5 equiv, 2.3 mmol, 134 mg) and 30% $H_2O_2$ solution (10 equiv, 510 μL), the mixture was stirred for 15 h at ambient temperature. The solution was diluted with distilled water (20 mL) and extracted with EtOAc (3×20 mL). The combined organic layers were dried over $MgSO_4$, filtered, and concentrated. Purification of the residue by flash chromatography on silica gel afforded the product as a colorless oil (80 mg, 82%). $[\alpha]^{19}_D$ −7.4 (c 0.8, $CH_2Cl_2$).

Figure 19A:
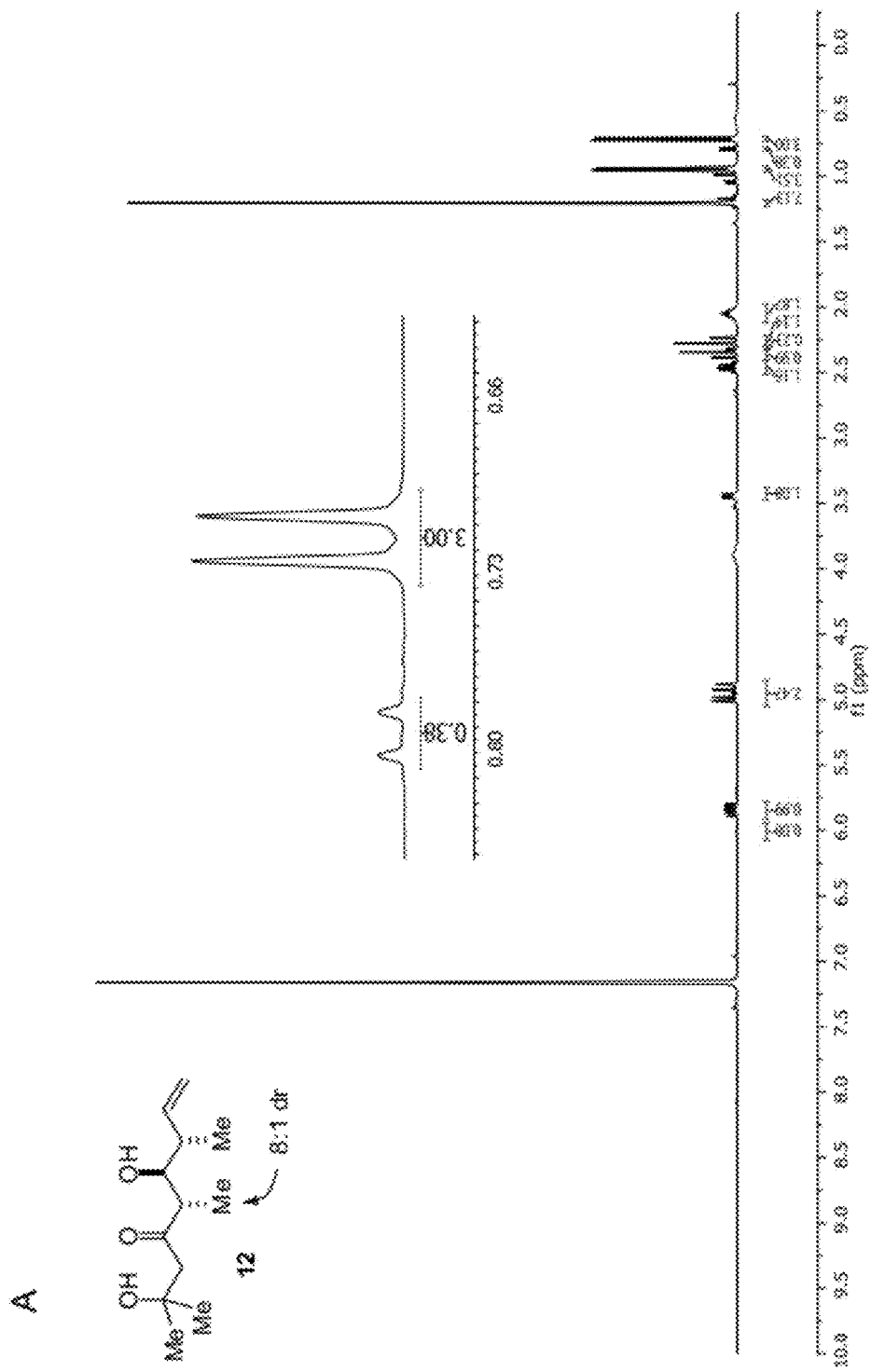
FIG. 19. The (A) $^1$H NMR spectrum and (B) $^{13}$C NMR spectrum of 12 in C$_6$D$_6$.
Figure 19B:
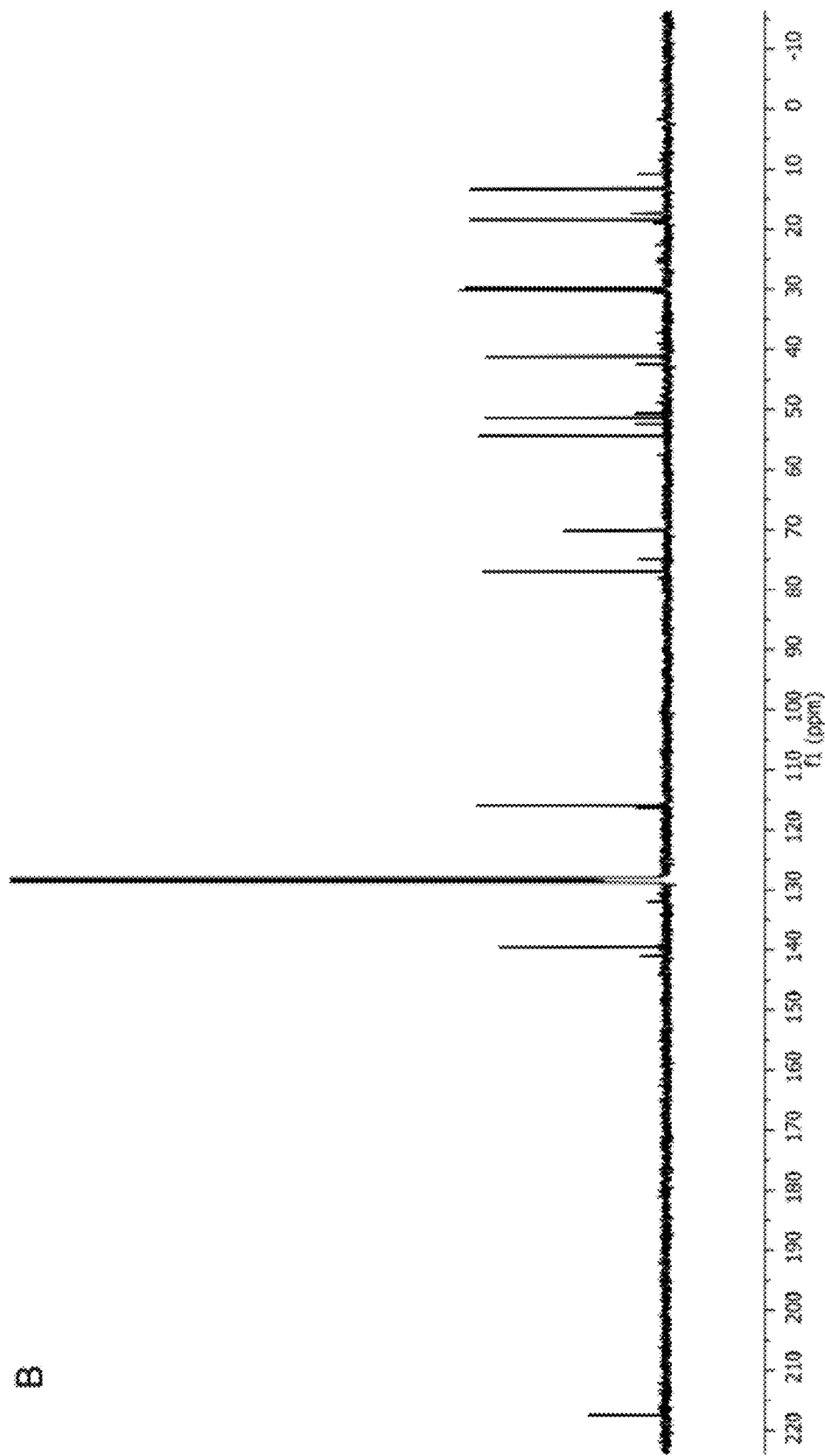

Diastereomeric ratio was initially determined from $^1H$ NMR spectra in $C_6D_6$ (FIG. 19).

Enantiomeric excess and diastereomeric ratio were determined by GC analysis (Supelco β-Dex 325 (30 m×0.25 mm) capillary column, isothermal 120° C., 1 mL/min): (4S,5S, 6S)-12, $t_R$=56.4 min, (4R,5S,6S)-12, $t_R$=58.5 min, (4R,5R, 6R)-12, $t_R$=60.4 min (FIG. 18C).

Example 7

Procedure for Aldehyde Crotylation Using Ez-CrotylMix

To a solution of 650 mg of (S,S)-cis EZ-CrotylMix in 10 mL of $CH_2Cl_2$ (0.1 M) was added 1 mmol of α-methyl cinnamaldehyde. The mixture was stirred vigorously for 30 min, and then concentrated. The residue was treated with $Et_2O$ (5 mL) and 1 M HCl (5 mmol, 5 mL), and the resulting mixture was stirred vigorously for 1 h. The mixture was filtered (with $Et_2O$ washes) to recover the diamine as its bis HCl salt (in 95% yield) and the layers of the biphasic filtrate were separated. The aqueous phase was extracted with $Et_2O$, and the combined organic phases were dried ($MgSO_4$), filtered, and concentrated. The homoallylic alcohol 5 thus obtained was reasonably pure (see $^1H$ NMR spectra FIG. 23A), but for the purpose of obtaining an accurate yield was purified by flash chromatography (88% yield, 92% ee, FIG. 23B).

Example 8

Procedure for the Synthesis of Racemic Compounds

All racemic compounds were prepared by using commercially available cis- and trans-crotylboronic acid pinacol esters (Scheme S1).

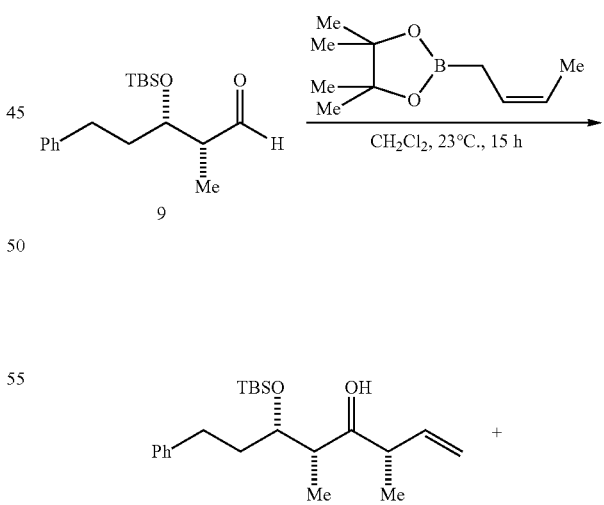

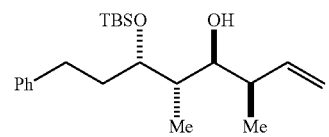

Scheme S3. Preparation of diastereomeric mixtures by crotylboration of 7 (FIG. 11).

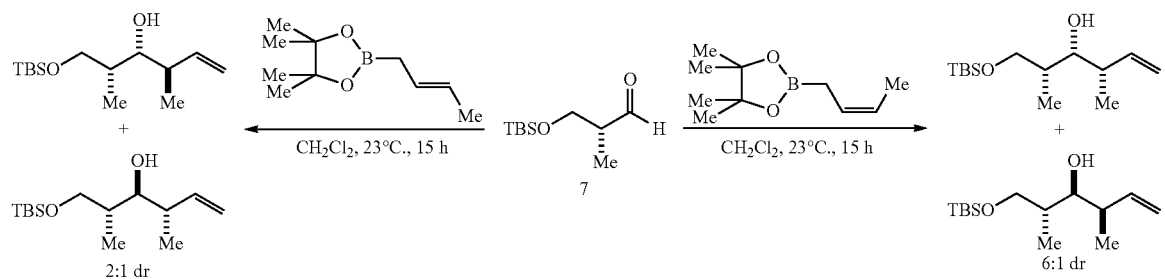

Similar to Scheme S3, preparation of diastereomeric mixtures by crotylboration of 8 (FIG. 12) was also performed.

Preparation of diastereomeric mixtures by allylboration of 7 (FIG. 20A) and 8 (FIG. 21A) was performed using similar techniques.

The invention claimed is:

1. A composition for crotylation of aldehydes comprising a compound of formula A,

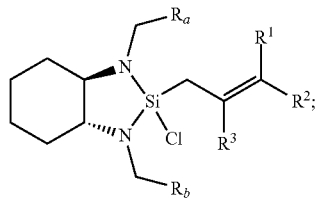

wherein $R^1$, $R^2$, and $R^3$ are independently selected from the group consisting of hydrogen, halogen, and alkyl; and
wherein at least one of $R^1$ and $R^2$ is alkyl; and
wherein $R_a$ and $R_b$ are independently selected from the group consisting of hydrogen, alkyl, aryl and heteroaryl; and
a Lewis acid.

2. The composition of claim 1, wherein $R_a$ and $R_b$ are aryl.

3. The composition of claim 1, wherein the compound of formula A is a compound of formula 1 or 2

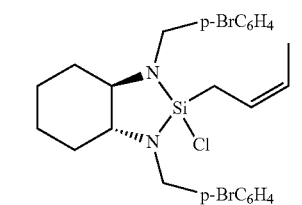

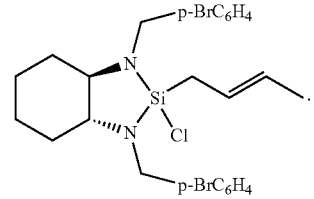

4. The composition of claim 1, wherein the compound is (R,R)-1 or (S,S)-1.

5. The composition of claim 1, wherein the compound is (R,R)-2 or (S,S)-2.

6. The composition of claim 1, wherein the Lewis acid is scandium triflate.

7. The composition of claim 1, wherein the Lewis acid is present in about 10 mol % relative to the amount of compounds of formula A.

8. The composition of claim 1, wherein the Lewis acid is present in about 5 mol % relative to the amount of compounds of formula A.

9. The composition of claim 1, wherein the Lewis acid is present in about 4.4 mol % relative to the amount of compounds of formula A.

10. The composition of claim 1, wherein the Lewis acid is present in about 2 mol % relative to the amount of compounds of formula A.

11. The composition of claim 1, wherein the compound of formula A and the Lewis acid are pre-mixed prior to reaction with the aldehyde.

12. The composition of claim 1, wherein the composition is pre-mixed and stored at ambient temperature prior to reaction with the aldehyde.

13. A composition for allylation of aldehydes comprising a compound of formula A,

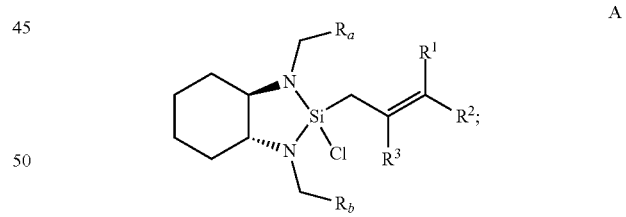

wherein $R^1$ and $R^2$ are independently hydrogen or halogen; and
$R^3$ is selected from the group consisting of hydrogen, halogen, and alkyl; and
wherein $R_a$ and $R_b$ are independently selected from the group consisting of hydrogen, alkyl, aryl and heteroaryl; and
a Lewis acid.

14. The composition of claim 13, wherein $R_a$ and $R_b$ are aryl.

15. The composition of claim 13, wherein the compound of formula A is a compound of formula 13

13

[structure: trans-cyclohexane-1,2-diamine with two p-BrC6H4CH2 groups on N, Si bearing Cl and allyl]

16. The composition of claim 13, wherein the compound is (R,R)-13 or (S,S)-13.

17. The composition of claim 13, wherein the Lewis acid is scandium triflate.

18. The composition of claim 13, wherein the Lewis acid is present in about 10 mol % relative to the amount of compounds of formula A.

19. The composition of claim 13, wherein the Lewis acid is present in about 5 mol % relative to the amount of compounds of formula A.

20. The composition of claim 13, wherein the Lewis acid is present in about 4.4 mol % relative to the amount of compounds of formula A.

21. The composition of claim 13, wherein the Lewis acid is present in about 2 mol % relative to the amount of compounds of formula A.

22. The composition of claim 13, wherein the compound of formula A and the Lewis acid are pre-mixed prior to reaction with the aldehyde.

23. The composition of claim 13, wherein the composition is pre-mixed and stored at ambient temperature prior to reaction with the aldehyde.

24. A method for crotylation of an aldehyde comprising, reaction of the aldehyde with a compound of formula A,

A

[structure with $R_a$, $R_b$, $R^1$, $R^2$, $R^3$]

wherein $R^1$, $R^2$, and $R^3$ are independently selected from the group consisting of hydrogen, halogen, and alkyl; and
wherein at least one of $R^1$ and $R^2$ is alkyl; and
wherein $R_a$ and $R_b$ are independently selected from the group consisting of hydrogen, alkyl, aryl and heteroaryl; and
a Lewis acid.

25. The method of claim 24, wherein $R_a$ and $R_b$ are aryl.

26. The method of claim 24, wherein the compound of formula A is a compound of formula 1 or 2

1

[structure: allyl silane with cyclohexanediamine, two p-BrC6H4CH2 groups]

2

[structure: crotyl silane with cyclohexanediamine, two p-BrC6H4CH2 groups]

27. The method of claim 24, wherein the compound is (R,R)-1 or (S,S)-1.

28. The method of claim 24, wherein the compound is (R,R)-2 or (S,S)-2.

29. The method of claim 24, wherein the Lewis acid is scandium triflate.

30. The method of claim 24, wherein the Lewis acid is used in a catalytic amount.

31. The method of claim 24, wherein the reaction proceeds at ambient temperature.

32. The method of claim 24, wherein the reaction proceeds at 0° C.

33. The method of claim 24, wherein said aldehyde does not react in the absence of Lewis acid.

34. The method of claim 24, wherein the reaction product is enriched in one enantiomer.

35. The method of claim 24, wherein the reaction product is generated in >90% enantiomeric excess.

36. The method of claim 24, wherein the reaction product is generated in >95% enantiomeric excess.

37. The method of claim 24, wherein the reaction product is enriched in one diastereomer.

38. The method of claim 24, wherein the reaction product is generated in >10:1 diastereoselectivity.

39. The method of claim 24, wherein the reaction product is generated in >30:1 diastereoselectivity.

40. The method of claim 24, wherein the reaction product is generated in >40:1 diastereoselectivity.

41. A method for allylation of an aldehyde comprising, reaction of the aldehyde with a compound of formula A,

A

[structure with $R_a$, $R_b$, $R^1$, $R^2$, $R^3$]

wherein $R^1$ and $R^2$ are independently hydrogen or halogen; and
$R^3$ is selected from the group consisting of hydrogen, halogen, and alkyl; and
wherein $R_a$ and $R_b$ are independently selected from the group consisting of hydrogen, alkyl, aryl and heteroaryl; and
a Lewis acid.

42. The method of claim 41, wherein $R_a$ and $R_b$ are aryl.

43. The method of claim 41, wherein the compound of formula A is a compound of formula 13

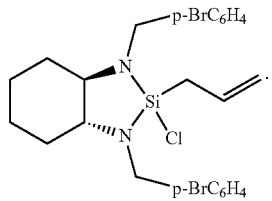

44. The method of claim 41, wherein the compound is (R,R)-13 or (S,S)-13.

45. The method of claim 41, wherein the Lewis acid is scandium triflate.

46. The method of claim 41, wherein the Lewis acid is used in a catalytic amount.

47. The method of claim 41, wherein the reaction proceeds at ambient temperature.

48. The method of claim 41, wherein the reaction proceeds at 0° C.

49. The method of claim 41, wherein said aldehyde does not react in the absence of Lewis acid.

50. The method of claim 41, wherein the reaction product is enriched in one enantiomer.

51. The method of claim 41, wherein the reaction product is generated in >90% enantiomeric excess.

52. The method of claim 41, wherein the reaction product is generated in >95% enantiomeric excess.

53. The method of claim 41, wherein the reaction product is enriched in one diastereomer.

54. The method of claim 41, wherein the reaction product is generated in >10:1 diastereoselectivity.

55. The method of claim 41, wherein the reaction product is generated in >30:1 diastereoselectivity.

56. The method of claim 41, wherein the reaction product is generated in >40:1 diastereoselectivity.

* * * * *